United States Patent
Menke et al.

(10) Patent No.: US 6,602,825 B1
(45) Date of Patent: Aug. 5, 2003

(54) 1-ARYL-1,3,5-TRIAZINE-4-THIONE-2,6-DIONES, PRODUCTION THEREOF AND USE THEREOF AS HERBICIDES

(75) Inventors: Olaf Menke, Altleiningen (DE); Ingo Sagasser, Eppelheim (DE); Gerhard Hamprecht, Weinheim (DE); Robert Reinhard, Ludwigshafen (DE); Cyrill Zagar, Ludwigshafen (DE); Karl-Otto Westphalen, Speyer (DE); Martina Otten, Ludwigshafen (DE); Helmut Walter, Obrigheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/913,466
(22) PCT Filed: Feb. 10, 2000
(86) PCT No.: PCT/EP00/01072
§ 371 (c)(1),
(2), (4) Date: Aug. 15, 2001
(87) PCT Pub. No.: WO00/50409
PCT Pub. Date: Aug. 31, 2000

(51) Int. Cl.$^7$ .................. C07D 251/26; A01N 43/64
(52) U.S. Cl. ............... 504/227; 504/230; 544/221; 544/222; 540/607
(58) Field of Search ................. 544/221, 222; 504/227, 230

(56) References Cited

U.S. PATENT DOCUMENTS

| | | | |
|---|---|---|---|
| 5,447,904 A | 9/1995 | Schallner | 544/221 |
| 5,616,706 A | 4/1997 | Crews | 544/221 |
| 6,080,702 A | 6/2000 | Theodoridis | 504/215 |

FOREIGN PATENT DOCUMENTS

| | | |
|---|---|---|
| DE | 121 517 | 8/1976 |
| DE | 40 00 624 | 7/1991 |
| EP | 584 655 | 3/1994 |
| EP | 640 600 | 3/1995 |
| EP | 745 599 | 12/1996 |
| WO | 97/12886 | 4/1997 |
| WO | 99/05125 | 2/1999 |

OTHER PUBLICATIONS

Derwent Abst. 75783X/41, 8/76.
Patent Abst, of Japan, 56075407, 06/81.

*Primary Examiner*—Venkataraman Balasubramanian
(74) *Attorney, Agent, or Firm*—Keil & Weinkauf

(57) ABSTRACT

Novel 1-aryl-4-thiotriazines I

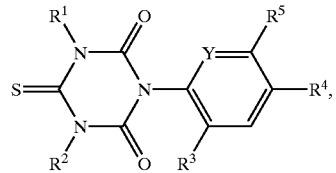

where the variables have the following meanings:
$R^1$=H, $NH_2$, $C_1$–$C_4$-alkyl, $C_1$–$C_4$-haloalkyl;
$R^2$=H, $NH_2$, $C_1$–$C_4$-alkyl, $C_1$–$C_4$-haloalkyl;
$R^3$=H, halogen;
$R^4$=CN, halogen;
Y=nitrogen, the methine group or, together with $R^5$, a bridge >C—O—C($R^6$)=N—;
$R^5$=one of the meanings given in the description;
$R^6$=H, halogen, substituted or unsubstituted $C_1$–$C_6$-alkyl, $C_3$–$C_6$-alkenyl, $C_3$–$C_6$-alkynyl, $C_1$–$C_6$-alkoxy, $C_3$–$C_6$-alkenyloxy, $C_3$–$C_6$-alkynyloxy, $C_3$–$C_6$-cycloalkyl or $C_3$–$C_6$-cycloalkoxy;
their salts and enol ethers, the preparation of the novel compounds I and their use as herbicides.

10 Claims, No Drawings

1-ARYL-1,3,5-TRIAZINE-4-THIONE-2,6-DIONES, PRODUCTION THEREOF AND USE THEREOF AS HERBICIDES

The present invention relates to novel 1-aryl-4-thiotriazines of the formula I

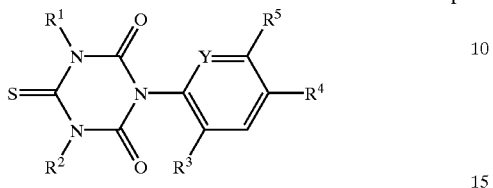

in which the variables have the following meanings:
$R^1$ is hydrogen, amino, $C_1$–$C_4$-alkyl or $C_1$–$C_4$-haloalkyl;
$R^2$ is hydrogen, amino, $C_1$–$C_4$-alkyl or $C_1$–$C_4$-haloalkyl;
$R^3$ is hydrogen or halogen;
$R^4$ is cyano or halogen;
Y is nitrogen, the methine group or, together with $R^5$, is a bridge >C—O—C($R^6$)=N—;
$R^5$ is
1) hydrogen, hydroxyl, mercapto, nitro, halogen, $C_1$–$C_6$-alkyl, $C_1$–$C_6$-haloalkyl,
2) $C_1$–$C_6$-alkoxy, $C_1$–$C_6$-alkylthio, $C_3$–$C_6$-cycloalkoxy, $C_3$–$C_6$-cycloalkylthio, $C_2$–$C_6$-alkenyloxy, $C_2$–$C_6$-alkenylthio, $C_2$–$C_6$-alkynyloxy or $C_2$–$C_6$-alkynylthio, it being possible, if desired, for each of these 8 radicals to have attached to it one of the following substituents: halogen, cyano, —CO—$R^8$, —CO—O$R^8$ or —CO—N($R^8$)—$R^9$;
3) —CO$R^{11}$, —C($R^{11}$)(O$R^{13}$)(O$R^{14}$), —C($R^{11}$)=C($R^{15}$)—CO—$R^{16}$, —CH($R^{11}$)—CH($R^{15}$)—CO—$R^{16}$, —CO—O$R^{20}$, —C($R^{10}$)=N—O$R^7$, —N($R^{21}$)—$R^{22}$ or —CO—N($R^{21}$)—$R^{22}$;
$R^6$ is hydrogen, halogen, $C_1$–$C_6$-alkyl, $C_3$–$C_6$-alkenyl, $C_3$–$C_6$-alkynyl, $C_1$–$C_6$-alkoxy, $C_3$–$C_6$-alkenyloxy, $C_3$–$C_6$-alkynyloxy, $C_3$–$C_6$-cycloalkyl or $C_3$–$C_6$-cycloalkoxy, it being possible for each of the last-mentioned 8 radicals, if desired, to have attached to it one to three substituents, in each case selected from the group consisting of halogen, $C_1$–$C_6$-alkoxy and —CO—O$R^{8'}$;
$R^7$ is hydrogen, $C_1$–$C_6$-alkyl, $C_1$–$C_6$-haloalkyl, $C_3$–$C_6$-cycloalkyl, $C_3$–$C_6$-alkenyl, $C_3$–$C_6$-alkynyl, ($C_1$–$C_6$-alkoxy)carbonyl-$C_1$–$C_6$-alkyl, or benzyl;
$R^8$, $R^{8'}$ independently of one another are hydrogen, $C_1$–$C_6$-alkyl, $C_3$–$C_6$-cycloalkyl, $C_3$–$C_6$-cycloalkyl-$C_1$–$C_4$-alkyl, $C_3$–$C_6$-alkenyl, $C_3$–$C_6$-alkynyl, $C_1$–$C_6$-alkoxy-$C_1$–$C_6$-alkyl, ($C_1$–$C_6$-alkoxy)carbonyl-$C_1$–$C_6$-alkyl, ($C_3$–$C_6$-alkenyloxy)carbonyl-$C_1$–$C_6$-alkyl, phenyl or phenyl-$C_1$–$C_6$-alkyl, it being possible for the phenyl group and the phenyl ring of the phenyl alkyl group to be unsubstituted or to have attached to them one to three radicals, in each case selected from the group consisting of halogen, nitro, cyano, $C_1$–$C_6$-alkyl, $C_1$–$C_6$-haloalkyl, $C_1$–$C_6$-alkoxy and ($C_1$–$C_6$-alkyl) carbonyl;
$R^9$ is hydrogen or $C_1$–$C_6$-alkyl;
$R^{10}$ is hydrogen, $C_1$–$C_6$-alkyl or $C_1$–$C_6$-alkoxy, it being possible for the 2 last-mentioned radicals to have attached to them one of the following substituents: $C_1$–$C_6$-alkoxy, ($C_1$–$C_6$-alkoxy)carbonyl or phenoxycarbonyl;
$R^{11}$ is hydrogen, $C_1$–$C_6$-alkyl or $C_1$–$C_6$-haloalkyl;
$R^{13}$, $R^{14}$ independently of one another are $C_1$–$C_6$-alkyl or together are a saturated 2- to 4-membered carbon chain which can have attached to it a $C_1$–$C_6$-alkyl radical;
$R^{15}$ is hydrogen, cyano, halogen or $C_1$–$C_6$-alkyl;
$R^{16}$ is O—$R^{23}$ or —N($R^{21}$)$R^{22}$;
$R^{20}$, $R^{23}$ independently of one another are hydrogen, $C_1$–$C_6$-alkyl, $C_1$–$C_6$-haloalkyl, $C_2$–$C_6$-alkenyl or $C_2$–$C_6$-alkynyl, it being possible for each of the last-mentioned 4 groups to have attached to it one or two of the following radicals: cyano, halogen, hydroxyl, hydroxycarbonyl, $C_1$–$C_6$-alkoxy, $C_1$–$C_6$-alkylthio, ($C_1$–$C_6$-alkyl)carbonyl, ($C_1$–$C_6$-alkoxy)carbonyl, ($C_1$–$C_6$-alkyl)carbonyloxy, ($C_3$–$C_6$-alkenyloxy) carbonyl, ($C_3$–$C_6$-alkynyloxy)carbonyl or $C_1$–$C_6$-alkoxy-($C_1$–$C_6$-alkoxy)carbonyl; or $C_3$–$C_6$-cycloalkyl, phenyl or phenyl-$C_1$–$C_6$-alkyl, where the phenyl rings can be unsubstituted or, in turn, can have attached to them one to three substituents, in each case selected from the group consisting of cyano, nitro, halogen, $C_1$–$C_6$-alkyl, $C_1$–$C_6$-haloalkyl, $C_1$–$C_6$-alkoxy and ($C_1$–$C_6$-alkoxy)carbonyl;
$R^{21}$, $R^{22}$ independently of one another are hydrogen, $C_1$–$C_6$-alkyl, $C_3$–$C_6$-alkenyl, $C_2$–$C_6$-alkynyl, $C_3$–$C_6$-cycloalkyl, $C_1$–$C_6$-haloalkyl, $C_1$–$C_6$-alkoxy-$C_1$–$C_6$-alkyl, ($C_1$–$C_6$-alkyl)carbonyl, ($C_1$–$C_6$-alkoxy) carbonyl, ($C_1$–$C_6$-alkoxy)carbonyl-$C_1$–$C_6$-alkyl or $C_1$–$C_6$-alkylsulfonyl,
or $R^{21}$ and $R^{22}$ together with the joint nitrogen atom, are a saturated or unsaturated 4- to 7-membered aza heterocycle which, if desired, may contain one of the following members, in addition to carbon ring members: —O—, —S—, —N=, —NH— or —N($C_1$–$C_6$-alkyl)—;
and the agriculturally useful salts and enol ethers of the compounds I.

Moreover, the invention relates to
the use of the compounds I as herbicides,
herbicidal compositions which comprise the compounds I as active substances,
processes for the preparation of the compounds I and of herbicidal compositions using the compounds I, and
methods of controlling undesirable vegetation using the compounds I.

DE-A 40 00 624 describes the specifically substituted 1-phenyltriazines as having a fungicidal action. A herbicidal action is not mentioned. Thiotriazines are not mentioned.

EP-A 640 600 describes substituted 4-thiotriazines which have a herbicidal action and which are 4-5-fused in the phenyl substituent.

The subject-matter of EP-A 584 655 and—to a small extent—also WO99/05125 is aryltriazinetriones of the type of the compounds I and their use as herbicides. A multiplicity of aryltriazines and arylthiotriazines fall under the general formulae; however, individual compounds having a thioketone group in the triazine moiety are not mentioned in either publication.

We have found that arylthiotriazines of the formula I as defined above have a particularly good herbicidal action. There have also been found herbicidal compositions which comprise the compounds I and which have a very good herbicidal action. Moreover, there have been found processes for the preparation of these compositions and methods for controlling undesirable vegetation using the compounds I.

Depending on the substitution pattern, the compounds of the formula I can contain one or more chiral centers, in which case they are present as enantiomer or diastereomer mixtures. In the case of compounds I which contain at least one olefinic residue, E/Z isomers may also be possible. Subject-matter of the invention are not only the pure enantiomers or diastereomers but also their mixtures.

Suitable amongst agriculturally useful salts are especially the salts of those cations, or the acid addition salts of those acids, whose cations or anions, respectively, do not adversely affect the herbicidal action of the compounds I. Thus, especially suitable cations are the ions of the alkali metals, preferably sodium and potassium, of the alkaline earth metals, preferably calcium, magnesium and barium, and of the transition metals, preferably manganese, copper, zinc and iron, and also the ammonium ion which, if desired, can have attached to it one to four $C_1$–$C_4$-alkyl substituents and/or one phenyl or benzyl substituent, preferably diisopropylammonium, tetramethylammonium, tetrabutylammonium, trimethylbenzylammonium, moreover phosphonium ions, sulfonium ions, preferably tri($C_1$–$C_4$-alkyl)sulfonium and sulfoxonium ions, preferably tri($C_1$–$C_4$-alkyl)sulfoxonium.

Anions of useful acid addition salts are mainly chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and the anions of $C_1$–$C_4$-alkanoic acids, preferably formate, acetate, propionate and butyrate.

The organic moieties mentioned in the definition of $R^1$ to $R^3$, $R^5$ to $R^{23}$ and on phenyl, cycloalkyl and heterocyclyl rings are collective terms for individual enumerations of the individual group members. All carbon chains, that is to say all (unsubstituted or substituted) alkyl, alkenyl or alkynyl moieties, can be straight-chain or branched.

Halogenated substituents preferably have attached to them one to five identical or different halogen atoms.

The meaning halogen is in each case fluorine, bromine, chlorine or iodine, in particular fluorine or chlorine.

Examples of other meanings are:

$C_1$–$C_4$-alkyl: $CH_3$, $C_2H_5$, n-propyl, $CH(CH_3)_2$, n-butyl, $CH(CH_3)$-$C_2H_5$, 2-methylpropyl or $C(CH_3)_3$, in particular $CH_3$, $C_2H_5$ or $CH(CH_3)_2$;

$C_1$–$C_4$-haloalkyl: a $C_1$–$C_4$-alkyl radical as mentioned above which is partially or fully substituted by fluorine, chlorine, bromine and/or iodine, e.g. $CH_2F$, $CHF_2$, $CF_3$, $CH_2Cl$, dichloromethyl, trichloromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, $C_2F_5$, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, $CH_2$-$C_2F_5$, $CF_2$-$C_2F_5$, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl, in particular $CH_2F$, $CHF_2$, $CF_3$, $CH_2Cl$, 2-fluoroethyl, 2-chloroethyl or 2,2,2-trifluoroethyl;

$C_1$–$C_6$-alkyl: $C_1$–$C_4$-alkyl as mentioned above and, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, in particular $CH_3$, $C_2H_5$, n-propyl, $CH(CH_3)_2$, n-butyl, $C(CH_3)_3$, n-pentyl or n-hexyl;

$C_1$–$C_6$-haloalkyl: $C_1$–$C_6$-alkyl as mentioned above which is partially or fully substituted by fluorine, chlorine, bromine and/or iodine, e.g. one of the radicals mentioned under $C_1$–$C_4$-haloalkyl or 5-fluoro-1-pentyl, 5-chloro-1-pentyl, 5-bromo-1-pentyl, 5-iodo-1-pentyl, 5,5,5-trichloro-1-pentyl, undecafluoropentyl, 6-fluoro-1-hexyl, 6-chloro-1-hexyl, 6-bromo-1-hexyl, 6-iodo-1-hexyl, 6,6,6-trichloro-1-hexyl or dodecafluorohexyl, in particular chloromethyl, fluoromethyl, difluoromethyl, trifluoromethyl, 2-fluoroethyl, 2-chloroethyl or 2,2,2-trifluoroethyl;

phenyl-$C_1$–$C_6$-alkyl: for example benzyl, 1-phenylethyl, 2-phenylethyl, 1-phenylprop-1-yl, 2-phenylprop-1-yl, 3-phenylprop-1-yl, 1-phenylbut-1-yl, 2-phenylbut-1-yl, 3-phenylbut-1-yl, 4-phenylbut-1-yl, 1-phenylbut-2-yl, 2-phenylbut-2-yl, 3-phenylbut-2-yl, 4-phenylbut-2-yl, 1-(phenylmethyl)eth-1-yl, 1-(phenylmethyl)-1-(methyl)eth-1-yl or 1-(phenylmethyl)prop-1-yl, in particular benzyl or 2-phenylethyl;

($C_1$–$C_6$-alkyl)carbonyl: CO—$CH_3$, CO—$C_2H_5$, n-propylcarbonyl, 1-methylethylcarbonyl, n-butylcarbonyl, 1-methylpropylcarbonyl, 2-methylpropylcarbonyl, 1,1-dimethylethylcarbonyl, n-pentylcarbonyl, 1-methylbutylcarbonyl, 2-methylbutylcarbonyl, 3-methylbutylcarbonyl, 1,1-dimethylpropylcarbonyl, 1,2-dimethylpropylcarbonyl, 2,2-dimethylpropylcarbonyl, 1-ethylpropylcarbonyl, n-hexylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl or 1-ethyl-2-methylpropylcarbonyl, in particular CO—$CH_3$, CO—$C_2H_5$ or CO—$CH(CH_3)_2$;

$C_1$–$C_6$-alkoxy: for example $OCH_3$, $OC_2H_5$, $OCH_2$—$C_2H_5$, $OCH(CH_3)_2$, n-butoxy, $OCH(CH_3)$—$C_2H_5$, $OCH_2$—$CH(CH_3)_2$, $OC(CH_3)_3$, n-pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy, in particular $OCH_3$, $OC_2H_5$ or $OCH(CH_3)_2$;

($C_1$–$C_6$-alkoxy)carbonyl: for example CO—$OCH_3$, CO—$OC_2H_5$, CO—$CH_2$—$C_2H_5$, CO—$OCH(CH_3)_2$, n-butoxycarbonyl, CO—$OCH(CH_3)$—$C_2H_5$, CO—$OCH_2$—$CH(CH_3)_2$, CO—$OC(CH_3)_3$, n-pentoxycarbonyl, 1-methylbutoxycarbonyl, 2-methylbutoxycarbonyl, 3-methylbutoxycarbonyl, 2,2-dimethylpropoxycarbonyl, 1-ethylpropoxycarbonyl, n-hexoxycarbonyl, 1,1-dimethylpropoxycarbonyl, 1,2-dimethylpropoxycarbonyl, 1-methylpentoxycarbonyl, 2-methylpentoxycarbonyl, 3-methylpentoxycarbonyl, 4-methylpentoxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,3-dimethylbutoxycarbonyl, 3,3-dimethylbutoxycarbonyl, 1-ethylbutoxycarbonyl, 2-ethylbutoxycarbonyl, 1,1,2-trimethylpropoxycarbonyl, 1,2,2-trimethylpropoxycarbonyl, 1-ethyl-1-methylpropoxycarbonyl or 1-ethyl-2-methylpropoxycarbonyl, in particular CO—OCH$_3$, CO—OC$_2$H$_5$, CO—OCH(CH$_3$)$_2$ or CO—CH$_2$—CH(CH$_3$)$_2$;

($C_1$–$C_6$-alkoxy)carbonyloxy: methoxycarbonyloxy, ethoxycarbonyloxy, n-propoxycarbonyloxy, 1-methylethoxycarbonyloxy, n-butoxycarbonyloxy, 1-methylpropoxycarbonyloxy, 2-methylpropoxycarbonyloxy, 1,1-dimethylethoxycarbonyloxy, n-pentoxycarbonyloxy, 1-methylbutoxycarbonyloxy, 2-methylbutoxycarbonyloxy, 3-methylbutoxycarbonyloxy, 2,2-dimethylpropoxycarbonyloxy, 1-ethylpropoxycarbonyloxy, n-hexoxycarbonyloxy, 1,1-dimethylpropoxycarbonyloxy, 1,2-dimethylpropoxycarbonyloxy, 1-methylpentoxycarbonyloxy, 2-methylpentoxycarbonyloxy, 3-methylpentoxycarbonyloxy, 4-methylpentoxycarbonyloxy, 1,1-dimethylbutoxycarbonyloxy, 1,2-dimethylbutoxycarbonyloxy, 1,3-dimethylbutoxycarbonyloxy, 2,2-dimethylbutoxycarbonyloxy, 2,3-dimethylbutoxycarbonyloxy, 3,3-dimethylbutoxycarbonyloxy, 1-ethylbutoxycarbonyloxy, 2-ethylbutoxycarbonyloxy, 1,1,2-trimethylpropoxycarbonyloxy, 1,2,2-trimethylpropoxycarbonyloxy, 1-ethyl-1-methylpropoxycarbonyloxy or 1-ethyl-2-methylpropoxycarbonyloxy, in particular methoxycarbonyloxy, ethoxycarbonyloxy or 1-methylethoxycarbonyloxy;

$C_1$–$C_6$-alkylthio: SCH$_3$, SC$_2$H$_5$, SCH$_2$—C$_2$H$_5$, SCH(CH$_3$)$_2$, n-butylthio, 1-methylpropylthio, 2-methylpropylthio, SC(CH$_3$)$_3$, n-pentylthio, 1-methylbutylthio, 2-methylbutylthio, 3-methylbutylthio, 2,2-dimethylpropylthio, 1-ethylpropylthio, n-hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio, in particular SCH$_3$ or SC$_2$H$_5$;

$C_1$–$C_6$-alkylsulfonyl: SO$_2$—CH$_3$, SO$_2$—C$_2$H$_5$, n-propylsulfonyl, SO$_2$—CH(CH$_3$)$_2$, n-butylsulfonyl, 1-methylpropylsulfonyl, 2-methylpropylsulfonyl, SO$_2$—C(CH$_3$)$_3$, n-pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, n-hexylsulfonyl, 1-methylpentylsulfonyl, 2-methylpentylsulfonyl, 3-methylpentylsulfonyl, 4-methylpentylsulfonyl, 11-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl, in particular SO$_2$—CH$_3$;

$C_1$–$C_6$-alkoxy-$C_1$–$C_6$-alkyl: $C_1$–$C_6$-alkyl which is substituted by $C_1$–$C_6$-alkoxy as mentioned above, i.e., for example, CH$_2$—OCH$_3$, CH$_2$—OC$_2$H$_5$, n-propoxymethyl, CH$_2$—OCH(CH$_3$)$_2$, n-butoxymethyl, (1-methylpropoxy)methyl, (2-methylpropoxy)methyl, CH$_2$—OC(CH$_3$)$_3$, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(n-propoxy)butyl, 2-(1-methylethoxy)butyl, 2-(n-butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(n-propoxy)butyl, 4-(1-methylethoxy)butyl, 4-(n-butoxy)butyl, 4-(1-methylpropoxy)butyl, 4-(2-methylpropoxy)butyl or 4-(1,1-dimethylethoxy)butyl, in particular CH$_2$—OCH$_3$ or 2-methoxyethyl;

$C_1$–$C_6$-alkoxy-($C_1$–$C_6$-alkoxy)carbonyl: ($C_1$–$C_6$-alkoxy)carbonyl which is substituted by ($C_1$–$C_6$-alkoxy) as mentioned above, e.g. CO—OCH$_2$—OCH$_3$, CO—OCH$_2$—OC$_2$H$_5$, CO—OCH$_2$—OCH$_2$—C$_2$H$_5$, CO—OCH$_2$—OCH(CH$_3$)$_2$, n-butoxymethoxycarbonyl, (1-methylpropoxy)methoxycarbonyl, CO—OCH$_2$—OCH$_2$—CH(CH$_3$)$_2$, CO—OCH$_2$—OC(CH$_3$)$_3$, 2-(methoxy)ethoxycarbonyl, 2-(ethoxy)ethoxycarbonyl, 2-(n-propoxy)ethoxycarbonyl, 2-(1-methylethoxy)ethoxycarbonyl, 2-(n-butoxy)ethoxycarbonyl, 2-(1-methylpropoxy)ethoxycarbonyl, 2-(2-methylpropoxy)ethoxycarbonyl, 2-(1,1-dimethylethoxy)ethoxycarbonyl, 2-(methoxy)propoxycarbonyl, 2-(ethoxy)propoxycarbonyl, 2-(n-propoxy)propoxycarbonyl, 2-(1-methylethoxy)propoxycarbonyl, 2-(n-butoxy)propoxycarbonyl, 2-(1-methylpropoxy)propoxycarbonyl, 2-(2-methylpropoxy)propoxycarbonyl, 2-(1,1-dimethylethoxy)propoxycarbonyl, 3-(methoxy)propoxycarbonyl, 3-(ethoxy)propoxycarbonyl, 3-(n-propoxy)propoxycarbonyl, 3-(1-methylethoxy)propoxycarbonyl, 3-(n-butoxy)propoxycarbonyl, 3-(1-methylpropoxy)propoxycarbonyl, 3-(2-methylpropoxy)propoxycarbonyl, 3-(1,1-dimethylethoxy)propoxycarbonyl, 2-(methoxy)butoxycarbonyl, 2-(ethoxy)butoxycarbonyl, 2-(n-propoxy)butoxycarbonyl, 2-(1-methylethoxy)butoxycarbonyl, 2-(n-butoxy)butoxycarbonyl, 2-(1-methylpropoxy)butoxycarbonyl, 2-(2-methylpropoxy)

butoxycarbonyl, 2-(1,1-dimethylethoxy)butoxycarbonyl, 3-(methoxy)butoxycarbonyl, 3-(ethoxy)butoxycarbonyl, 3-(n-propoxy)butoxycarbonyl, 3-(1-methylethoxy)butoxycarbonyl, 3-(n-butoxy)butoxycarbonyl, 3-(1-methylpropoxy)butoxycarbonyl, 3-(2-methylpropoxy)butoxycarbonyl, 3-(1,1-dimethylethoxy)butoxycarbonyl, 4-(methoxy)butoxycarbonyl, 4-(ethoxy)butoxycarbonyl, 4-(n-propoxy)butoxycarbonyl, 4-(1-methylethoxy)butoxycarbonyl, 4-(n-butoxy)butoxycarbonyl, 4-(1-methylpropoxy)butoxycarbonyl, 4-(2-methylpropoxy)butoxycarbonyl, 4-(1,1-dimethylethoxy)butoxycarbonyl, 5-(methoxy)pentoxycarbonyl, 5-(ethoxy)pentoxycarbonyl, 5-(n-propoxy)pentoxycarbonyl, 5-(1-methylethoxy)pentoxycarbonyl, 5-(n-butoxy)pentoxycarbonyl, 5-(1-methylpropoxy)pentoxycarbonyl, 5-(2-methylpropoxy)pentoxycarbonyl, 5-(1,1-dimethylethoxy)pentoxycarbonyl, 6-(methoxy)hexoxycarbonyl, 6-(ethoxy)hexoxycarbonyl, 6-(n-propoxy)hexoxycarbonyl, 6-(1-methylethoxy)hexoxycarbonyl, 6-(n-butoxy)hexoxycarbonyl, 6-(1-methylpropoxy)hexoxycarbonyl, 6-(2-methylpropoxy)hexoxycarbonyl or 6-(1,1-dimethylethoxy)hexoxycarbonyl, in particular CO—OCH$_2$—OCH$_3$ or CO—OCH$_2$—OC$_2$H$_5$;

($C_1$–$C_6$-alkoxy)carbonyl-$C_1$–$C_6$-alkyl: $C_1$–$C_6$-alkyl which is substituted by ($C_1$–$C_6$-alkoxy)carbonyl as mentioned above, e.g. methoxycarbonylmethyl, ethoxycarbonylmethyl, 1-(methoxycarbonyl)ethyl, 2-(methoxycarbonyl)ethyl, 2-(ethoxycarbonyl)ethyl, 3-(methoxycarbonyl)propyl, 4-(methoxycarbonyl)butyl, 5-(methoxycarbonyl)pentyl or 6-(methoxycarbonyl)hexyl;

$C_3$–$C_6$-alkenyl: for example prop-2-en-1-yl, n-buten-4-yl, 1-methylprop-2-en-1-yl, 2-methylprop-2-en-1-yl, 2-buten-1-yl, n-penten-3-yl, n-penten-4-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-2-en-1-yl, 1-ethylprop-2-en-1-yl, n-hex-3-en-1-yl, n-hex-4-en-1-yl, n-hex-5-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-2-en-1-yl, 1,2-dimethylbut-3-en-1-yl, 1,3-dimethylbut-2-en-1-yl, 1,3-dimethylbut-3-en-1-yl, 2,2-dimethylbut-3-en-1-yl, 2,3-dimethylbut-2-en-1-yl, 2,3-dimethylbut-3-en-1-yl, 3,3-dimethylbut-2-en-1-yl, 1-ethylbut-2-en-1-yl, 1-ethylbut-3-en-1-yl, 2-ethylbut-2-en-1-yl, 2-ethylbut-3-en-1-yl, 1,1,2-trimethylprop-2-en-1-yl, 1-ethyl-l-methylprop-2-en-1-yl or 1-ethyl-2-methylprop-2-en-1-yl, in particular prop-2-en-1-yl or n-buten-4-yl;

$C_2$–$C_6$-alkenyl: ethenyl or one of the radicals mentioned under $C_3$–$C_6$-alkenyl, in particular ethenyl or prop-2-en-1-yl;

$C_3$–$C_6$-alkenyloxy: prop-1-en-1-yloxy, prop-2-en-1-yloxy, 1-methylethenyloxy, n-buten-1-yloxy, n-buten-2-yloxy, n-buten-3-yloxy, 1-methylprop-1-en-1-yloxy, 2-methylprop-1-en-1-yloxy, 1-methylprop-2-en-1-yloxy, 2-methylprop-2-en-1-yloxy, n-penten-1-yloxy, n-penten-2-yloxy, n-penten-3-yloxy, n-penten-4-yloxy, 1-methylbut-1-en-1-yloxy, 2-methylbut-1-en-1-yloxy, 3-methylbut-1-en-1-yloxy, 1-methylbut-2-en-1-yloxy, 2-methylbut-2-en-1-yloxy, 3-methylbut-2-en-1-yloxy, 1-methylbut-3-en-1-yloxy, 2-methylbut-3-en-1-yloxy, 3-methylbut-3-en-1-yloxy, 1,1-dimethylprop-2-en-1-yloxy, 1,2-dimethylprop-1-en-1-yloxy, 1,2-dimethylprop-2-en-1-yloxy, 1-ethylprop-1-en-2-yloxy, 1-ethylprop-2-en-1-yloxy, n-hex-1-en-1-yloxy, n-hex-2-en-1-yloxy, n-hex-3-en-1-yloxy, n-hex-4-en-1-yloxy, n-hex-5-en-1-yloxy, 1-methylpent-1-en-1-yloxy, 2-methylpent-1-en-1-yloxy, 3-methylpent-1-en-1-yloxy, 4-methylpent-1-en-1-yloxy, 1-methylpent-2-en-1-yloxy, 2-methylpent-2-en-1-yloxy, 3-methylpent-2-en-1-yloxy, 4-methylpent-2-en-1-yloxy, 1-methylpent-3-en-1-yloxy, 2-methylpent-3-en-1-yloxy, 3-methylpent-3-en-1-yloxy, 4-methylpent-3-en-1-yloxy, 1-methylpent-4-en-1-yloxy, 2-methylpent-4-en-1-yloxy, 3-methylpent-4-en-1-yloxy, 4-methylpent-4-en-1-yloxy, 1,1-dimethylbut-2-en-1-yloxy, 1,1-dimethylbut-3-en-1-yloxy, 1,2-dimethylbut-1-en-1-yloxy, 1,2-dimethylbut-2-en-1-yloxy, 1,2-dimethylbut-3-en-1-yloxy, 1,3-dimethylbut-1-en-1-yloxy, 1,3-dimethylbut-2-en-1-yloxy, 1,3-dimethylbut-3-en-1-yloxy, 2,2-dimethylbut-3-en-1-yloxy, 2,3-dimethylbut-1-en-1-yloxy, 2,3-dimethylbut-2-en-1-yloxy, 2,3-dimethylbut-3-en-1-yloxy, 3,3-dimethylbut-1-en-1-yloxy, 3,3-dimethylbut-2-en-1-yloxy, 1-ethylbut-1-en-1-yloxy, 1-ethylbut-2-en-1-yloxy, 1-ethylbut-3-en-1-yloxy, 2-ethylbut-1-en-1-yloxy, 2-ethylbut-2-en-1-yloxy, 2-ethylbut-3-en-1-yloxy, 1,1,2-trimethylprop-2-en-1-yloxy, 1-ethyl-1-methylprop-2-en-1-yloxy, 1-ethyl-2-methylprop-1-en-1-yloxy or 1-ethyl-2-methylprop-2-en-1-yloxy, in particular prop-2-en-1-yloxy;

$C_2$–$C_6$-alkenyloxy: ethenyloxy or one of the radicals mentioned under $C_3$–$C_6$-alkenyloxy, in particular ethenyloxy or prop-2-en-1-yloxy;

$C_2$–$C_6$-alkenylthio: ethenylthio, prop-1-en-1-ylthio, prop-2-en-1-ylthio, 1-methylethenylthio, n-buten-1-ylthio, n-buten-2-ylthio, n-buten-3-ylthio, 1-methylprop-1-en-1-ylthio, 2-methylprop-1-en-1-ylthio, 1-methylprop-2-en-1-ylthio, 2-methylprop-2-en-1-ylthio, n-penten-1-ylthio, n-penten-2-ylthio, n-penten-3-ylthio, n-penten-4-ylthio, 1-methylbut-1-en-1-ylthio, 2-methylbut-1-en-1-ylthio, 3-methylbut-1-en-1-ylthio, 1-methylbut-2-en-1-ylthio, 2-methylbut-2-en-1-ylthio, 3-methylbut-2-en-1-ylthio, 1-methylbut-3-en-1-ylthio, 2-methylbut-3-en-1-ylthio, 3-methylbut-3-en-1-ylthio, 1,1-dimethylprop-2-en-1-ylthio, 1,2-dimethylprop-1-en-1-ylthio, 1,2-dimethylprop-2-en-1-ylthio, 1-ethylprop-1-en-2-ylthio, 1-ethylprop-2-en-1-ylthio, n-hex-1-en-1-ylthio, n-hex-2-en-1-ylthio, n-hex-3-en-1-ylthio, n-hex-4-en-1-ylthio, n-hex-5-en-1-ylthio, 1-methylpent-1-en-1-ylthio, 2-methylpent-1-en-1-ylthio, 3-methylpent-1-en-1-ylthio, 4-methylpent-1-en-1-ylthio, 1-methylpent-2-en-1-ylthio, 2-methylpent-2-en-1-ylthio, 3-methylpent-2-en-1-ylthio, 4-methylpent-2-en-1-ylthio, 1-methylpent-3-en-1-ylthio, 2-methylpent-3-en-1-ylthio, 3-methylpent-3-en-1-ylthio, 4-methylpent-3-en-1-ylthio, 1-methylpent-4-en-1-ylthio, 2-methylpent-4-en-1-ylthio, 3-methylpent-4-en-1-ylthio, 4-methylpent-4-en-1-ylthio, 1,1-dimethylbut-2-en-1-ylthio, 1,1-dimethylbut-3-en-1-ylthio, 1,2-dimethylbut-1-en-1-ylthio, 1,2-dimethylbut-2-en-1-ylthio, 1,2-dimethylbut-3-en-1-ylthio, 1,3-dimethylbut-1-en-1-ylthio, 1,3-dimethylbut-2-en-1-ylthio, 1,3-dimethylbut-3-en-1-ylthio, 2,2-dimethylbut-3-en-1-ylthio, 2,3-dimethylbut-1-en-1-ylthio, 2,3-dimethylbut-2-en-1-ylthio, 2,3-dimethylbut-3-en-1-ylthio, 3,3-dimethylbut-1-en-1-ylthio, 3,3- dimethylbut-2-en-1-ylthio, 1-ethylbut-1-en-1-ylthio, 1-ethylbut-2-en-1-ylthio, 1-ethylbut-3-en-1-ylthio, 2-ethylbut-1-en-1-ylthio, 2-ethylbut-2-en-1-ylthio, 2-ethylbut-3-en-1-ylthio, 1,1,2-trimethylprop-2-en-1-ylthio, 1-ethyl-1-methylprop-2-en-1-ylthio, 1-ethyl-2-methylprop-1-en-1-ylthio or 1-ethyl-2-methylprop-2-en-1-ylthio, in particular ethenylthio or prop-2-en-1-ylthio;

$C_3$–$C_6$-alkynyl: prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl, in particular prop-2-yn-1-yl;

$C_2$–$C_6$-alkynyl: ethynyl or one of the radicals mentioned under $C_3$–$C_6$-alkynyl, in particular ethynyl or prop-2-yn-1-yl;

$C_3$–$C_6$-alkynyloxy: prop-1-yn-1-yloxy, prop-2-yn-1-yloxy, n-but-1-yn-1-yloxy, n-but-1-yn-3-yloxy, n-but-1-yn-4-yloxy, n-but-2-yn-1-yloxy, n-pent-1-yn-1-yloxy, n-pent-1-yn-3-yloxy, n-pent-1-yn-4-yloxy, n-pent-1-yn-5-yloxy, n-pent-2-yn-1-yloxy, n-pent-2-yn-4-yloxy, n-pent-2-yn-5-yloxy, 3-methylbut-1-yn-3-yloxy, 3-methylbut-1-yn-4-yloxy, n-hex-1-yn-1-yloxy, n-hex-1-yn-3-yloxy, n-hex-1-yn-4-yloxy, n-hex-1-yn-5-yloxy, n-hex-1-yn-6-yloxy, n-hex-2-yn-1-yloxy, n-hex-2-yn-4-yloxy, n-hex-2-yn-5-yloxy, n-hex-2-yn-6-yloxy, n-hex-3-yn-1-yloxy, n-hex-3-yn-2-yloxy, 3-methylpent-1-yn-1-yloxy, 3-methylpent-1-yn-3-yloxy, 3-methylpent-1-yn-4-yloxy, 3-methylpent-1-yn-5-yloxy, 4-methylpent-1-yn-1-yloxy, 4-methylpent-2-yn-4-yloxy or 4-methylpent-2-yn-5-yloxy, in particular prop-2-yn-1-yloxy;

$C_2$–$C_6$-alkynyloxy: ethynyloxy or one of the radicals mentioned under $C_3$–$C_6$-alkynyloxy, in particular ethynyloxy or prop-2-yn-1-yloxy;

$C_2$–$C_6$-alkynylthio: ethynylthio or one of the radicals mentioned under $C_3$–$C_6$-alkynylthio, in particular ethynylthio or prop-2-yn-1-ylthio;

($C_3$–$C_6$-alkenyloxy)carbonyl: prop-1-en-1-yloxycarbonyl, prop-2-en-1-yloxycarbonyl, 1-methylethenyloxycarbonyl, n-buten-1-yloxycarbonyl, n-buten-2-yloxycarbonyl, n-buten-3-yloxycarbonyl, 1-methylprop-1-en-1-yloxycarbonyl, 2-methylprop-1-en-1-yloxycarbonyl, 1-methylprop-2-en-1-yloxycarbonyl, 2-methylprop-2-en-1-yloxycarbonyl, n-penten-1-yloxycarbonyl, n-penten-2-yloxycarbonyl, n-penten-3-yloxycarbonyl, n-penten-4-yloxycarbonyl, 1-methylbut-1-en-1-yloxycarbonyl, 2-methylbut-1-en-1-yloxycarbonyl, 3-methylbut-1-en-1-yloxycarbonyl, 1-methylbut-2-en-1-yloxycarbonyl, 2-methylbut-2-en-1-yloxycarbonyl, 3-methylbut-2-en-1-yloxycarbonyl, 1-methylbut-3-en-1-yloxycarbonyl, 2-methylbut-3-en-1-yloxycarbonyl, 3-methylbut-3-en-1-yloxycarbonyl, 1,1-dimethylprop-2-en-1-yloxycarbonyl, 1,2-dimethylprop-1-en-1-yloxycarbonyl, 1,2-dimethylprop-2-en-1-yloxycarbonyl, 1-ethylprop-1-en-2-yloxycarbonyl, 1-ethylprop-2-en-1-yloxycarbonyl, n-hex-1-en-1-yloxycarbonyl, n-hex-2-en-1-yloxycarbonyl, n-hex-3-en-1-yloxycarbonyl, n-hex-4-en-1-yloxycarbonyl, n-hex-5-en-1-yloxycarbonyl, 1-methylpent-1-en-1-yloxycarbonyl, 2-methylpent-1-en-1-yloxycarbonyl, 3-methylpent-1-en-1-yloxycarbonyl, 4-methylpent-1-en-1-yloxycarbonyl, 1-methylpent-2-en-1-yloxycarbonyl, 2-methylpent-2-en-1-yloxycarbonyl, 3-methylpent-2-en-1-yloxycarbonyl, 4-methylpent-2-en-1-yloxycarbonyl, 1-methylpent-3-en-1-yloxycarbonyl, 2-methylpent-3-en-1-yloxycarbonyl, 3-methylpent-3-en-1-yloxycarbonyl, 4-methylpent-3-en-1-yloxycarbonyl, 1-methylpent-4-en-1-yloxycarbonyl, 2-methylpent-4-en-1-yloxycarbonyl, 3-methylpent-4-en-1-yloxycarbonyl, 4-methylpent-4-en-1-yloxycarbonyl, 1,1-dimethylbut-2-en-1-yloxycarbonyl, 1,1-dimethylbut-3-en-1-yloxycarbonyl, 1,2-dimethylbut-1-en-1-yloxycarbonyl, 1,2-dimethylbut-2-en-1-yloxycarbonyl, 1,2-dimethylbut-3-en-1-yloxycarbonyl, 1,3-dimethylbut-1-en-1-yloxycarbonyl, 1,3-dimethylbut-2-en-1-yloxycarbonyl, 1,3-dimethylbut-3-en-1-yloxycarbonyl, 2,2-dimethylbut-3-en-1-yloxycarbonyl, 2,3-dimethylbut-1-en-1-yloxycarbonyl, 2,3-dimethylbut-2-en-1-yloxycarbonyl, 2,3-dimethylbut-3-en-1-yloxycarbonyl, 3,3-dimethylbut-1-en-1-yloxycarbonyl, 3,3-dimethylbut-2-en-1-yloxycarbonyl, 1-ethylbut-1-en-1-yloxycarbonyl, 1-ethylbut-2-en-1-yloxycarbonyl, 1-ethylbut-3-en-1-yloxycarbonyl, 2-ethylbut-1-en-1-yloxycarbonyl, 2-ethylbut-2-en-1-yloxycarbonyl, 2-ethylbut-3-en-1-yloxycarbonyl, 1,1,2-trimethylprop-2-en-1-yloxycarbonyl, 1-ethyl-1-methylprop-2-en-1-yloxycarbonyl, 1-ethyl-2-methylprop-1-en-1-yloxycarbonyl or 1-ethyl-2-methylprop-2-en-1-yloxycarbonyl, in particular prop-2-en-1-yloxycarbonyl;

($C_3$–$C_6$-alkenyloxy)carbonyl-$C_1$–$C_6$-alkyl: $C_1$–$C_6$-alkyl which is substituted by ($C_3$–$C_6$-alkenyloxy)carbonyl as mentioned above, preferably prop-2-en-1-yloxycarbonyl, e.g. prop-2-en-1-yl-oxycarbonylmethyl;

$C_3$–$C_6$-alkynyloxy)carbonyl: prop-1-yn-1-yloxycarbonyl, prop-2-yn-1-yloxycarbonyl, n-but-1-yn-1-yloxycarbonyl, n-but-1-yn-3-yloxycarbonyl, n-but-1-yn-4-yloxycarbonyl, n-but-2-yn-1-yloxycarbonyl, n-pent-1-yn-1-yloxycarbonyl, n-pent-1-yn-3-yloxycarbonyl, n-pent-1-yn-4-yloxycarbonyl, n-pent-1-yn-5-yloxycarbonyl, n-pent-2-yn-1-yloxycarbonyl, n-pent-2-yn-4-yloxycarbonyl, n-pent-2-yn-5-yloxycarbonyl, 3-methylbut-1-yn-3-yloxycarbonyl, 3-methylbut-1-yn-4-yloxycarbonyl, n-hex-1-yn-1-yloxycarbonyl, n-hex-1-yn-3-yloxycarbonyl, n-hex-1-yn-4-yloxycarbonyl, n-hex-1-yn-5-yloxycarbonyl, n-hex-1-yn-6-yloxycarbonyl, n-hex-2-yn-1-yloxycarbonyl, n-hex-2-yn-4-yloxycarbonyl, n-hex-2-yn-5-yloxycarbonyl, n-hex-2-yn-6-yloxycarbonyl, n-hex-3-yn-1-yloxycarbonyl, n-hex-3-yn-2-yloxycarbonyl, 3-methylpent-1-yn-1-yloxycarbonyl, 3-methylpent-1-yn-3-yloxycarbonyl, 3-methylpent-1-yn-4-yloxycarbonyl, 3-methylpent-1-yn-5-yloxycarbonyl, 4-methylpent-1-yn-1-yloxycarbonyl, 4-methylpent-2-yn-4-yloxycarbonyl or 4-methylpent-2-yn-5-yloxycarbonyl, in particular ethynyloxycarbonyl or prop-2-yn-1-yloxycarbonyl;

$C_3$–$C_6$-cycloalkyl: cyclopropyl, cyclobutyl, cyclopentyl or cyclohexyl;

$C_3$–$C_6$-cycloalkyl-$C_1$–$C_4$-alkyl: for example cyclopropylmethyl, cyclobutylmethyl, cyclopentylmethyl, cyclohexylmethyl, 1-(cyclopropyl) ethyl, 1-(cyclobutyl)ethyl, 1-(cyclopentyl)ethyl, 1-(cyclohexyl)ethyl, 2-(cyclopropyl)ethyl, 2-(cyclobutyl)ethyl, 2-(cyclopentyl)ethyl, 2-(cyclohexyl)-ethyl, 3-(cyclopropyl)propyl, 3-(cyclobutyl)propyl, 3-(cyclopentyl)propyl, 3-(cyclohexyl)propyl, 4-(cyclopropyl)butyl, 4-(cyclobutyl)butyl, 4-(cyclopentyl)butyl or 4-(cyclohexyl)butyl, in particular cyclopentylmethyl or cyclohexylmethyl;

$C_3$–$C_6$-cycloalkoxy: cyclopropyloxy, cyclobutyloxy, cyclopentyloxy or cyclohexyloxy;

$C_3$–$C_6$-cycloalkylthio: cyclopropylthio, cyclobutylthio, cyclopentylthio or cyclohexylthio.

4- to 7-membered aza heterocycles which, in addition to carbon ring members, may also comprise, as a ring member, an oxygen or sulfur atom, are, for example, azetidin-1-yl, pyrrolidin-1-yl, isoxazolidin-2-yl, isothiazolidin-2-yl, oxazolidin-3-yl, thiazolidin-3-yl, piperidin-1-yl, morpholin-1-yl, thiomorpholin-1-yl and azepin-1-yl.

With a view to the use of the 1-aryl-4-thiotriazines of the formula I according to the invention as herbicides, the variables preferably have the following meanings, in each case alone or in combination:

$R^1$ is hydrogen, amino or methyl, in particular methyl;

$R^2$ is hydrogen, amino or methyl, in particular methyl;

$R^3$ is hydrogen or fluorine, in particular fluorine;

$R^4$ is cyano or halogen, in particular
  a) cyano;
  b) chlorine;

Y is the methine group or, together with $R^5$, is a bridge >C—O—C($R^6$)=N—, in particular
  a) the methine group;
  b) together with $R^5$ a bridge >C—O—C($R^6$)=N—;

$R^5$ is
  1) on the one hand, hydrogen, nitro or halogen; on the other hand, $C_1$–$C_6$-alkyl or $C_1$–$C_6$-haloalkyl;
  2) on the one hand, $C_1$–$C_6$-alkoxy or $C_1$–$C_6$-alkylthio, it being possible for each of these two radicals, if desired, to have attached to it one of the following substituents: cyano, —CO—$R^8$, —CO—O$R^8$ or —CO—N($R^8$)—$R^9$, in particular methoxy, ethoxy, n-propyloxy, isopropoxy, methylthio, ethylthio, n-propylthio or isopropylthio, it being possible for each of these 8 radicals, if desired, to have attached to it a substituent —CO—O$R^{8'}$ especially preferably ($C_3$–$C_6$-alkenyloxy)carbonylmethoxy, ($C_3$–$C_6$-alkynyloxy)carbonylmethoxy, 1-[($C_3$–$C_6$-alkenyloxy)carbonyl]eth-1-yloxy, 1-[($C_3$–$C_6$-alkynyloxy)carbonyl]eth-1-yloxy, $C_1$–$C_4$-alkoxy-($C_1$–$C_4$-alkoxy)carbonylmethoxy, 1-[$C_1$–$C_4$-alkoxy-($C_1$–$C_4$-alkoxy)carbonyl]eth-1-yloxy, ($C_3$–$C_6$-alkenyloxy)carbonylmethylthio, ($C_3$–$C_6$-alkynyloxy)carbonylmethylthio, 1-[($C_3$–$C_6$-alkenyloxy)carbonyl]eth-1-ylthio, 1-[($C_3$–$C_6$-alkynyloxy)carbonyl]eth-1-ylthio, $C_1$–$C_4$-alkoxy-($C_1$–$C_4$-alkoxy)carbonylmethylthio or 1-[$C_1$–$C_4$-alkoxy-($C_1$–$C_4$-alkoxy)carbonyl]eth-1-ylthio;

on the other hand, $C_3$–$C_6$-cycloalkoxy, $C_3$–$C_6$-cycloalkylthio, $C_2$–$C_6$-alkenyloxy, $C_2$–$C_6$-alkenylthio, $C_2$–$C_6$-alkynyloxy or $C_2$–$C_6$-alkynylthio, it being possible for each of these 6 radicals, if desired, to have attached to it one of the following substituents: cyano, —CO—$R^8$, —CO—O$R^8$ or —CO—N($R^8$)—$R^9$, in particular cyclopentyloxy, cyclopentylthio, allyloxy, allylthio, propargyloxy or propargylthio;

3) on the one hand, —CO—$R^{11}$, —C($R^{11}$)=C($R^{15}$)—CO—$R^{16}$, —CH($R^{11}$)—CH($R^{15}$)—CO—$R^{16}$, —C($R^{10}$)=N—O$R^7$, —N($R^{21}$)—$R^{22}$ or —CO—N($R^{21}$)—$R^{22}$, in particular CHO, —CH=C($R^{15}$)—CO—$R^{16}$, —CH$_2$-CH($R^{15}$)—CO-$R^{16}$, —CH=N—O$R^7$, —C(CH$_3$)=N—O$R^7$, —N($R^{21}$)-$R^{22}$ or —CO—N($R^{21}$)—$R^{22}$;

on the other hand, —CO—O$R^{20}$;

$R^8$ is hydrogen, $C_3$–$C_6$-cycloalkyl, $C_3$–$C_6$-alkenyl, $C_3$–$C_6$-alkynyl, $C_3$–$C_6$-cycloalkyl-$C_1$–$C_4$-alkyl or $C_1$–$C_4$-alkoxy-$C_1$–$C_4$-alkyl, in particular $C_3$–$C_6$-alkenyl;

$R^{8'}$ is hydrogen, $C_1$–$C_6$-alkyl, $C_3$–$C_6$-cycloalkyl, $C_3$–$C_6$-alkenyl, $C_3$–$C_6$-alkynyl, $C_3$–$C_6$-cycloalkyl-$C_1$–$C_4$-alkyl or $C_1$–$C_4$-alkoxy-$C_1$–$C_4$-alkyl, in particular $C_1$–$C_6$-alkyl;

$R^9$ is hydrogen;

$R^{11}$ is hydrogen;

$R^{15}$ is hydrogen, halogen or $C_1$–$C_6$-alkyl, in particular hydrogen, chlorine, bromine or methyl, especially preferably chlorine;

$R^{20}$ is $C_3$–$C_6$-alkenyl, $C_3$–$C_6$-alkynyl, $C_1$–$C_4$-alkoxy-$C_1$–$C_4$-alkyl, ($C_3$–$C_6$-alkenyloxy)carbonylmethyl, ($C_3$–$C_6$-alkynyloxy)carbonylmethyl, 1-($C_3$–$C_6$-alkenyloxy)carbonyl-eth-1-yl, 1-($C_3$–$C_6$-alkynyloxy)carbonyl-eth-1-yl, $C_1$–$C_4$-alkoxy-($C_1$–$C_4$-alkoxy)carbonylmethyl, 1-[$C_1$–$C_4$-alkoxy-($C_1$–$C_4$-alkoxy)carbonyl]-eth-1-yl, 2-[($C_3$–$C_6$-alkenyloxy)carbonyl]-prop-2-yl, $C_3$–$C_6$-cycloalkyl or $C_3$–$C_6$-cycloalkyl-$C_1$–$C_4$-alkyl;

$R^{23}$ is hydrogen, $C_1$–$C_6$-alkyl, $C_3$–$C_6$-alkenyl or $C_3$–$C_6$-alkynyl, it being possible for the last-mentioned 3 groups to have attached to them in each case one of the following radicals:
$C_1$–$C_6$-alkoxy, ($C_1$–$C_6$-alkoxy)carbonyl or ($C_3$–$C_6$-alkenyloxy)carbonyl.

Very specially preferred are the 1-aryl-4-thiotriazines of the formula Ia (= I where $R^2$=methyl and Y=the methine group)

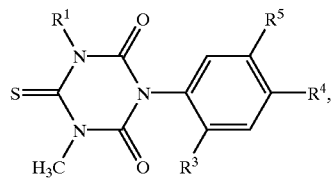

Ia in particular the compounds Ia.1 to Ia.720 which are listed in Table 1 below:

TABLE 1

| No.   | $R^1$ | $R^3$ | $R^4$ | $R^5$ |
|-------|-------|-------|-------|-------|
| Ia.1  | CH$_3$ | F | CN | OCH(CH$_3$)—CO—OCH$_3$ |
| Ia.2  | CH$_3$ | F | CN | OCH$_2$—C≡CH |

TABLE 1-continued

| No. | $R^1$ | $R^3$ | $R^4$ | $R^5$ |
|---|---|---|---|---|
| Ia.3 | $CH_3$ | F | CN | $OCH(CH_3)-C\equiv CH$ |
| Ia.4 | $CH_3$ | F | CN | $OCH(CH_3)-CO-OCH_2-CH_2-OCH_3$ |
| Ia.5 | $CH_3$ | F | CN | $CO-OCH_3$ |
| Ia.6 | $CH_3$ | F | CN | $CO-OCH(CH_3)-CO-OCH_3$ |
| Ia.7 | $CH_3$ | F | CN | $CO-OC(CH_3)_2-CO-OCH_3$ |
| Ia.8 | $CH_3$ | F | CN | $CO-OCH(CH_3)-CO-OCH_2-CH=CH_2$ |
| Ia.9 | $CH_3$ | F | CN | $CO-OC(CH_3)_2-CO-OCH_2-CH=CH_2$ |
| Ia.10 | $CH_3$ | F | CN | $C(N-OCH_3)-OCH_2-CO-OCH_3$ |
| Ia.11 | $CH_3$ | F | CN | $C(N-OCH_3)-OCH(CH_3)-CO-OCH_3$ |
| Ia.12 | $CH_3$ | F | CN | $C(N-OCH_3)-OCH_2-CO-O(phenyl)$ |
| Ia.13 | $CH_3$ | F | CN | $CH=C(Cl)-CO-OCH_3$ |
| Ia.14 | $CH_3$ | F | CN | $CH=C(CH_3)-CO-OCH_3$ |
| Ia.15 | $CH_3$ | F | CN | $CH=C(Cl)-CO-OC_2H_5$ |
| Ia.16 | $CH_3$ | F | CN | $CH=N-OCH_3$ |
| Ia.17 | $CH_3$ | F | CN | $CH=N-OC_2H_5$ |
| Ia.18 | $CH_3$ | F | CN | $CH=N-OCH_2-CH=CH_2$ |
| Ia.19 | $CH_3$ | F | CN | $NH-SO_2-CH_3$ |
| Ia.20 | $CH_3$ | F | CN | $NH-SO_2-C_2H_5$ |
| Ia.21 | $CH_3$ | F | Cl | $OCH(CH_3)-CO-OCH_3$ |
| Ia.22 | $CH_3$ | F | Cl | $OCH_2-C\equiv CH$ |
| Ia.23 | $CH_3$ | F | Cl | $OCH(CH_3)-C\equiv CH$ |
| Ia.24 | $CH_3$ | F | Cl | $OCH(CH_3)-CO-OCH_2-CH_2-OCH_3$ |
| Ia.25 | $CH_3$ | F | Cl | $CO-OCH_3$ |
| Ia.26 | $CH_3$ | F | Cl | $CO-OCH(CH_3)-CO-OCH_3$ |
| Ia.27 | $CH_3$ | F | Cl | $CO-OC(CH_3)_2-CO-OCH_3$ |
| Ia.28 | $CH_3$ | F | Cl | $CO-OCH(CH_3)-CO-OCH_2-CH=CH_2$ |
| Ia.29 | $CH_3$ | F | Cl | $CO-OC(CH_3)_2-CO-OCH_2-CH=CH_2$ |
| Ia.30 | $CH_3$ | F | Cl | $C(N-OCH_3)-OCH_2-CO-OCH_3$ |
| Ia.31 | $CH_3$ | F | Cl | $C(N-OCH_3)-OCH(CH_3)-CO-OCH_3$ |
| Ia.32 | $CH_3$ | F | Cl | $C(N-OCH_3)-OCH_2-CO-O(phenyl)$ |
| Ia.33 | $CH_3$ | F | Cl | $CH=C(Cl)-CO-OCH_3$ |
| Ia.34 | $CH_3$ | F | Cl | $CH=C(CH_3)-CO-OCH_3$ |
| Ia.35 | $CH_3$ | F | Cl | $CH=C(Cl)-CO-OC_2H_5$ |
| Ia.36 | $CH_3$ | F | Cl | $CH=N-OCH_3$ |
| Ia.37 | $CH_3$ | F | Cl | $CH=N-OC_2H_5$ |
| Ia.38 | $CH_3$ | F | Cl | $CH=N-OCH_2-CH=CH_2$ |
| Ia.39 | $CH_3$ | F | Cl | $NH-SO_2-CH_3$ |
| Ia.40 | $CH_3$ | F | Cl | $NH-SO_2-C_2H_5$ |
| Ia.41 | $CH_3$ | H | CN | $OCH(CH_3)-CO-OCH_3$ |
| Ia.42 | $CH_3$ | H | CN | $OCH_2-C\equiv CH$ |
| Ia.43 | $CH_3$ | H | CN | $OCH(CH_3)-C\equiv CH$ |
| Ia.44 | $CH_3$ | H | CN | $OCH(CH_3)-CO-OCH_2-CH_2-OCH_3$ |
| Ia.45 | $CH_3$ | H | CN | $CO-OCH_3$ |
| Ia.46 | $CH_3$ | H | CN | $CO-OCH(CH_3)-CO-OCH_3$ |
| Ia.47 | $CH_3$ | H | CN | $CO-OC(CH_3)_2-CO-OCH_3$ |
| Ia.48 | $CH_3$ | H | CN | $CO-OCH(CH_3)-CO-OCH_2-CH=CH_2$ |
| Ia.49 | $CH_3$ | H | CN | $CO-OC(CH_3)_2-CO-OCH_2-CH=CH_2$ |
| Ia.50 | $CH_3$ | H | CN | $C(N-OCH_3)-OCH_2-CO-OCH_3$ |
| Ia.51 | $CH_3$ | H | CN | $C(N-OCH_3)-OCH(CH_3)-CO-OCH_3$ |
| Ia.52 | $CH_3$ | H | CN | $C(N-OCH_3)-OCH_2-CO-O(phenyl)$ |
| Ia.53 | $CH_3$ | H | CN | $CH=C(Cl)-CO-OCH_3$ |
| Ia.54 | $CH_3$ | H | CN | $CH=C(CH_3)-CO-OCH_3$ |
| Ia.55 | $CH_3$ | H | CN | $CH=C(Cl)-CO-OC_2H_5$ |
| Ia.56 | $CH_3$ | H | CN | $CH=N-OCH_3$ |
| Ia.57 | $CH_3$ | H | CN | $CH=N-OC_2H_5$ |
| Ia.58 | $CH_3$ | H | CN | $CH=N-OCH_2-CH=CH_2$ |
| Ia.59 | $CH_3$ | H | CN | $NH-SO_2-CH_3$ |
| Ia.60 | $CH_3$ | H | CN | $NH-SO_2-C_2H_5$ |
| Ia.61 | $CH_3$ | H | Cl | $OCH(CH_3)-CO-OCH_3$ |
| Ia.62 | $CH_3$ | H | Cl | $OCH_2-C\equiv CH$ |
| Ia.63 | $CH_3$ | H | Cl | $OCH(CH_3)-C\equiv CH$ |
| Ia.64 | $CH_3$ | H | Cl | $OCH(CH_3)-CO-OCH_2-CH_2-OCH_3$ |
| Ia.65 | $CH_3$ | H | Cl | $CO-OCH_3$ |
| Ia.66 | $CH_3$ | H | Cl | $CO-OCH(CH_3)-CO-OCH_3$ |
| Ia.67 | $CH_3$ | H | Cl | $CO-OC(CH_3)_2-CO-OCH_3$ |
| Ia.68 | $CH_3$ | H | Cl | $CO-OCH(CH_3)-CO-OCH_2-CH=CH_2$ |
| Ia.69 | $CH_3$ | H | Cl | $CO-OC(CH_3)_2-CO-OCH_2-CH=CH_2$ |
| Ia.70 | $CH_3$ | H | Cl | $C(N-OCH_3)-OCH_2-CO-OCH_3$ |
| Ia.71 | $CH_3$ | H | Cl | $C(N-OCH_3)-OCH(CH_3)-CO-OCH_3$ |
| Ia.72 | $CH_3$ | H | Cl | $C(N-OCH_3)-OCH_2-CO-O(phenyl)$ |
| Ia.73 | $CH_3$ | H | Cl | $CH=C(Cl)-CO-OCH_3$ |
| Ia.74 | $CH_3$ | H | Cl | $CH=C(CH_3)-CO-OCH_3$ |
| Ia.75 | $CH_3$ | H | Cl | $CH=C(Cl)-CO-OC_2H_5$ |
| Ia.76 | $CH_3$ | H | Cl | $CH=N-OCH_3$ |
| Ia.77 | $CH_3$ | H | Cl | $CH=N-OC_2H_5$ |
| Ia.78 | $CH_3$ | H | Cl | $CH=N-OCH_2-CH=CH_2$ |
| Ia.79 | $CH_3$ | H | Cl | $NH-SO_2-CH_3$ |

TABLE 1-continued

| No. | $R^1$ | $R^3$ | $R^4$ | $R^5$ |
|---|---|---|---|---|
| Ia.80 | $CH_3$ | H | Cl | $NH-SO_2-C_2H_5$ |
| Ia.81 | $NH_2$ | F | CN | $OCH(CH_3)-CO-OCH_3$ |
| Ia.82 | $NH_2$ | F | CN | $OCH_2-C\equiv CH$ |
| Ia.83 | $NH_2$ | F | CN | $OCH(CH_3)-C\equiv CH$ |
| Ia.84 | $NH_2$ | F | CN | $OCH(CH_3)-CO-OCH_2-CH_2-OCH_3$ |
| Ia.85 | $NH_2$ | F | CN | $CO-OCH_3$ |
| Ia.86 | $NH_2$ | F | CN | $CO-OCH(CH_3)-CO-OCH_3$ |
| Ia.87 | $NH_2$ | F | CN | $CO-OC(CH_3)_2-CO-OCH_3$ |
| Ia.88 | $NH_2$ | F | CN | $CO-OCH(CH_3)-CO-OCH_2-CH=CH_2$ |
| Ia.89 | $NH_2$ | F | CN | $CO-OC(CH_3)_2-CO-OCH_2-CH=CH_2$ |
| Ia.90 | $NH_2$ | F | CN | $C(N-OCH_3)-OCH_2-CO-OCH_3$ |
| Ia.91 | $NH_2$ | F | CN | $C(N-OCH_3)-OCH(CH_3)-CO-OCH_3$ |
| Ia.92 | $NH_2$ | F | CN | $C(N-OCH_3)-OCH_2-CO-O(phenyl)$ |
| Ia.93 | $NH_2$ | F | CN | $CH=C(Cl)-CO-OCH_3$ |
| Ia.94 | $NH_2$ | F | CN | $CH=C(CH_3)-CO-OCH_3$ |
| Ia.95 | $NH_2$ | F | CN | $CH=C(Cl)-CO-OC_2H_5$ |
| Ia.96 | $NH_2$ | F | CN | $CH=N-OCH_3$ |
| Ia.97 | $NH_2$ | F | CN | $CH=N-OC_2H_5$ |
| Ia.98 | $NH_2$ | F | CN | $CH=N-OCH_2-CH=CH_2$ |
| Ia.99 | $NH_2$ | F | CN | $NH-SO_2-CH_3$ |
| Ia.100 | $NH_2$ | F | CN | $NH-SO_2-C_2H_5$ |
| Ia.101 | $NH_2$ | F | Cl | $OCH(CH_3)-CO-OCH_3$ |
| Ia.102 | $NH_2$ | F | Cl | $OCH_2-C\equiv CH$ |
| Ia.103 | $NH_2$ | F | Cl | $OCH(CH_3)-C\equiv CH$ |
| Ia.104 | $NH_2$ | F | Cl | $OCH(CH_3)-CO-OCH_2-CH_2-OCH_3$ |
| Ia.105 | $NH_2$ | F | Cl | $CO-OCH_3$ |
| Ia.106 | $NH_2$ | F | Cl | $CO-OCH(CH_3)-CO-OCH_3$ |
| Ia.107 | $NH_2$ | F | Cl | $CO-OC(CH_3)_2-CO-OCH_3$ |
| Ia.108 | $NH_2$ | F | Cl | $CO-OCH(CH_3)-CO-OCH_2-CH=CH_2$ |
| Ia.109 | $NH_2$ | F | Cl | $CO-OC(CH_3)_2-CO-OCH_2-CH=CH_2$ |
| Ia.110 | $NH_2$ | F | Cl | $C(N-OCH_3)-OCH_2-CO-OCH_3$ |
| Ia.111 | $NH_2$ | F | Cl | $C(N-OCH_3)-OCH(CH_3)-CO-OCH_3$ |
| Ia.112 | $NH_2$ | F | Cl | $C(N-OCH_3)-OCH_2-CO-O(phenyl)$ |
| Ia.113 | $NH_2$ | F | Cl | $CH=C(Cl)-CO-OCH_3$ |
| Ia.114 | $NH_2$ | F | Cl | $CH=C(CH_3)-CO-OCH_3$ |
| Ia.115 | $NH_2$ | F | Cl | $CH=C(Cl)-CO-OC_2H_5$ |
| Ia.116 | $NH_2$ | F | Cl | $CH=N-OCH_3$ |
| Ia.117 | $NH_2$ | F | Cl | $CH=N-OC_2H_5$ |
| Ia.118 | $NH_2$ | F | Cl | $CH=N-OCH_2-CH=CH_2$ |
| Ia.119 | $NH_2$ | F | Cl | $NH-SO_2-CH_3$ |
| Ia.120 | $NH_2$ | F | Cl | $NH-SO_2-C_2H_5$ |
| Ia.121 | $NH_2$ | H | CN | $OCH(CH_3)-CO-OCH_3$ |
| Ia.122 | $NH_2$ | H | CN | $OCH_2-C\equiv CH$ |
| Ia.123 | $NH_2$ | H | CN | $OCH(CH_3)-C\equiv CH$ |
| Ia.124 | $NH_2$ | H | CN | $OCH(CH_3)-CO-OCH_2-CH_2-OCH_3$ |
| Ia.125 | $NH_2$ | H | CN | $CO-OCH_3$ |
| Ia.126 | $NH_2$ | H | CN | $CO-OCH(CH_3)-CO-OCH_3$ |
| Ia.127 | $NH_2$ | H | CN | $CO-OC(CH_3)_2-CO-OCH_3$ |
| Ia.128 | $NH_2$ | H | CN | $CO-OCH(CH_3)-CO-OCH_2-CH=CH_2$ |
| Ia.129 | $NH_2$ | H | CN | $CO-OC(CH_3)_2-CO-OCH_2-CH=CH_2$ |
| Ia.130 | $NH_2$ | H | CN | $C(N-OCH_3)-OCH_2-CO-OCH_3$ |
| Ia.131 | $NH_2$ | H | CN | $C(N-OCH_3)-OCH(CH_3)-CO-OCH_3$ |
| Ia.132 | $NH_2$ | H | CN | $C(N-OCH_3)-OCH_2-CO-O(phenyl)$ |
| Ia.133 | $NH_2$ | H | CN | $CH=C(Cl)-CO-OCH_3$ |
| Ia.134 | $NH_2$ | H | CN | $CH=C(CH_3)-CO-OCH_3$ |
| Ia.135 | $NH_2$ | H | CN | $CH=C(Cl)-CO-OC_2H_5$ |
| Ia.136 | $NH_2$ | H | CN | $CH=N-OCH_3$ |
| Ia.137 | $NH_2$ | H | CN | $CH=N-OC_2H_5$ |
| Ia.138 | $NH_2$ | H | CN | $CH=N-OCH_2-CH=CH_2$ |
| Ia.139 | $NH_2$ | H | CN | $NH-SO_2-CH_3$ |
| Ia.140 | $NH_2$ | H | CN | $NH-SO_2-C_2H_5$ |
| Ia.141 | $NH_2$ | H | Cl | $OCH(CH_3)-CO-OCH_3$ |
| Ia.142 | $NH_2$ | H | Cl | $OCH_2-C\equiv CH$ |
| Ia.143 | $NH_2$ | H | Cl | $OCH(CH_3)-C\equiv CH$ |
| Ia.144 | $NH_2$ | H | Cl | $OCH(CH_3)-CO-OCH_2-CH_2-OCH_3$ |
| Ia.145 | $NH_2$ | H | Cl | $CO-OCH_3$ |
| Ia.146 | $NH_2$ | H | Cl | $CO-OCH(CH_3)-CO-OCH_3$ |
| Ia.147 | $NH_2$ | H | Cl | $CO-OC(CH_3)_2-CO-OCH_3$ |
| Ia.148 | $NH_2$ | H | Cl | $CO-OCH(CH_3)-CO-OCH_2-CH=CH_2$ |
| Ia.149 | $NH_2$ | H | Cl | $CO-OC(CH_3)_2-CO-OCH_2-CH=CH_2$ |
| Ia.150 | $NH_2$ | H | Cl | $C(N-OCH_3)-OCH_2-CO-OCH_3$ |
| Ia.151 | $NH_2$ | H | Cl | $C(N-OCH_3)-OCH(CH_3)-CO-OCH_3$ |
| Ia.152 | $NH_2$ | H | Cl | $C(N-OCH_3)-OCH_2-CO-O(phenyl)$ |
| Ia.153 | $NH_2$ | H | Cl | $CH=C(Cl)-CO-OCH_3$ |
| Ia.154 | $NH_2$ | H | Cl | $CH=C(CH_3)-CO-OCH_3$ |
| Ia.155 | $NH_2$ | H | Cl | $CH=C(Cl)-CO-OC_2H_5$ |
| Ia.156 | $NH_2$ | H | Cl | $CH=N-OCH_3$ |

TABLE 1-continued

| No. | $R^1$ | $R^3$ | $R^4$ | $R^5$ |
|---|---|---|---|---|
| Ia.157 | NH$_2$ | H | Cl | CH=N—OC$_2$H$_5$ |
| Ia.158 | NH$_2$ | H | Cl | CH=N—OCH$_2$—CH=CH$_2$ |
| Ia.159 | NH$_2$ | H | Cl | NH—SO$_2$—CH$_3$ |
| Ia.160 | NH$_2$ | H | Cl | NH—SO$_2$—C$_2$H$_5$ |
| Ia.161 | CH$_3$ | F | Cl | OCH$_3$ |
| Ia.162 | CH$_3$ | F | Cl | OCH(CH$_3$)$_2$ |
| Ia.163 | CH$_3$ | F | Cl | OCH$_2$—CH=CH$_2$ |
| Ia.164 | CH$_3$ | F | Cl | O-cyclopentyl |
| Ia.165 | CH$_3$ | F | Cl | OCH$_2$—CO—OCH$_3$ |
| Ia.166 | CH$_3$ | F | Cl | OCH$_2$—CO—OCH$_2$—CH=CH$_2$ |
| Ia.167 | CH$_3$ | F | Cl | OCH$_2$—CO—OCH$_2$—CH=CH—CH$_3$ |
| Ia.168 | CH$_3$ | F | Cl | OCH$_2$—CO—OCH$_2$—CH$_2$—CH=CH$_2$ |
| Ia.169 | CH$_3$ | F | Cl | OCH$_2$—CO—OCH$_2$—CH=C(CH$_3$)$_2$ |
| Ia.170 | CH$_3$ | F | Cl | OCH$_2$—CO—OCH$_2$—C≡CH |
| Ia.171 | CH$_3$ | F | Cl | OCH$_2$—CO—OCH$_2$CH$_2$—C≡CH |
| Ia.172 | CH$_3$ | F | Cl | OCH$_2$—CO—O-cyclopentyl |
| Ia.173 | CH$_3$ | F | Cl | OCH$_2$—CO—OCH$_2$CH$_2$—OCH$_3$ |
| Ia.174 | CH$_3$ | F | Cl | OCH$_2$—CO—OCH$_2$CH$_2$—OC$_2$H$_5$ |
| Ia.175 | CH$_3$ | F | Cl | OCH$_2$—CO—OCH$_2$-cyclopropyl |
| Ia.176 | CH$_3$ | F | Cl | OCH$_2$—CO—OCH$_2$-cyclobutyl |
| Ia.177 | CH$_3$ | F | Cl | OCH$_2$—CO—OCH$_2$-cyclopentyl |
| Ia.178 | CH$_3$ | F | Cl | OCH$_2$—CO—OCH$_2$-cyclohexyl |
| Ia.179 | CH$_3$ | F | Cl | OCH$_2$—CO—NH—CH$_3$ |
| Ia.180 | CH$_3$ | F | Cl | OCH$_2$—CO—N(CH$_3$)$_2$ |
| Ia.181 | CH$_3$ | F | Cl | OCH(CH$_3$)—CO—OCH$_2$—CH=CH$_2$ |
| Ia.182 | CH$_3$ | F | Cl | OCH(CH$_3$)—CO—OCH$_2$—CH=CH—CH$_3$ |
| Ia.183 | CH$_3$ | F | Cl | OCH(CH$_3$)—CO—OCH$_2$CH$_2$—CH=CH$_2$ |
| Ia.184 | CH$_3$ | F | Cl | OCH(CH$_3$)—CO—OCH$_2$—CH=C(CH$_3$)$_2$ |
| Ia.185 | CH$_3$ | F | Cl | OCH(CH$_3$)—CO—OCH$_2$—C≡CH |
| Ia.186 | CH$_3$ | F | Cl | OCH(CH$_3$)—CO—O—CH$_2$CH$_2$—C≡CH |
| Ia.187 | CH$_3$ | F | Cl | OCH(CH$_3$)—CO—O-cyclopentyl |
| Ia.188 | CH$_3$ | F | Cl | OCH(CH$_3$)—CO—OCH$_2$CH$_2$—OC$_2$H$_5$ |
| Ia.189 | CH$_3$ | F | Cl | OCH(CH$_3$)—CO—OCH$_2$-cyclopropyl |
| Ia.190 | CH$_3$ | F | Cl | OCH(CH$_3$)—CO—OCH$_2$-cyclobutyl |
| Ia.191 | CH$_3$ | F | Cl | OCH(CH$_3$)—CO—OCH$_2$-cyclopentyl |
| Ia.192 | CH$_3$ | F | Cl | OCH(CH$_3$)—CO—OCH$_2$-cyclohexyl |
| Ia.193 | CH$_3$ | F | Cl | OCH(CH$_3$)—CO—NH—CH$_3$ |
| Ia.194 | CH$_3$ | F | Cl | OCH(CH$_3$)—CO—N(CH$_3$)$_2$ |
| Ia.195 | CH$_3$ | F | Cl | OC(CH$_3$)$_2$—CO—OCH$_3$ |
| Ia.196 | CH$_3$ | F | Cl | OC(CH$_3$)$_2$—CO—OCH$_2$—CH=CH$_2$ |
| Ia.197 | CH$_3$ | F | Cl | OC(CH$_3$)$_2$—CO—OCH$_2$—C≡CH |
| Ia.198 | CH$_3$ | F | Cl | OC(CH$_3$)$_2$—CO—O-cyclopentyl |
| Ia.199 | CH$_3$ | F | Cl | OC(CH$_3$)$_2$—CO—OCH$_2$CH$_2$—OCH$_3$ |
| Ia.200 | CH$_3$ | F | Cl | COOH |
| Ia.201 | CH$_3$ | F | Cl | CO—OCH(CH$_3$)$_2$ |
| Ia.202 | CH$_3$ | F | Cl | CO—OCH$_2$—CH=CH$_2$ |
| Ia.203 | CH$_3$ | F | Cl | CO—OCH$_2$—C≡CH |
| Ia.204 | CH$_3$ | F | Cl | CO—O-cyclopentyl |
| Ia.205 | CH$_3$ | F | Cl | CO—OCH$_2$—CO—OCH$_3$ |
| Ia.206 | CH$_3$ | F | Cl | CO—OCH$_2$—CO—OCH$_2$—CH=CH$_2$ |
| Ia.207 | CH$_3$ | F | Cl | CO—OCH$_2$CO—OCH$_2$—C≡CH |
| Ia.208 | CH$_3$ | F | Cl | CO—OCH$_2$CO—OCH$_2$CH$_2$—OCH$_3$ |
| Ia.209 | CH$_3$ | F | Cl | CO—OCH(CH$_3$)—CO—OCH$_2$—C≡CH |
| Ia.210 | CH$_3$ | F | Cl | CO—OCH(CH$_3$)—CO—OCH$_2$CH$_2$—OCH$_3$ |
| Ia.211 | CH$_3$ | F | Cl | CO—OC(CH$_3$)$_2$—CO—OCH$_2$—C≡CH |
| Ia.212 | CH$_3$ | F | Cl | CO—OC(CH$_3$)$_2$—CO—OCH$_2$CH$_2$—OCH$_3$ |
| Ia.213 | CH$_3$ | F | Cl | CO—NH—CH$_2$—CO—OCH$_3$ |
| Ia.214 | CH$_3$ | F | Cl | CO—NH—CH$_2$—CO—OCH$_2$—CH=CH$_2$ |
| Ia.215 | CH$_3$ | F | Cl | CO—NH—CH$_2$—CO—OCH$_2$CH$_2$—OCH$_3$ |
| Ia.216 | CH$_3$ | F | Cl | CO—NH—CH(CH$_3$)—CO—OCH$_3$ |
| Ia.217 | CH$_3$ | F | Cl | CO—NH—CH(CH$_3$)—CO—OCH$_2$—CH=CH$_2$ |
| Ia.218 | CH$_3$ | F | Cl | CO—NH—CH(CH$_3$)—CO—OCH$_2$CH$_2$—OCH$_3$ |
| Ia.219 | CH$_3$ | F | Cl | CO—N(CH$_3$)—CH$_2$—CO—OCH$_3$ |
| Ia.220 | CH$_3$ | F | Cl | CO—N(CH$_3$)—CH$_2$—CO—OCH$_2$—CH=CH$_2$ |
| Ia.221 | CH$_3$ | F | Cl | CO—N(CH$_3$)—CH$_2$—CO—OCH$_2$CH$_2$—OCH$_3$ |
| Ia.222 | CH$_3$ | F | Cl | CO—N(CH$_3$)—CH(CH$_3$)COO—CH$_3$ |
| Ia.223 | CH$_3$ | F | Cl | CO—N(CH$_3$)—CH(CH$_3$)COO—CH$_2$CH=CH$_2$ |
| Ia.224 | CH$_3$ | F | Cl | CO—N(CH$_3$)—CH(CH$_3$)COO—CH$_2$CH$_2$OCH$_3$ |
| Ia.225 | CH$_3$ | F | Cl | CH=C(Cl)—CO—OCH$_2$—CH=CH$_2$ |
| Ia.226 | CH$_3$ | F | Cl | CH=C(Cl)—CO—OCH$_2$—C≡CH |
| Ia.227 | CH$_3$ | F | Cl | CH=C(Cl)—CO—OCH$_2$—CO—OCH$_3$ |
| Ia.228 | CH$_3$ | F | Cl | CH=C(Cl)—CO—OCH(CH$_3$)—CO—OCH$_3$ |
| Ia.229 | CH$_3$ | F | Cl | CH=C(Cl)—CO—N(CH$_3$)—CH$_2$—CO—OCH$_3$ |
| Ia.230 | CH$_3$ | F | Cl | CH=C(Cl)—CO—NH—CH(CH$_3$)—CO—OCH$_3$ |
| Ia.231 | CH$_3$ | F | CN | OCH$_3$ |
| Ia.232 | CH$_3$ | F | CN | OCH(CH$_3$)$_2$ |
| Ia.233 | CH$_3$ | F | CN | O—CH$_2$CH=CH$_2$ |

TABLE 1-continued

| No. | R$^1$ | R$^3$ | R$^4$ | R$^5$ |
|---|---|---|---|---|
| Ia.234 | CH$_3$ | F | CN | O-cyclopentyl |
| Ia.235 | CH$_3$ | F | CN | OCH$_2$—CO—OCH$_3$ |
| Ia.236 | CH$_3$ | F | CN | OCH$_2$—CO—OCH$_2$—CH=CH$_2$ |
| Ia.237 | CH$_3$ | F | CN | OCH$_2$—CO—OCH$_2$CH=CH—CH$_3$ |
| Ia.238 | CH$_3$ | F | CN | OCH$_2$—CO—OCH$_2$CH$_2$—CH=CH$_2$ |
| Ia.239 | CH$_3$ | F | CN | OCH$_2$—CO—OCH$_2$—CH=C(CH$_3$)$_2$ |
| Ia.240 | CH$_3$ | F | CN | OCH$_2$—CO—OCH$_2$—C≡CH |
| Ia.241 | CH$_3$ | F | CN | OCH$_2$—CO—OCH$_2$CH$_2$—C≡CH |
| Ia.242 | CH$_3$ | F | CN | OCH$_2$—CO—O-cyclopentyl |
| Ia.243 | CH$_3$ | F | CN | OCH$_2$—CO—OCH$_2$CH$_2$—OCH$_3$ |
| Ia.244 | CH$_3$ | F | CN | OCH$_2$—CO—OCH$_2$CH$_2$—OC$_2$H$_5$ |
| Ia.245 | CH$_3$ | F | CN | OCH$_2$—CO—OCH$_2$-cyclopropyl |
| Ia.246 | CH$_3$ | F | CN | OCH$_2$—CO—OCH$_2$-cyclobutyl |
| Ia.247 | CH$_3$ | F | CN | OCH$_2$—CO—OCH$_2$-cyclopentyl |
| Ia.248 | CH$_3$ | F | CN | OCH$_2$—CO—OCH$_2$-cyclohexyl |
| Ia.249 | CH$_3$ | F | CN | OCH$_2$—CO—NH—CH$_3$ |
| Ia.250 | CH$_3$ | F | CN | OCH$_2$—CO—N(CH$_3$)$_2$ |
| Ia.251 | CH$_3$ | F | CN | OCH(CH$_3$)—CO—OCH$_2$—CH=CH$_2$ |
| Ia.252 | CH$_3$ | F | CN | OCH(CH$_3$)—CO—OCH$_2$—CH=CH—CH$_3$ |
| Ia.253 | CH$_3$ | F | CN | OCH(CH$_3$)—CO—OCH$_2$CH$_2$—CH=CH$_2$ |
| Ia.254 | CH$_3$ | F | CN | OCH(CH$_3$)—CO—OCH$_2$—CH=C(CH$_3$)$_2$ |
| Ia.255 | CH$_3$ | F | CN | OCH(CH$_3$)—CO—OCH$_2$—C≡CH |
| Ia.256 | CH$_3$ | F | CN | OCH(CH$_3$)—CO—OCH$_2$CH$_2$—C≡CH |
| Ia.257 | CH$_3$ | F | CN | OCH(CH$_3$)—CO—O-cyclopentyl |
| Ia.258 | CH$_3$ | F | CN | OCH(CH$_3$)—CO—OCH$_2$CH$_2$—OC$_2$H$_5$ |
| Ia.259 | CH$_3$ | F | CN | OCH(CH$_3$)—CO—OCH$_2$-cyclopropyl |
| Ia.260 | CH$_3$ | F | CN | OCH(CH$_3$)—CO—OCH$_2$-cyclobutyl |
| Ia.261 | CH$_3$ | F | CN | OCH(CH$_3$)—CO—OCH$_2$-cyclopentyl |
| Ia.262 | CH$_3$ | F | CN | OCH(CH$_3$)—CO—OCH$_2$-cyclohexyl |
| Ia.263 | CH$_3$ | F | CN | OCH(CH$_3$)—CO—NH—CH$_3$ |
| Ia.264 | CH$_3$ | F | CN | OCH(CH$_3$)—CO—N(CH$_3$)$_2$ |
| Ia.265 | CH$_3$ | F | CN | OC(CH$_3$)$_2$—CO—OCH$_3$ |
| Ia.266 | CH$_3$ | F | CN | OC(CH$_3$)$_2$—CO—OCH$_2$—CH=CH$_2$ |
| Ia.267 | CH$_3$ | F | CN | OC(CH$_3$)$_2$—CO—OCH$_2$—C≡CH |
| Ia.268 | CH$_3$ | F | CN | OC(CH$_3$)$_2$—CO—O-cyclopentyl |
| Ia.269 | CH$_3$ | F | CN | OC(CH$_3$)$_2$—CO—OCH$_2$CH$_2$—OCH$_3$ |
| Ia.270 | CH$_3$ | F | CN | COOH |
| Ia.271 | CH$_3$ | F | CN | CO—OCH(CH$_3$)$_2$ |
| Ia.272 | CH$_3$ | F | CN | CO—OCH$_2$—CH=CH$_2$ |
| Ia.273 | CH$_3$ | F | CN | CO—OCH$_2$—C≡CH |
| Ia.274 | CH$_3$ | F | CN | CO—O-cyclopentyl |
| Ia.275 | CH$_3$ | F | CN | CO—OCH$_2$—CO—OCH$_3$ |
| Ia.276 | CH$_3$ | F | CN | CO—OCH$_2$—CO—OCH$_2$—CH=CH$_2$ |
| Ia.277 | CH$_3$ | F | CN | CO—OCH$_2$—CO—OCH$_2$—C≡CH |
| Ia.278 | CH$_3$ | F | CN | CO—OCH$_2$—CO—OCH$_2$CH$_2$—OCH$_3$ |
| Ia.279 | CH$_3$ | F | CN | CO—OCH(CH$_3$)—CO—OCH$_2$—C≡CH |
| Ia.280 | CH$_3$ | F | CN | CO—OCH(CH$_3$)—CO—OCH$_2$CH$_2$—OCH$_3$ |
| Ia.281 | CH$_3$ | F | CN | CO—OC(CH$_3$)$_2$—CO—OCH$_2$—C≡CH |
| Ia.282 | CH$_3$ | F | CN | CO—OC(CH$_3$)$_2$—CO—OCH$_2$CH$_2$—OCH$_3$ |
| Ia.283 | CH$_3$ | F | CN | CO—NH—CH$_2$—CO—OCH$_3$ |
| Ia.284 | CH$_3$ | F | CN | CO—NH—CH$_2$—CO—OCH$_2$—CH=CH$_2$ |
| Ia.285 | CH$_3$ | F | CN | CO—NH—CH$_2$—CO—OCH$_2$CH$_2$—OCH$_3$ |
| Ia.286 | CH$_3$ | F | CN | CO—NH—CH(CH$_3$)—CO—OCH$_3$ |
| Ia.287 | CH$_3$ | F | CN | CO—NH—CH(CH$_3$)—CO—OCH$_2$—CH=CH$_2$ |
| Ia.288 | CH$_3$ | F | CN | CO—NH—CH(CH$_3$)—CO—OCH$_2$CH$_2$—OCH$_3$ |
| Ia.289 | CH$_3$ | F | CN | CO—N(CH$_3$)—CH$_2$—CO—OCH$_3$ |
| Ia.290 | CH$_3$ | F | CN | CO—N(CH$_3$)—CH$_2$—CO—OCH$_2$—CH=CH$_2$ |
| Ia.291 | CH$_3$ | F | CN | CO—N(CH$_3$)—CH$_2$—CO—OCH$_2$CH$_2$—OCH$_3$ |
| Ia.292 | CH$_3$ | F | CN | CO—N(CH$_3$)—CH(CH$_3$)—CO—OCH$_3$ |
| Ia.293 | CH$_3$ | F | CN | CO—N(CH$_3$)—CH(CH$_3$)—CO—OCH$_2$—CH=CH$_2$ |
| Ia.294 | CH$_3$ | F | CN | CO—N(CH$_3$)—CH(CH$_3$)—CO—OCH$_2$CH$_2$—OCH$_3$ |
| Ia.295 | CH$_3$ | F | CN | CH=C(Cl)—CO—OCH$_2$—CH=CH$_2$ |
| Ia.296 | CH$_3$ | F | CN | CH=C(Cl)—CO—OCH$_2$—C≡CH |
| Ia.297 | CH$_3$ | F | CN | CH=C(Cl)—CO—OCH$_2$—CO—OCH$_3$ |
| Ia.298 | CH$_3$ | F | CN | CH=C(Cl)—CO—OCH(CH$_3$)—CO—OCH$_3$ |
| Ia.299 | CH$_3$ | F | CN | CH=C(Cl)—CO—N(CH$_3$)—CH$_2$—CO—OCH$_3$ |
| Ia.300 | CH$_3$ | F | CN | CH=C(Cl)—CO—NH—CH(CH$_3$)—CO—OCH$_3$ |
| Ia.301 | CH$_3$ | H | Cl | OCH$_3$ |
| Ia.302 | CH$_3$ | H | Cl | OCH(CH$_3$)$_2$ |
| Ia.303 | CH$_3$ | H | Cl | O—CH$_2$—CH=CH$_2$ |
| Ia.304 | CH$_3$ | H | Cl | O-cyclopentyl |
| Ia.305 | CH$_3$ | H | Cl | OCH$_2$—CO—OCH$_3$ |
| Ia.306 | CH$_3$ | H | Cl | OCH$_2$—CO—OCH$_2$—CH=CH$_2$ |
| Ia.307 | CH$_3$ | H | Cl | OCH$_2$—CO—OCH$_2$—CH=CH—CH$_3$ |
| Ia.308 | CH$_3$ | H | Cl | OCH$_2$—CO—OCH$_2$CH$_2$—CH=CH$_2$ |
| Ia.309 | CH$_3$ | H | Cl | OCH$_2$—CO—OCH$_2$—CH=C(CH$_3$)$_2$ |
| Ia.310 | CH$_3$ | H | Cl | OCH$_2$—CO—OCH$_2$—C≡CH |

TABLE 1-continued

| No. | R¹ | R³ | R⁴ | R⁵ |
|---|---|---|---|---|
| Ia.311 | CH₃ | H | Cl | OCH₂—CO—OCH₂CH₂—C≡CH |
| Ia.312 | CH₃ | H | Cl | OCH₂—CO—O-cyclopentyl |
| Ia.313 | CH₃ | H | Cl | OCH₂—CO—OCH₂CH₂—OCH₃ |
| Ia.314 | CH₃ | H | Cl | OCH₂—CO—OCH₂CH₂—OC₂H₅ |
| Ia.315 | CH₃ | H | Cl | OCH₂—CO—OCH₂-cyclopropyl |
| Ia.316 | CH₃ | H | Cl | OCH₂—CO—OCH₂-cyclobutyl |
| Ia.317 | CH₃ | H | Cl | OCH₂—CO—OCH₂-cyclopentyl |
| Ia.318 | CH₃ | H | Cl | OCH₂—CO—OCH₂-cyclohexyl |
| Ia.319 | CH₃ | H | Cl | OCH₂—CO—NH—CH₃ |
| Ia.320 | CH₃ | H | Cl | OCH₂—CO—N(CH₃)₂ |
| Ia.321 | CH₃ | H | Cl | OCH(CH₃)—CO—OCH₂—CH=CH₂ |
| Ia.322 | CH₃ | H | Cl | OCH(CH₃)—CO—OCH₂—CH=CH—CH₃ |
| Ia.323 | CH₃ | H | Cl | OCH(CH₃)—CO—OCH₂CH₂—CH=CH₂ |
| Ia.324 | CH₃ | H | Cl | OCH(CH₃)—CO—OCH₂—CH=C(CH₃)₂ |
| Ia.325 | CH₃ | H | Cl | OCH(CH₃)—CO—OCH₂—C≡CH |
| Ia.326 | CH₃ | H | Cl | OCH(CH₃)—CO—OCH₂CH₂—C≡CH |
| Ia.327 | CH₃ | H | Cl | OCH(CH₃)—CO—O-cyclopentyl |
| Ia.328 | CH₃ | H | Cl | OCH(CH₃)—CO—OCH₂CH₂—OC₂H₅ |
| Ia.329 | CH₃ | H | Cl | OCH(CH₃)—CO—OCH₂-cyclopropyl |
| Ia.330 | CH₃ | H | Cl | OCH(CH₃)—CO—OCH₂-cyclobutyl |
| Ia.331 | CH₃ | H | Cl | OCH(CH₃)—CO—OCH₂-cyclopentyl |
| Ia.332 | CH₃ | H | Cl | OCH(CH₃)—CO—OCH₂-cyclohexyl |
| Ia.333 | CH₃ | H | Cl | OCH(CH₃)—CO—NH—CH₃ |
| Ia.334 | CH₃ | H | Cl | OCH(CH₃)—CO—N(CH₃)₂ |
| Ia.335 | CH₃ | H | Cl | OC(CH₃)₂—CO—OCH₃ |
| Ia.336 | CH₃ | H | Cl | OC(CH₃)₂—CO—OCH₂—CH=CH₂ |
| Ia.337 | CH₃ | H | Cl | OC(CH₃)₂—CO—OCH₂—C≡CH |
| Ia.338 | CH₃ | H | Cl | OC(CH₃)₂—CO—O-cyclopentyl |
| Ia.339 | CH₃ | H | Cl | OC(CH₃)₂—CO—OCH₂CH₂—OCH₃ |
| Ia.340 | CH₃ | H | Cl | COOH |
| Ia.341 | CH₃ | H | Cl | CO—OCH(CH₃)₂ |
| Ia.342 | CH₃ | H | Cl | CO—OCH₂—CH=CH₂ |
| Ia.343 | CH₃ | H | Cl | CO—OCH₂—C≡CH |
| Ia.344 | CH₃ | H | Cl | CO—O-cyclopentyl |
| Ia.345 | CH₃ | H | Cl | CO—OCH₂—CO—OCH₃ |
| Ia.346 | CH₃ | H | Cl | CO—OCH₂—CO—OCH₂—CH=CH₂ |
| Ia.347 | CH₃ | H | Cl | CO—OCH₂—CO—OCH₂—C≡CH |
| Ia.348 | CH₃ | H | Cl | CO—OCH₂—CO—OCH₂CH₂—OCH₃ |
| Ia.349 | CH₃ | H | Cl | CO—OCH(CH₃)—CO—OCH₂—C≡CH |
| Ia.350 | CH₃ | H | Cl | CO—OCH(CH₃)—CO—OCH₂CH₂—OCH₃ |
| Ia.351 | CH₃ | H | Cl | CO—OC(CH₃)₂—CO—OCH₂—C≡CH |
| Ia.352 | CH₃ | H | Cl | CO—OC(CH₃)₂—CO—OCH₂CH₂—OCH₃ |
| Ia.353 | CH₃ | H | Cl | CO—NH—CH₂—CO—OCH₃ |
| Ia.354 | CH₃ | H | Cl | CO—NH—CH₂—CO—OCH₂—CH=CH₂ |
| Ia.355 | CH₃ | H | Cl | CO—NH—CH₂—CO—OCH₂CH₂—OCH₃ |
| Ia.356 | CH₃ | H | Cl | CO—NH—CH(CH₃)—CO—OCH₃ |
| Ia.357 | CH₃ | H | Cl | CO—NH—CH(CH₃)—CO—OCH₂—CH=CH₂ |
| Ia.358 | CH₃ | H | Cl | CO—NH—CH(CH₃)—CO—OCH₂CH₂—OCH₃ |
| Ia.359 | CH₃ | H | Cl | CO—N(CH₃)—CH₂—CO—OCH₃ |
| Ia.360 | CH₃ | H | Cl | CO—N(CH₃)—CH₂—CO—OCH₂—CH=CH₂ |
| Ia.361 | CH₃ | H | Cl | CO—N(CH₃)—CH₂—CO—OCH₂CH₂—OCH₃ |
| Ia.362 | CH₃ | H | Cl | CO—N(CH₃)—CH(CH₃)—CO—OCH₃ |
| Ia.363 | CH₃ | H | Cl | CO—N(CH₃)—CH(CH₃)—CO—OCH₂—CH=CH₂ |
| Ia.364 | CH₃ | H | Cl | CO—N(CH₃)—CH(CH₃)—CO—OCH₂CH₂—OCH₃ |
| Ia.365 | CH₃ | H | Cl | CH=C(Cl)—CO—OCH₂—CH=CH₂ |
| Ia.366 | CH₃ | H | Cl | CH=C(Cl)—CO—OCH₂—C≡CH |
| Ia.367 | CH₃ | H | Cl | CH=C(Cl)—CO—OCH₂—CO—OCH₃ |
| Ia.368 | CH₃ | H | Cl | CH=C(Cl)—CO—OCH(CH₃)—CO—OCH₃ |
| Ia.369 | CH₃ | H | Cl | CH=C(Cl)—CO—N(CH₃)—CH₂—CO—OCH₃ |
| Ia.370 | CH₃ | H | Cl | CH=C(Cl)—CO—NH—CH(CH₃)—CO—OCH₃ |
| Ia.371 | CH₃ | H | CN | OCH₃ |
| Ia.372 | CH₃ | H | CN | OCH(CH₃)₂ |
| Ia.373 | CH₃ | H | CN | O—CH₂—CH=CH₂ |
| Ia.374 | CH₃ | H | CN | O-cyclopentyl |
| Ia.375 | CH₃ | H | CN | OCH₂—CO—OCH₃ |
| Ia.376 | CH₃ | H | CN | OCH₂—CO—OCH₂—CH=CH₂ |
| Ia.377 | CH₃ | H | CN | OCH₂—CO—OCH₂—CH=CH—CH₃ |
| Ia.378 | CH₃ | H | CN | OCH₂—CO—OCH₂CH₂—CH=CH₂ |
| Ia.379 | CH₃ | H | CN | OCH₂—CO—OCH₂—CH=C(CH₃)₂ |
| Ia.380 | CH₃ | H | CN | OCH₂—CO—OCH₂—C≡CH |
| Ia.381 | CH₃ | H | CN | OCH₂—CO—OCH₂CH₂—C≡CH |
| Ia.382 | CH₃ | H | CN | OCH₂—CO—O-cyclopentyl |
| Ia.383 | CH₃ | H | CN | OCH₂—CO—O—CH₂CH₂—OCH₃ |
| Ia.384 | CH₃ | H | CN | OCH₂—CO—O—CH₂CH₂—OC₂H₅ |
| Ia.385 | CH₃ | H | CN | OCH₂—CO—OCH₂-cyclopropyl |
| Ia.386 | CH₃ | H | CN | OCH₂—CO—OCH₂-cyclobutyl |
| Ia.387 | CH₃ | H | CN | OCH₂—CO—OCH₂-cyclopentyl |

TABLE 1-continued

| No. | R$^1$ | R$^3$ | R$^4$ | R$^5$ |
|---|---|---|---|---|
| Ia.388 | CH$_3$ | H | CN | OCH$_2$—CO—OCH$_2$-cyclohexyl |
| Ia.389 | CH$_3$ | H | CN | OCH$_2$—CO—NH—CH$_3$ |
| Ia.390 | CH$_3$ | H | CN | OCH$_2$—CO—N(CH$_3$)$_2$ |
| Ia.391 | CH$_3$ | H | CN | OCH(CH$_3$)—CO—OCH$_2$—CH=CH$_2$ |
| Ia.392 | CH$_3$ | H | CN | OCH(CH$_3$)—CO—OCH$_2$—CH=CH—CH$_3$ |
| Ia.393 | CH$_3$ | H | CN | OCH(CH$_3$)—CO—OCH$_2$CH$_2$—CH=CH$_2$ |
| Ia.394 | CH$_3$ | H | CN | OCH(CH$_3$)—CO—OCH$_2$—CH=C(CH$_3$)$_2$ |
| Ia.395 | CH$_3$ | H | CN | OCH(CH$_3$)—CO—OCH$_2$—C≡CH |
| Ia.396 | CH$_3$ | H | CN | OCH(CH$_3$)—CO—OCH$_2$CH$_2$—C≡CH |
| Ia.397 | CH$_3$ | H | CN | OCH(CH$_3$)—CO—O-cyclopentyl |
| Ia.398 | CH$_3$ | H | CN | OCH(CH$_3$)—CO—OCH$_2$CH$_2$—OC$_2$H$_5$ |
| Ia.399 | CH$_3$ | H | CN | OCH(CH$_3$)—CO—OCH$_2$-cyclopropyl |
| Ia.400 | CH$_3$ | H | CN | OCH(CH$_3$)—CO—OCH$_2$-cyclobutyl |
| Ia.401 | CH$_3$ | H | CN | OCH(CH$_3$)—CO—OCH$_2$-cyclopentyl |
| Ia.402 | CH$_3$ | H | CN | OCH(CH$_3$)—CO—OCH$_2$-cyclohexyl |
| Ia.403 | CH$_3$ | H | CN | OCH(CH$_3$)—CO—NH—CH$_3$ |
| Ia.404 | CH$_3$ | H | CN | OCH(CH$_3$)—CO—N(CH$_3$)$_2$ |
| Ia.405 | CH$_3$ | H | CN | OC(CH$_3$)$_2$—CO—OCH$_3$ |
| Ia.406 | CH$_3$ | H | CN | OC(CH$_3$)$_2$—CO—OCH$_2$—CH=CH$_2$ |
| Ia.407 | CH$_3$ | H | CN | OC(CH$_3$)$_2$—CO—OCH$_2$—C≡CH |
| Ia.408 | CH$_3$ | H | CN | OC(CH$_3$)$_2$—CO—O-cyclopentyl |
| Ia.409 | CH$_3$ | H | CN | OC(CH$_3$)$_2$—CO—OCH$_2$CH$_2$—OCH$_3$ |
| Ia.410 | CH$_3$ | H | CN | COOH |
| Ia.411 | CH$_3$ | H | CN | CO—OCH(CH$_3$)$_2$ |
| Ia.412 | CH$_3$ | H | CN | CO—OCH$_2$—CH=CH$_2$ |
| Ia.413 | CH$_3$ | H | CN | CO—OCH$_2$—C≡CH |
| Ia.414 | CH$_3$ | H | CN | CO—O-cyclopentyl |
| Ia.415 | CH$_3$ | H | CN | CO—OCH$_2$—CO—OCH$_3$ |
| Ia.416 | CH$_3$ | H | CN | CO—OCH$_2$—CO—OCH$_2$—CH=CH$_2$ |
| Ia.417 | CH$_3$ | H | CN | CO—OCH$_2$—CO—OCH$_2$—C≡CH |
| Ia.418 | CH$_3$ | H | CN | CO—OCH$_2$—CO—OCH$_2$CH$_2$—OCH$_3$ |
| Ia.419 | CH$_3$ | H | CN | CO—OCH(CH$_3$)—CO—OCH$_2$—C≡CH |
| Ia.420 | CH$_3$ | H | CN | CO—CH(CH$_3$)—CO—OCH$_2$CH$_2$—OCH$_3$ |
| Ia.421 | CH$_3$ | H | CN | CO—C(CH$_3$)$_2$—CO—OCH$_2$—C≡CH |
| Ia.422 | CH$_3$ | H | CN | CO—C(CH$_3$)$_2$—CO—OCH$_2$CH$_2$—OCH$_3$ |
| Ia.423 | CH$_3$ | H | CN | CO—NH—CH$_2$—CO—OCH$_3$ |
| Ia.424 | CH$_3$ | H | CN | CO—NH—CH$_2$—CO—OCH$_2$—CH=CH$_2$ |
| Ia.425 | CH$_3$ | H | CN | CO—NH—CH$_2$—CO—OCH$_2$CH$_2$—OCH$_3$ |
| Ia.426 | CH$_3$ | H | CN | CO—NH—CH(CH$_3$)—CO—OCH$_3$ |
| Ia.427 | CH$_3$ | H | CN | CO—NH—CH(CH$_3$)—CO—OCH$_2$—CH=CH$_2$ |
| Ia.428 | CH$_3$ | H | CN | CO—NH—CH(CH$_3$)—CO—OCH$_2$CH$_2$—OCH$_3$ |
| Ia.429 | CH$_3$ | H | CN | CO—N(CH$_3$)—CH$_2$—CO—OCH$_3$ |
| Ia.430 | CH$_3$ | H | CN | CO—N(CH$_3$)—CH$_2$—CO—OCH$_2$—CH=CH$_2$ |
| Ia.431 | CH$_3$ | H | CN | CO—N(CH$_3$)—CH$_2$—CO—OCH$_2$CH$_2$—OCH$_3$ |
| Ia.432 | CH$_3$ | H | CN | CO—N(CH$_3$)—CH(CH$_3$)—CO—OCH$_3$ |
| Ia.433 | CH$_3$ | H | CN | CO—N(CH$_3$)—CH(CH$_3$)—CO—OCH$_2$—CH=CH$_2$ |
| Ia.434 | CH$_3$ | H | CN | CO—N(CH$_3$)—CH(CH$_3$)—CO—OCH$_2$CH$_2$—OCH$_3$ |
| Ia.435 | CH$_3$ | H | CN | CH=C(Cl)—CO—OCH$_2$—CH=CH$_2$ |
| Ia.436 | CH$_3$ | H | CN | CH=C(Cl)—CO—OCH$_2$—C≡CH |
| Ia.437 | CH$_3$ | H | CN | CH=C(Cl)—CO—OCH$_2$—CO—OCH$_3$ |
| Ia.438 | CH$_3$ | H | CN | CH=C(Cl)—CO—OCH(CH$_3$)—CO—OCH$_3$ |
| Ia.439 | CH$_3$ | H | CN | CH=C(Cl)—CO—N(CH$_3$)—CH$_2$—CO—OCH$_3$ |
| Ia.440 | CH$_3$ | H | CN | CH=C(Cl)—CO—NH—CH(CH$_3$)—CO—OCH$_3$ |
| Ia.441 | NH$_2$ | F | Cl | OCH$_3$ |
| Ia.442 | NH$_2$ | F | Cl | OCH(CH$_3$)$_2$ |
| Ia.443 | NH$_2$ | F | Cl | OCH$_2$—CH=CH$_2$ |
| Ia.444 | NH$_2$ | F | Cl | O-cyclopentyl |
| Ia.445 | NH$_2$ | F | Cl | OCH$_2$—CO—OCH$_3$ |
| Ia.446 | NH$_2$ | F | Cl | OCH$_2$—CO—OCH$_2$—CH=CH$_2$ |
| Ia.447 | NH$_2$ | F | Cl | OCH$_2$—CO—OCH$_2$—CH=CH—CH$_3$ |
| Ia.448 | NH$_2$ | F | Cl | OCH$_2$—CO—OCH$_2$CH$_2$—CH=CH$_2$ |
| Ia.449 | NH$_2$ | F | Cl | OCH$_2$—CO—OCH$_2$—CH=C(CH$_3$)$_2$ |
| Ia.450 | NH$_2$ | F | Cl | OCH$_2$—CO—OCH$_2$—C≡CH |
| Ia.451 | NH$_2$ | F | Cl | OCH$_2$—CO—OCH$_2$CH$_2$—C≡CH |
| Ia.452 | NH$_2$ | F | Cl | OCH$_2$—CO—O-cyclopentyl |
| Ia.453 | NH$_2$ | F | Cl | OCH$_2$—CO—OCH$_2$CH$_2$—OCH$_3$ |
| Ia.454 | NH$_2$ | F | Cl | OCH$_2$—CO—OCH$_2$CH$_2$—OC$_2$H$_5$ |
| Ia.455 | NH$_2$ | F | Cl | OCH$_2$—CO—OCH$_2$-cyclopropyl |
| Ia.456 | NH$_2$ | F | Cl | OCH$_2$—CO—OCH$_2$-cyclobutyl |
| Ia.457 | NH$_2$ | F | Cl | OCH$_2$—CO—OCH$_2$-cyclopentyl |
| Ia.458 | NH$_2$ | F | Cl | OCH$_2$—CO—OCH$_2$-cyclohexyl |
| Ia.459 | NH$_2$ | F | Cl | OCH$_2$—CO—NH—CH$_3$ |
| Ia.460 | NH$_2$ | F | Cl | OCH$_2$—CO—N(CH$_3$)$_2$ |
| Ia.461 | NH$_2$ | F | Cl | OCH(CH$_3$)—CO—OCH$_2$—CH=CH$_2$ |
| Ia.462 | NH$_2$ | F | Cl | OCH(CH$_3$)—CO—OCH$_2$—CH=CH—CH$_3$ |
| Ia.463 | NH$_2$ | F | Cl | OCH(CH$_3$)—CO—OCH$_2$CH$_2$—CH=CH$_2$ |
| Ia.464 | NH$_2$ | F | Cl | OCH(CH$_3$)—CO—OCH$_2$—CH=C(CH$_3$)$_2$ |

TABLE 1-continued

| No. | R¹ | R³ | R⁴ | R⁵ |
|---|---|---|---|---|
| Ia.465 | NH₂ | F | Cl | OCH(CH₃)—CO—OCH₂—C≡CH |
| Ia.466 | NH₂ | F | Cl | OCH(CH₃)—CO—OCH₂CH₂—C≡CH |
| Ia.467 | NH₂ | F | Cl | OCH(CH₃)—CO—O-cyclopentyl |
| Ia.468 | NH₂ | F | Cl | OCH(CH₃)—CO—OCH₂CH₂—OC₂H₅ |
| Ia.469 | NH₂ | F | Cl | OCH(CH₃)—CO—OCH₂-cyclopropyl |
| Ia.470 | NH₂ | F | Cl | OCH(CH₃)—CO—OCH₂-cyclobutyl |
| Ia.471 | NH₂ | F | Cl | OCH(CH₃)—CO—OCH₂-cyclopentyl |
| Ia.472 | NH₂ | F | Cl | OCH(CH₃)—CO—OCH₂-cyclohexyl |
| Ia.473 | NH₂ | F | Cl | OCH(CH₃)—CO—NH—CH₃ |
| Ia.474 | NH₂ | F | Cl | OCH(CH₃)—CO—N(CH₃)₂ |
| Ia.475 | NH₂ | F | Cl | OC(CH₃)₂—CO—OCH₃ |
| Ia.476 | NH₂ | F | Cl | OC(CH₃)₂—CO—OCH₂—CH=CH₂ |
| Ia.477 | NH₂ | F | Cl | OC(CH₃)₂—CO—OCH₂—C≡CH |
| Ia.478 | NH₂ | F | Cl | OC(CH₃)₂—CO—O-cyclopentyl |
| Ia.479 | NH₂ | F | Cl | OC(CH₃)₂—CO—OCH₂CH₂—OCH₃ |
| Ia.480 | NH₂ | F | Cl | COOH |
| Ia.481 | NH₂ | F | Cl | CO—OCH(CH₃)₂ |
| Ia.482 | NH₂ | F | Cl | CO—OCH₂—CH=CH₂ |
| Ia.483 | NH₂ | F | Cl | CO—OCH₂—C≡CH |
| Ia.484 | NH₂ | F | Cl | CO—O-cyclopentyl |
| Ia.485 | NH₂ | F | Cl | CO—OCH₂—CO—OCH₃ |
| Ia.486 | NH₂ | F | Cl | CO—OCH₂—CO—OCH₂—CH=CH₂ |
| Ia.487 | NH₂ | F | Cl | CO—OCH₂—CO—OCH₂—C≡CH |
| Ia.488 | NH₂ | F | Cl | CO—OCH₂—CO—OCH₂CH₂—OCH₃ |
| Ia.489 | NH₂ | F | Cl | CO—OCH(CH₃)—CO—OCH₂—C≡CH |
| Ia.490 | NH₂ | F | Cl | CO—OCH(CH₃)—CO—OCH₂CH₂—OCH₃ |
| Ia.491 | NH₂ | F | Cl | CO—OC(CH₃)₂—CO—OCH₂—C≡CH |
| Ia.492 | NH₂ | F | Cl | CO—OC(CH₃)₂—CO—OCH₂CH₂—OCH₃ |
| Ia.493 | NH₂ | F | Cl | CO—NH—CH₂—CO—OCH₃ |
| Ia.494 | NH₂ | F | Cl | CO—NH—CH₂—CO—OCH₂CH=CH₂ |
| Ia.495 | NH₂ | F | Cl | CO—NH—CH₂—CO—OCH₂CH₂—OCH₃ |
| Ia.496 | NH₂ | F | Cl | CO—NH—CH(CH₃)—CO—OCH₃ |
| Ia.497 | NH₂ | F | Cl | CO—NH—CH(CH₃)—CO—OCH₂—CH=CH₂ |
| Ia.498 | NH₂ | F | Cl | CO—NH—CH(CH₃)—CO—OCH₂CH₂—OCH₃ |
| Ia.499 | NH₂ | F | Cl | CO—N(CH₃)—CH₂—CO—OCH₃ |
| Ia.500 | NH₂ | F | Cl | CO—N(CH₃)—CH₂—CO—OCH₂—CH=CH₂ |
| Ia.501 | NH₂ | F | Cl | CO—N(CH₃)—CH₂—CO—OCH₂CH₂—OCH₃ |
| Ia.502 | NH₂ | F | Cl | CO—N(CH₃)—CH(CH₃)—CO—OCH₃ |
| Ia.503 | NH₂ | F | Cl | CO—N(CH₃)—CH(CH₃)—CO—OCH₂—CH=CH₂ |
| Ia.504 | NH₂ | F | Cl | CO—N(CH₃)—CH(CH₃)—CO—OCH₂CH₂—OCH₃ |
| Ia.505 | NH₂ | F | Cl | CH=C(Cl)—CO—OCH₂—CH=CH₂ |
| Ia.506 | NH₂ | F | Cl | CH=C(Cl)—CO—OCH₂—C≡CH |
| Ia.507 | NH₂ | F | Cl | CH=C(Cl)—CO—OCH₂—CO—OCH₃ |
| Ia.508 | NH₂ | F | Cl | CH=C(Cl)—CO—OCH(CH₃)—CO—OCH₃ |
| Ia.509 | NH₂ | F | Cl | CH=C(Cl)—CO—N(CH₃)—CH₂—CO—OCH₃ |
| Ia.510 | NH₂ | F | Cl | CH=C(Cl)—CO—NH—CH(CH₃)—CO—OCH₃ |
| Ia.511 | NH₂ | F | CN | OCH₃ |
| Ia.512 | NH₂ | F | CN | OCH(CH₃)₂ |
| Ia.513 | NH₂ | F | CN | OCH₂—CH=CH₂ |
| Ia.514 | NH₂ | F | CN | O-cyclopentyl |
| Ia.515 | NH₂ | F | CN | OCH₂—CO—OCH₃ |
| Ia.516 | NH₂ | F | CN | OCH₂—CO—OCH₂—CH=CH₂ |
| Ia.517 | NH₂ | F | CN | OCH₂—CO—OCH₂—CH=CH—CH₃ |
| Ia.518 | NH₂ | F | CN | OCH₂—CO—OCH₂CH₂—CH=CH₂ |
| Ia.519 | NH₂ | F | CN | OCH₂—CO—OCH₂—CH=C(CH₃)₂ |
| Ia.520 | NH₂ | F | CN | OCH₂—CO—OCH₂—C≡CH |
| Ia.521 | NH₂ | F | CN | OCH₂—CO—OCH₂CH₂—C≡CH |
| Ia.522 | NH₂ | F | CN | OCH₂—CO—O-cyclopentyl |
| Ia.523 | NH₂ | F | CN | OCH₂—CO—OCH₂CH₂—OCH₃ |
| Ia.524 | NH₂ | F | CN | OCH₂—CO—OCH₂CH₂—OC₂H₅ |
| Ia.525 | NH₂ | F | CN | OCH₂—CO—OCH₂-cyclopropyl |
| Ia.526 | NH₂ | F | CN | OCH₂—CO—OCH₂-cyclobutyl |
| Ia.527 | NH₂ | F | CN | OCH₂—CO—OCH₂-cyclopentyl |
| Ia.528 | NH₂ | F | CN | OCH₂—CO—OCH₂-cyclohexyl |
| Ia.529 | NH₂ | F | CN | OCH₂—CO—NH—CH₃ |
| Ia.530 | NH₂ | F | CN | OCH₂—CO—N(CH₃)₂ |
| Ia.531 | NH₂ | F | CN | OCH(CH₃)—CO—OCH₂—CH=CH₂ |
| Ia.532 | NH₂ | F | CN | OCH(CH₃)—CO—OCH₂—CH=CH—CH₃ |
| Ia.533 | NH₂ | F | CN | OCH(CH₃)—CO—OCH₂CH₂—CH=CH₂ |
| Ia.534 | NH₂ | F | CN | OCH(CH₃)—CO—OCH₂—CH=C(CH₃)₂ |
| Ia.535 | NH₂ | F | CN | OCH(CH₃)—CO—OCH₂—C≡CH |
| Ia.536 | NH₂ | F | CN | OCH(CH₃)—CO—OCH₂CH₂—C≡CH |
| Ia.537 | NH₂ | F | CN | OCH(CH₃)—CO—O-cyclopentyl |
| Ia.538 | NH₂ | F | CN | OCH(CH₃)—CO—OCH₂CH₂—OC₂H₅ |
| Ia.539 | NH₂ | F | CN | OCH(CH₃)—CO—OCH₂-cyclopropyl |
| Ia.540 | NH₂ | F | CN | OCH(CH₃)—CO—OCH₂-cyclobutyl |
| Ia.541 | NH₂ | F | CN | OCH(CH₃)—CO—OCH₂-cyclopentyl |

TABLE 1-continued

| No. | R¹ | R³ | R⁴ | R⁵ |
|---|---|---|---|---|
| Ia.542 | NH₂ | F | CN | OCH(CH₃)—CO—OCH₂-cyclohexyl |
| Ia.543 | NH₂ | F | CN | OCH(CH₃)—CO—NH—CH₃ |
| Ia.544 | NH₂ | F | CN | OCH(CH₃)—CO—N(CH₃)₂ |
| Ia.545 | NH₂ | F | CN | OC(CH₃)₂—CO—OCH₃ |
| Ia.546 | NH₂ | F | CN | OC(CH₃)₂—CO—OCH₂—CH=CH₂ |
| Ia.547 | NH₂ | F | CN | OC(CH₃)₂—CO—OCH₂—C≡CH |
| Ia.548 | NH₂ | F | CN | OC(CH₃)₂—CO—O-cyclopentyl |
| Ia.549 | NH₂ | F | CN | OC(CH₃)₂—CO—OCH₂CH₂—OCH₃ |
| Ia.550 | NH₂ | F | CN | COOH |
| Ia.551 | NH₂ | F | CN | CO—OCH(CH₃)₂ |
| Ia.552 | NH₂ | F | CN | CO—OCH₂—CH=CH₂ |
| Ia.553 | NH₂ | F | CN | CO—OCH₂—C≡CH |
| Ia.554 | NH₂ | F | CN | CO—O-cyclopentyl |
| Ia.555 | NH₂ | F | CN | CO—OCH₂—CO—OCH₃ |
| Ia.556 | NH₂ | F | CN | CO—OCH₂—CO—OCH₂—CH=CH₂ |
| Ia.557 | NH₂ | F | CN | CO—OCH₂—CO—OCH₂—C≡CH |
| Ia.558 | NH₂ | F | CN | CO—OCH₂—CO—OCH₂CH₂—OCH₃ |
| Ia.559 | NH₂ | F | CN | CO—OCH(CH₃)—CO—OCH₂—C≡CH |
| Ia.560 | NH₂ | F | CN | CO—OCH(CH₃)—CO—OCH₂CH₂—OCH₃ |
| Ia.561 | NH₂ | F | CN | CO—OC(CH₃)₂—CO—OCH₂—C≡CH |
| Ia.562 | NH₂ | F | CN | CO—OC(CH₃)₂—CO—OCH₂CH₂—OCH₃ |
| Ia.563 | NH₂ | F | CN | CO—NH—CH₂CO—OCH₃ |
| Ia.564 | NH₂ | F | CN | CO—NH—CH₂CO—OCH₂CH=CH₂ |
| Ia.565 | NH₂ | F | CN | CO—NH—CH₂CO—OCH₂CH₂—OCH₃ |
| Ia.566 | NH₂ | F | CN | CO—NH—CH(CH₃)—CO—OCH₃ |
| Ia.567 | NH₂ | F | CN | CO—NH—CH(CH₃)—CO—OCH₂—CH=CH₂ |
| Ia.568 | NH₂ | F | CN | CO—NH—CH(CH₃)—CO—OCH₂CH₂—OCH₃ |
| Ia.569 | NH₂ | F | CN | CO—N(CH₃)—CH₂—CO—OCH₃ |
| Ia.570 | NH₂ | F | CN | CO—N(CH₃)—CH₂—CO—OCH₂—CH=CH₂ |
| Ia.571 | NH₂ | F | CN | CO—N(CH₃)—CH₂—CO—OCH₂CH₂—OCH₃ |
| Ia.572 | NH₂ | F | CN | CO—N(CH₃)—CH(CH₃)—CO—OCH₃ |
| Ia.573 | NH₂ | F | CN | CO—N(CH₃)—CH(CH₃)—CO—OCH₂—CH=CH₂ |
| Ia.574 | NH₂ | F | CN | CO—N(CH₃)—CH(CH₃)—CO—OCH₂CH₂—OCH₃ |
| Ia.575 | NH₂ | F | CN | CH=C(Cl)—CO—OCH₂—CH=CH₂ |
| Ia.576 | NH₂ | F | CN | CH=C(Cl)—CO—OCH₂—C≡CH |
| Ia.577 | NH₂ | F | CN | CH=C(Cl)—CO—OCH₂—CO—OCH₃ |
| Ia.578 | NH₂ | F | CN | CH=C(Cl)—CO—OCH(CH₃)—CO—OCH₃ |
| Ia.579 | NH₂ | F | CN | CH=C(Cl)—CO—N(CH₃)—CH₂—CO—OCH₃ |
| Ia.580 | NH₂ | F | CN | CH=C(Cl)—CO—NH—CH(CH₃)—CO—OCH₃ |
| Ia.581 | NH₂ | H | Cl | OCH₃ |
| Ia.582 | NH₂ | H | Cl | OCH(CH₃)₂ |
| Ia.583 | NH₂ | H | Cl | OCH₂—CH=CH₂ |
| Ia.584 | NH₂ | H | Cl | O-cyclopentyl |
| Ia.585 | NH₂ | H | Cl | OCH₂—CO—OCH₃ |
| Ia.586 | NH₂ | H | Cl | OCH₂—CO—OCH₂—CH=CH₂ |
| Ia.587 | NH₂ | H | Cl | OCH₂—CO—OCH₂—CH=CH—CH₃ |
| Ia.588 | NH₂ | H | Cl | OCH₂—CO—OCH₂CH₂—CH=CH₂ |
| Ia.589 | NH₂ | H | Cl | OCH₂—CO—OCH₂CH=C(CH₃)₂ |
| Ia.590 | NH₂ | H | Cl | OCH₂—CO—OCH₂—C≡CH |
| Ia.591 | NH₂ | H | Cl | OCH₂—CO—OCH₂CH₂—C≡CH |
| Ia.592 | NH₂ | H | Cl | OCH₂—CO—O-cyclopentyl |
| Ia.593 | NH₂ | H | Cl | OCH₂—CO—OCH₂CH₂—OCH₃ |
| Ia.594 | NH₂ | H | Cl | OCH₂—CO—OCH₂CH₂—OC₂H₅ |
| Ia.595 | NH₂ | H | Cl | OCH₂—CO—OCH₂-cyclopropyl |
| Ia.596 | NH₂ | H | Cl | OCH₂—CO—OCH₂-cyclobutyl |
| Ia.597 | NH₂ | H | Cl | OCH₂—CO—OCH₂-cyclopentyl |
| Ia.598 | NH₂ | H | Cl | OCH₂—CO—OCH₂-cyclohexyl |
| Ia.599 | NH₂ | H | Cl | OCH₂—CO—NH—CH₃ |
| Ia.600 | NH₂ | H | Cl | OCH₂—CO—N(CH₃)₂ |
| Ia.601 | NH₂ | H | Cl | OCH(CH₃)—CO—OCH₂—CH=CH₂ |
| Ia.602 | NH₂ | H | Cl | OCH(CH₃)—CO—OCH₂—CH=CH—CH₃ |
| Ia.603 | NH₂ | H | Cl | OCH(CH₃)—CO—OCH₂—CH₂—CH=CH₂ |
| Ia.604 | NH₂ | H | Cl | OCH(CH₃)—CO—OCH₂—CH=C(CH₃)₂ |
| Ia.605 | NH₂ | H | Cl | OCH(CH₃)—CO—OCH₂—C≡CH |
| Ia.606 | NH₂ | H | Cl | OCH(CH₃)—CO—OCH₂CH₂—C≡CH |
| Ia.607 | NH₂ | H | Cl | OCH(CH₃)—CO—O-cyclopentyl |
| Ia.608 | NH₂ | H | Cl | OCH(CH₃)—CO—OCH₂CH₂—OC₂H₅ |
| Ia.609 | NH₂ | H | Cl | OCH(CH₃)—CO—OCH₂-cyclopropyl |
| Ia.610 | NH₂ | H | Cl | OCH(CH₃)—CO—OCH₂-cyclobutyl |
| Ia.611 | NH₂ | H | Cl | OCH(CH₃)—CO—OCH₂-cyclopentyl |
| Ia.612 | NH₂ | H | Cl | OCH(CH₃)—CO—OCH₂-cyclohexyl |
| Ia.613 | NH₂ | H | Cl | OCH(CH₃)—CO—NH—CH₃ |
| Ia.614 | NH₂ | H | Cl | OCH(CH₃)—CO—N(CH₃)₂ |
| Ia.615 | NH₂ | H | Cl | OC(CH₃)₂—CO—OCH₃ |
| Ia.616 | NH₂ | H | Cl | OC(CH₃)₂—CO—OCH₂—CH=CH₂ |
| Ia.617 | NH₂ | H | Cl | OC(CH₃)₂—CO—OCH₂—C≡CH |
| Ia.618 | NH₂ | H | Cl | OC(CH₃)₂—CO—O-cyclopentyl |

TABLE 1-continued

| No. | R$^1$ | R$^3$ | R$^4$ | R$^5$ |
|---|---|---|---|---|
| Ia.619 | NH$_2$ | H | Cl | OC(CH$_3$)$_2$—CO—OCH$_2$CH$_2$—OCH$_3$ |
| Ia.620 | NH$_2$ | H | Cl | COOH |
| Ia.621 | NH$_2$ | H | Cl | CO—OCH(CH$_3$)$_2$ |
| Ia.622 | NH$_2$ | H | Cl | CO—OCH$_2$—CH=CH$_2$ |
| Ia.623 | NH$_2$ | H | Cl | CO—OCH$_2$—C≡CH |
| Ia.624 | NH$_2$ | H | Cl | CO—O-cyclopentyl |
| Ia.625 | NH$_2$ | H | Cl | CO—OCH$_2$—CO—OCH$_3$ |
| Ia.626 | NH$_2$ | H | Cl | CO—OCH$_2$—CO—OCH$_2$—CH=CH$_2$ |
| Ia.627 | NH$_2$ | H | Cl | CO—OCH$_2$—CO—OCH$_2$—C≡CH |
| Ia.628 | NH$_2$ | H | Cl | CO—OCH$_2$—CO—OCH$_2$CH$_2$—OCH$_3$ |
| Ia.629 | NH$_2$ | H | Cl | CO—OCH(CH$_3$)—CO—OCH$_2$—C≡CH |
| Ia.630 | NH$_2$ | H | Cl | CO—OCH(CH$_3$)—CO—OCH$_2$CH$_2$—OCH$_3$ |
| Ia.631 | NH$_2$ | H | Cl | CO—OC(CH$_3$)$_2$—CO—OCH$_2$—C≡CH |
| Ia.632 | NH$_2$ | H | Cl | CO—OC(CH$_3$)$_2$—CO—OCH$_2$CH$_2$—OCH$_3$ |
| Ia.633 | NH$_2$ | H | Cl | CO—NH—CH$_2$—CO—OCH$_3$ |
| Ia.634 | NH$_2$ | H | Cl | CO—NH—CH$_2$—CO—OCH$_2$—CH=CH$_2$ |
| Ia.635 | NH$_2$ | H | Cl | CO—NH—CH$_2$—CO—OCH$_2$CH$_2$—OCH$_3$ |
| Ia.636 | NH$_2$ | H | Cl | CO—NH—CH(CH$_3$)—CO—OCH$_3$ |
| Ia.637 | NH$_2$ | H | Cl | CO—NH—CH(CH$_3$)—CO—OCH$_2$—CH=CH$_2$ |
| Ia.638 | NH$_2$ | H | Cl | CO—NH—CH(CH$_3$)—CO—OCH$_2$CH$_2$—OCH$_3$ |
| Ia.639 | NH$_2$ | H | Cl | CO—N(CH$_3$)—CH$_2$—CO—OCH$_3$ |
| Ia.640 | NH$_2$ | H | Cl | CO—N(CH$_3$)—CH$_2$—CO—OCH$_2$—CH=CH$_2$ |
| Ia.641 | NH$_2$ | H | Cl | CO—N(CH$_3$)—CH$_2$—CO—OCH$_2$CH$_2$—OCH$_3$ |
| Ia.642 | NH$_2$ | H | Cl | CO—N(CH$_3$)—CH(CH$_3$)—CO—OCH$_3$ |
| Ia.643 | NH$_2$ | H | Cl | CO—N(CH$_3$)—CH(CH$_3$)—CO—OCH$_2$—CH=CH$_2$ |
| Ia.644 | NH$_2$ | H | Cl | CO—N(CH$_3$)—CH(CH$_3$)—CO—OCH$_2$CH$_2$—OCH$_3$ |
| Ia.645 | NH$_2$ | H | Cl | CH=C(Cl)—CO—OCH$_2$—CH=CH$_2$ |
| Ia.646 | NH$_2$ | H | Cl | CH=C(Cl)—CO—OCH$_2$—C≡CH |
| Ia.647 | NH$_2$ | H | Cl | CH=C(Cl)—CO—OCH$_2$—CO—OCH$_3$ |
| Ia.648 | NH$_2$ | H | Cl | CH=C(Cl)—CO—OCH(CH$_3$)—CO—OCH$_3$ |
| Ia.649 | NH$_2$ | H | Cl | CH=C(Cl)—CO—N(CH$_3$)—CH$_2$—CO—OCH$_3$ |
| Ia.650 | NH$_2$ | H | Cl | CH=C(Cl)—CO—NH—CH(CH$_3$)—CO—OCH$_3$ |
| Ia.651 | NH$_2$ | H | CN | OCH$_3$ |
| Ia.652 | NH$_2$ | H | CN | OCH(CH$_3$)$_2$ |
| Ia.653 | NH$_2$ | H | CN | OCH$_2$—CH=CH$_2$ |
| Ia.654 | NH$_2$ | H | CN | O-cyclopentyl |
| Ia.655 | NH$_2$ | H | CN | OCH$_2$—CO—OCH$_3$ |
| Ia.656 | NH$_2$ | H | CN | OCH$_2$—CO—OCH$_2$—CH=CH$_2$ |
| Ia.657 | NH$_2$ | H | CN | OCH$_2$—CO—OCH$_2$—CH=CHCH$_3$ |
| Ia.658 | NH$_2$ | H | CN | OCH$_2$—CO—OCH$_2$CH$_2$—CH=CH$_2$ |
| Ia.659 | NH$_2$ | H | CN | OCH$_2$—CO—OCH$_2$—CH=C(CH$_3$)$_2$ |
| Ia.660 | NH$_2$ | H | CN | OCH$_2$—CO—OCH$_2$—C≡CH |
| Ia.661 | NH$_2$ | H | CN | OCH$_2$—CO—OCH$_2$CH$_2$—C≡CH |
| Ia.662 | NH$_2$ | H | CN | OCH$_2$—CO—O-cyclopentyl |
| Ia.663 | NH$_2$ | H | CN | OCH$_2$—CO—OCH$_2$CH$_2$—OCH$_3$ |
| Ia.664 | NH$_2$ | H | CN | OCH$_2$—CO—OCH$_2$CH$_2$—OC$_2$H$_5$ |
| Ia.665 | NH$_2$ | H | CN | OCH$_2$—CO—OCH$_2$-cyclopropyl |
| Ia.666 | NH$_2$ | H | CN | OCH$_2$—CO—OCH$_2$-cyclobutyl |
| Ia.667 | NH$_2$ | H | CN | OCH$_2$—CO—OCH$_2$-cyclopentyl |
| Ia.668 | NH$_2$ | H | CN | OCH$_2$—CO—OCH$_2$-cyclohexyl |
| Ia.669 | NH$_2$ | H | CN | OCH$_2$—CO—NH—CH$_3$ |
| Ia.670 | NH$_2$ | H | CN | OCH$_2$—CO—N(CH$_3$)$_2$ |
| Ia.671 | NH$_2$ | H | CN | OCH(CH$_3$)—CO—OCH$_2$—CH=CH$_2$ |
| Ia.672 | NH$_2$ | H | CN | OCH(CH$_3$)—CO—OCH$_2$—CH=CH—CH$_3$ |
| Ia.673 | NH$_2$ | H | CN | OCH(CH$_3$)—CO—OCH$_2$CH$_2$—CH=CH$_2$ |
| Ia.674 | NH$_2$ | H | CN | OCH(CH$_3$)—CO—OCH$_2$—CH=C(CH$_3$)$_2$ |
| Ia.675 | NH$_2$ | H | CN | OCH(CH$_3$)—CO—OCH$_2$—C≡CH |
| Ia.676 | NH$_2$ | H | CN | OCH(CH$_3$)—CO—OCH$_2$CH$_2$—C≡CH |
| Ia.677 | NH$_2$ | H | CN | OCH(CH$_3$)—CO—O-cyclopentyl |
| Ia.678 | NH$_2$ | H | CN | OCH(CH$_3$)—CO—OCH$_2$CH$_2$—OC$_2$H$_5$ |
| Ia.679 | NH$_2$ | H | CN | OCH(CH$_3$)—CO—OCH$_2$-cyclopropyl |
| Ia.680 | NH$_2$ | H | CN | OCH(CH$_3$)—CO—OCH$_2$-cyclobutyl |
| Ia.681 | NH$_2$ | H | CN | OCH(CH$_3$)—CO—OCH$_2$-cyclopentyl |
| Ia.682 | NH$_2$ | H | CN | OCH(CH$_3$)—CO—OCH$_2$-cyclohexyl |
| Ia.683 | NH$_2$ | H | CN | OCH(CH$_3$)—CO—NH—CH$_3$ |
| Ia.684 | NH$_2$ | H | CN | OCH(CH$_3$)—CO—N(CH$_3$)$_2$ |
| Ia.685 | NH$_2$ | H | CN | OC(CH$_3$)$_2$—CO—OCH$_3$ |
| Ia.686 | NH$_2$ | H | CN | OC(CH$_3$)$_2$—CO—OCH$_2$—CH=CH$_2$ |
| Ia.687 | NH$_2$ | H | CN | OC(CH$_3$)$_2$—CO—OCH$_2$—C≡CH |
| Ia.688 | NH$_2$ | H | CN | OC(CH$_3$)$_2$—CO—O-cyclopentyl |
| Ia.689 | NH$_2$ | H | CN | OC(CH$_3$)$_2$—CO—OCH$_2$CH$_2$—OCH$_3$ |
| Ia.690 | NH$_2$ | H | CN | COOH |
| Ia.691 | NH$_2$ | H | CN | CO—OCH(CH$_3$)$_2$ |
| Ia.692 | NH$_2$ | H | CN | CO—OCH$_2$—CH=CH$_2$ |
| Ia.693 | NH$_2$ | H | CN | CO—OCH$_2$—C≡CH |
| Ia.694 | NH$_2$ | H | CN | CO—O-cyclopentyl |
| Ia.695 | NH$_2$ | H | CN | CO—OCH$_2$—CO—OCH$_3$ |

TABLE 1-continued

| No. | $R^1$ | $R^3$ | $R^4$ | $R^5$ |
|---|---|---|---|---|
| Ia.696 | $NH_2$ | H | CN | CO—$OCH_2$—CO—$OCH_2$—CH=$CH_2$ |
| Ia.697 | $NH_2$ | H | CN | CO—$OCH_2$—CO—$OCH_2$—C≡CH |
| Ia.698 | $NH_2$ | H | CN | CO—$OCH_2$—CO—$OCH_2CH_2$—$OCH_3$ |
| Ia.699 | $NH_2$ | H | CN | CO—$OCH(CH_3)$—CO—$OCH_2$—C≡CH |
| Ia.700 | $NH_2$ | H | CN | CO—$OCH(CH_3)$—CO—$OCH_2CH_2$—$OCH_3$ |
| Ia.701 | $NH_2$ | H | CN | CO—$OC(CH_3)_2$—CO—$OCH_2$—C≡CH |
| Ia.702 | $NH_2$ | H | CN | CO—$OC(CH_3)_2$—CO—$OCH_2CH_2$—$OCH_3$ |
| Ia.703 | $NH_2$ | H | CN | CO—NH—$CH_2$—CO—$OCH_3$ |
| Ia.704 | $NH_2$ | H | CN | CO—NH—$CH_2$—CO—$OCH_2$—CH=$CH_2$ |
| Ia.705 | $NH_2$ | H | CN | CO—NH—$CH_2$—CO—$OCH_2CH_2$—$OCH_3$ |
| Ia.706 | $NH_2$ | H | CN | CO—NH—$CH(CH_3)$—CO—$OCH_3$ |
| Ia.707 | $NH_2$ | H | CN | CO—NH—$CH(CH_3)$—CO—$OCH_2$—CH=$CH_2$ |
| Ia.708 | $NH_2$ | H | CN | CO—NH—$CH(CH_3)$—CO—$OCH_2CH_2$—$OCH_3$ |
| Ia.709 | $NH_2$ | H | CN | CO—$N(CH_3)$—$CH_2$—CO—$OCH_3$ |
| Ia.710 | $NH_2$ | H | CN | CO—$N(CH_3)$—$CH_2$—CO—$OCH_2$—CH=$CH_2$ |
| Ia.711 | $NH_2$ | H | CN | CO—$N(CH_3)$—$CH_2$—CO—$OCH_2CH_2$—$OCH_3$ |
| Ia.712 | $NH_2$ | H | CN | CO—$N(CH_3)$—$CH(CH_3)$—CO—$OCH_3$ |
| Ia.713 | $NH_2$ | H | CN | CO—$N(CH_3)$—$CH(CH_3)$—CO—$OCH_2$—CH=$CH_2$ |
| Ia.714 | $NH_2$ | H | CN | CO—$N(CH_3)$—$CH(CH_3)$—CO—$OCH_2CH_2$—$OCH_3$ |
| Ia.715 | $NH_2$ | H | CN | CH=C(Cl)—CO—$OCH_2$—CH=$CH_2$ |
| Ia.716 | $NH_2$ | H | CN | CH=C(Cl)—CO—$OCH_2$—C≡CH |
| Ia.717 | $NH_2$ | H | CN | CH=C(Cl)—CO—$OCH_2$—CO—$OCH_3$ |
| Ia.718 | $NH_2$ | H | CN | CH=C(Cl)—CO—$OCH(CH_3)$—CO—$OCH_3$ |
| Ia.719 | $NH_2$ | H | CN | CH=C(Cl)—CO—$N(CH_3)$—$CH_2$—CO—$OCH_3$ |
| Ia.720 | $NH_2$ | H | CN | CH=C(Cl)—CO—NH—$CH(CH_3)$—CO—$OCH_3$ |

Other particularly preferred 1-aryl-4-thiotriazines are those of the formula Ib, in particular the compounds Ib.1 to Ib.720, which differ from the corresponding compounds Ia.1 to Ia.720 only by the fact that $R^2$ is amino:

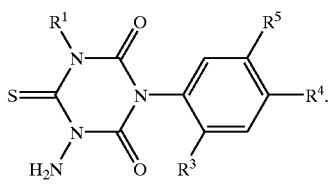

Ib

Other particularly preferred 1-aryl-4-thiotriazines are those of the formula Ic {= I where $Y+R^5$=>C—O—C$(R^6)$=N—}

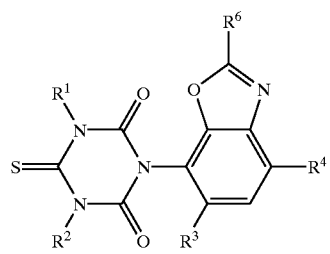

Ic in particular the compounds Ic.1 to Ic.55, which are listed in able 2 below:

TABLE 2

| No. | $R^1$ | $R^2$ | $R^3$ | $R^4$ | $R^6$ |
|---|---|---|---|---|---|
| Ic.1 | $CH_3$ | $CH_3$ | H | Cl | H |
| Ic.2 | $CH_3$ | $CH_3$ | H | Cl | $CH_3$ |
| Ic.3 | $CH_3$ | $CH_3$ | H | Cl | $C_2H_5$ |
| Ic.4 | $CH_3$ | $CH_3$ | H | Cl | i-$C_3H_7$ |
| Ic.5 | $CH_3$ | $CH_3$ | H | Cl | cyclopropyl |
| Ic.6 | $CH_3$ | $CH_3$ | H | Cl | allyl |
| Ic.7 | $CH_3$ | $CH_3$ | H | Cl | propargyl |
| Ic.8 | $CH_3$ | $CH_3$ | H | Cl | 1-(methoxycarbonyl)ethyl |
| Ic.9 | $CH_3$ | $CH_3$ | H | Cl | $OCH_3$ |
| Ic.10 | $CH_3$ | $CH_3$ | H | Cl | $OC_2H_5$ |
| Ic.11 | $CH_3$ | $CH_3$ | H | Cl | O-i-$C_3H_7$ |
| Ic.12 | $CH_3$ | $CH_3$ | F | Cl | H |
| Ic.13 | $CH_3$ | $CH_3$ | F | Cl | $CH_3$ |
| Ic.14 | $CH_3$ | $CH_3$ | F | Cl | $C_2H_5$ |
| Ic.15 | $CH_3$ | $CH_3$ | F | Cl | i-$C_3H_7$ |
| Ic.16 | $CH_3$ | $CH_3$ | F | Cl | cyclopropyl |
| Ic.17 | $CH_3$ | $CH_3$ | F | Cl | allyl |
| Ic.18 | $CH_3$ | $CH_3$ | F | Cl | propargyl |
| Ic.19 | $CH_3$ | $CH_3$ | F | Cl | 1-(methoxycarbonyl)ethyl |
| Ic.20 | $CH_3$ | $CH_3$ | F | Cl | $OCH_3$ |
| Ic.21 | $CH_3$ | $CH_3$ | F | Cl | $OC_2H_5$ |
| Ic.22 | $CH_3$ | $CH_3$ | F | Cl | $OCH(CH_3)_2$ |
| Ic.23 | $CH_3$ | $CH_3$ | F | CN | H |
| Ic.24 | $CH_3$ | $CH_3$ | F | CN | $CH_3$ |
| Ic.25 | $CH_3$ | $CH_3$ | F | CN | $C_2H_5$ |
| Ic.26 | $CH_3$ | $CH_3$ | F | CN | i-$C_3H_7$ |
| Ic.27 | $CH_3$ | $CH_3$ | F | CN | cyclopropyl |
| Ic.28 | $CH_3$ | $CH_3$ | F | CN | allyl |
| Ic.29 | $CH_3$ | $CH_3$ | F | CN | propargyl |
| Ic.30 | $CH_3$ | $CH_3$ | F | CN | 1-(methoxycarbonyl)ethyl |
| Ic.31 | $CH_3$ | $CH_3$ | F | CN | $OCH_3$ |
| Ic.32 | $CH_3$ | $CH_3$ | F | CN | $OC_2H_5$ |
| Ic.33 | $CH_3$ | $CH_3$ | F | CN | $OCH(CH_3)_2$ |
| Ic.34 | $CH_3$ | $NH_2$ | | Cl | H |
| Ic.35 | $CH_3$ | $NH_2$ | | Cl | $CH_3$ |
| Ic.36 | $CH_3$ | $NH_2$ | | Cl | $C_2H_5$ |
| Ic.37 | $CH_3$ | $NH_2$ | | Cl | i-$C_3H_7$ |
| Ic.38 | $CH_3$ | $NH_2$ | | Cl | cyclopropyl |
| Ic.39 | $CH_3$ | $NH_2$ | | Cl | allyl |
| Ic.40 | $CH_3$ | $NH_2$ | | Cl | propargyl |
| Ic.41 | $CH_3$ | $NH_2$ | | Cl | 1-(methoxycarbonyl)ethyl |
| Ic.42 | $CH_3$ | $NH_2$ | | Cl | $OCH_3$ |
| Ic.43 | $CH_3$ | $NH_2$ | | Cl | $OC_2H_5$ |

TABLE 2-continued

| No. | $R^1$ | $R^2$ | $R^3$ | $R^4$ | $R^6$ |
|---|---|---|---|---|---|
| Ic.44 | $CH_3$ | $NH_2$ | | Cl | $OCH(CH_3)_2$ |
| Ic.45 | $CH_3$ | $NH_2$ | | CN | H |
| Ic.46 | $CH_3$ | $NH_2$ | | CN | $CH_3$ |
| Ic.47 | $CH_3$ | $NH_2$ | | CN | $C_2H_5$ |
| Ic.48 | $CH_3$ | $NH_2$ | | CN | $i$-$C_3H_7$ |
| Ic.49 | $CH_3$ | $NH_2$ | | CN | cyclopropyl |
| Ic.50 | $CH_3$ | $NH_2$ | | CN | allyl |
| Ic.51 | $CH_3$ | $NH_2$ | | CN | propargyl |
| Ic.52 | $CH_3$ | $NH_2$ | | CN | 1-(methoxycarbo-nyl)ethyl |
| Ic.53 | $CH_3$ | $NH_2$ | | CN | $OCH_3$ |
| Ic.54 | $CH_3$ | $NH_2$ | | CN | $OC_2H_5$ |
| Ic.55 | $CH_3$ | $NH_2$ | | CN | $OCH(CH_3)_2$ |

The 1-aryl-4-thiotriazines of the formula I can be obtained by various routes, in particular by one of the following processes:

A) Analogously to J. Chem. Soc. Perkin Trans. (1982), 1321

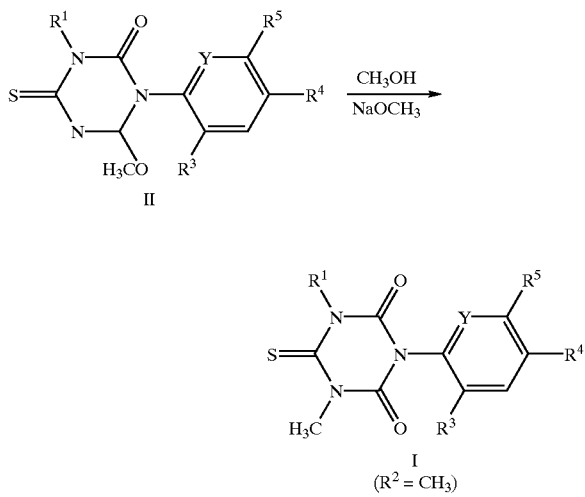

As regards the conditions for carrying out the reaction, the abovementioned reference may be referred to.

B) Analogously to J. Chem. Soc. Perkin Trans. (1992), 1139

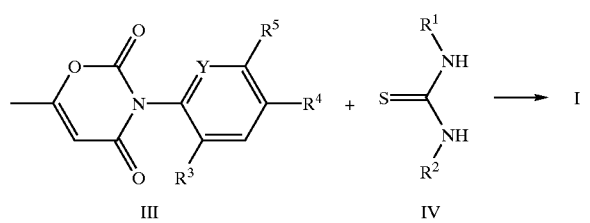

As regards the reaction conditions, the abovementioned reference may be referred to.

In accordance with a preferred process, which constitutes a further subject matter of the invention, the 1-aryl-4-thiotriazines according to the invention are prepared by reacting aryl isocyanates with thioureas, followed by cyclization.

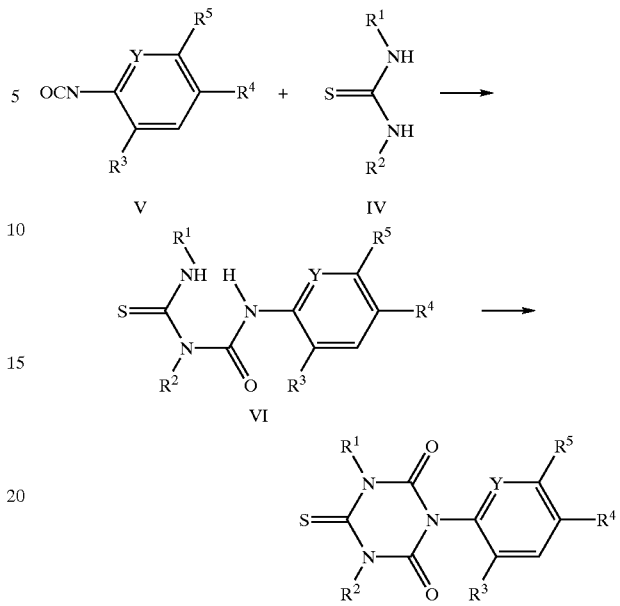

In accordance with an especially preferred embodiment of process C according to the invention, the isocyanate is reacted with the thiourea in the presence of an activated carbon dioxide source. Preferred examples which may be mentioned here are carbodiimidazole, phosgene, diphosgene and triphosgene, and chloroformic esters.

Process ($C_)$) according to the invention and processes ($A_)$) and ($B_)$) for the preparation of the compounds of the formula (I) are preferably carried out in the presence of a suitable reaction auxiliary.

Suitable reaction auxiliaries are generally the customary inorganic or organic bases or acid acceptors. These preferably include the acetates, amides, carbonates, hydrogen carbonates, hydrides, hydroxides or alkoxides of alkali metals or alkaline earth metals, for example sodium acetate, potassium acetate, calcium acetate, lithium amide, sodium amide, potassium amide, calcium amide, sodium carbonate, potassium carbonate, calcium carbonate, sodium hydrogen carbonate, potassium hydrogen carbonate, calcium hydrogen carbonate, lithium hydride, sodium hydride, potassium hydride, calcium hydride, lithium hydroxide, sodium hydroxide, potassium hydroxide, calcium hydroxide, sodium methoxide, potassium methoxide, sodium ethoxide, potassium ethoxide, sodium n- or iso-propoxide, potassium n- or iso-propoxide, sodium n-, iso, sec- or tert-butoxide or potassium n-, iso-, sec- or tert-butoxide; furthermore also basic organic nitrogen compounds, for example trimethylamine, triethylamine, tripropylamine, tributylamine, ethyldiisopropylamine, N,N-dimethylcyclohexylamine, dicyclohexylamine, ethyldicyclohexylamine, N,N-dimethylaniline, N,N-dimethylbenzylamine, pyridine, 2-methyl-, 3-methyl-, 4-methyl-, 2,4-dimethyl-, 2,6-dimethyl-, 3,4-dimethyl- and 3,5-dimethylpyridine, 5-ethyl-2-methylpyridine, 4-dimethylaminopyridine, N-methylpiperidine, 1,4-diazabicyclo[2,2,2]octane (DABCO), 1,5-diazabicyclo[4,3,0]non-5-ene (DBN) or 1,8 diazabicyclo[5,4,0]undec-7-ene (DBU).

Process ($C_)$) according to the invention and processes ($A_)$) and ($B_)$) for the preparation of the compound of the formula (I) are preferably carried out in the presence of a diluent.

Suitable diluents are, in general, the customary organic solvents. These preferably include aliphatic, alicyclic and aromatic unhalogenated or halogenated hydrocarbons, for example pentane, hexane, heptane, petroleum ether, ligroin, benzine, benzene, toluene, xylene, chlorobenzene, dichlorobenzene, cyclohexane, methylcyclohexane, dichloromethane (methylene chloride), trichloromethane (chloroform) or tetrachloromethane, dialkyl ethers such as diethyl ether, diisopropyl ether, methyl tert-butyl ether (MTBE), ethyl tert-butyl ether, methyl tert-pentyl ether (TAME), ethyl tert-pentyl ether, tetrahydrofuran (THF), 1,4-dioxane, ethylene glycol dimethyl ether, ethylene glycol diethyl ether, diethylene glycol dimethyl ether and diethylene glycol diethyl ether; dialkyl ketones such as acetone, butanone (methyl ethyl ketone), methyl isopropyl ketone and methyl isobutyl ketone; nitriles such as acetonitrile, propionitrile, butyronitrile and benzonitrile; amides such as N,N-dimethylformamide (DMF), N,N-dimethylacetamide, N-methylformanilide, N-methylpyrrolidone and hexamethylphosphoric triamide; esters such as methyl acetate, ethyl acetate, n-propyl acetate, isopropyl acetate, n-butyl acetate, isobutyl acetate and sec-butyl acetate; sulfoxides such as dimethyl sulfoxide; alkanols such as methanol, ethanol, n-propanol, isopropanol, n-, iso-, sec- and tert-butanol; glycol ethers, such as ethylene glycol monomethyl ether, ethylene glycol monoethyl ether, diethylene glycol monomethyl ether, diethylene glycol monoethyl ether; mixtures of these with water, or pure water.

When carrying out processes ($B_j$) and ($C_j$), the reaction temperatures can be varied within a substantial range. In general, the process is carried out at temperatures from 0 to 200° C., preferably at 10 to 150° C., in particular at 20° C. to the boiling point of the reaction mixture in question.

To carry out processes ($A_j$), ($B_j$) and ($C_j$), the starting materials are generally employed in approximately equimolar amounts. However, it is also possible to employ in each case one of the components in a larger excess, approximately up to twice the molar amount of the other component.

Processes ($A_j$), ($B_j$) and ($C_j$) are expediently carried out under atmospheric pressure or under the inherent pressure of the reaction mixture in question. However, the processes may also be carried out under elevated or reduced pressure, in general at 0.1 to 10 bar.

The reaction mixtures in question are generally worked up by methods known per se, for example by diluting the reaction solution with water and subsequently isolating the product by means of filtration, crystallization or solvent extraction, or by removing the solvent, partitioning the residue in a mixture of water and a suitable organic solvent and working up the organic phase to arrive at the product.

In general, the 1-aryl-4-thiotriazines I can be prepared by one of the abovementioned synthetic processes. However, for economic or process engineering reasons, it may be more expedient to synthesize some compounds I from similar 1-aryl-4-thiotriazines—which, however, differ in particular with regard to the meanings of the radicals $R^5$—, in a manner known per se, for example by hydrolysis, esterification, transesterification, amidation, acetalization, acetal hydrolysis, condensation reaction, Wittig reaction, Peterson olefination, etherification, alkylation, oxidation or reduction.

The preparation of the 1-aryl-4-thiotriazines I may lead to them being obtained as isomer mixtures; if desired, however, these can be resolved by the methods customary for this purpose, such as crystallization or chromatography, also on an optically active absorbate, to give the pure isomers. Pure optically active isomers can be synthesized advantageously from the corresponding optically active starting materials.

Agriculturally useful salts of the compounds I can be formed by reaction with a base of the cation in question, preferably an alkali metal hydroxide or alkali metal hydride, or by reaction with an acid of the anion in question, preferably of hydrochloric acid, hydrobromic acid, sulfuric acid, phosphoric acid or nitric acid.

Salts of I whose metal ion is not an alkali metal ion can also be prepared in the customary manner by double decomposition of the alkali metal salt in question, and ammonium, phosphonium, sulfonium and sulfoxonium salts by means of ammonia, phosphonium hydroxide, sulfonium hydroxide or sulfoxonium hydroxide.

The compounds I and their agriculturally useful salts—as mixtures of isomers and also in the form of the pure isomers—are suitable for use as herbicides. The herbicidal compositions comprising I effect very good vegetation control on noncrop areas in particular at elevated rates of application. They effect very efficient control of broad-leaved weeds and grass weeds in crops such as wheat, rice, maize, soya and cotton without harming the crop plants to a significant extent. This effect is particularly pronounced at low rates of application.

Depending on the method of application in question, the compounds I, or herbicidal compositions comprising them, can also be employed in a further number of crop plants for eliminating undesirable plants. The following are examples of suitable crops:

Allium cepa, Ananas comosus, Arachis hypogaea, Asparagus officinalis, Beta vulgaris spec. altissima, Beta vulgaris spec. rapa, Brassica napus var. napus, Brassica napus var. napobrassica, Brassica rapa var. silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus spec., Manihot esculenta, Medicago sativa, Musa spec., Nicotiana tabacum (N.rustica), Olea europaea, Oryza sativa, Phaseolus lunatus, Phaseolus vulgaris, Picea abies, Pinus spec., Pisum sativum, Prunus avium, Prunus persica, Pyrus communis, Ribes sylvestre, Ricinus communis, Saccharum officinarum, Secale cereale, Solanum tuberosum, Sorghum bicolor (s. vulgare), Theobroma cacao, Trifolium pratense, Triticum aestivum, Triticum durum, Vicia faba, Vitis vinifera and Zea mays.

Moreover, the compounds I can also be employed in crops which have been rendered tolerant to the action of herbicides by means of breeding, including genetic engineering methods.

The compounds I, or the herbicidal compositions comprising them, can be used, for example, in the form of ready-to-spray aqueous solutions, powders, suspensions, also high-percentage aqueous, oily or other suspensions or dispersions, emulsions, oil dispersions, pastes, dusts, materials for spreading or granules, by means of spraying, atomizing, dusting, spreading or pouring. The use forms depend on the intended aims; in any case, they should guarantee the finest possible distribution of the active ingredients according to the invention.

Suitable inert auxiliaries are essentially: mineral oil fractions of medium to high boiling point, such as kerosene and diesel oil, furthermore coal tar oils and oils of vegetable or animal origin, aliphatic, cyclic and aromatic hydrocarbons, e.g. paraffins, tetrahydronaphthalene, alkylated naphthalenes and their derivatives, alkylated benzenes and their derivatives, alcohols, such as methanol, ethanol, propanol, butanol and cyclohexanol, ketones, such as cyclohexanone, strongly polar solvents, e.g. amines, such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the 1-aryl-4-thiotriazines I, either as such or dissolved in an oil or solvent, can be homogenized in water by means of a wetting agent, tackifier, dispersant or emulsifier. Alternatively, it is possible to prepare concentrates comprising active ingredient, wetting agent, tackifier, dispersant or emulsifier and, if desired, solvent or oil, which are suitable for dilution with water.

Suitable surfactants are the alkali metal salts, alkaline earth metal salts and ammonium salts of aromatic sulfonic acids, e.g. ligno-, phenol-, naphthalene- and dibutylnaphthalenesulfonic acid, and of fatty acids, alkyl- and alkylarylsulfonates, alkyl, lauryl ether and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl polyglycol ether, tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors or methylcellulose.

Powders, materials for spreading and dusts can be prepared by mixing or grinding the active ingredients together with a solid carrier.

Granules, e.g. coated granules, impregnated granules and homogeneous granules, can be prepared by binding the active ingredients to solid carriers. Solid carriers are mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers, such as ammonium sulfate, ammonium phosphate, ammonium nitrate, ureas, and products of vegetable origin, such as cereal meal, tree bark meal, wood meal and nutshell meal, cellulose powders, or other solid carriers.

The concentrations of the active ingredients I in the ready-to-use products can be varied within wide ranges. In general, the formulations comprise from about 0.001 to 98% by weight, preferably 0.01 to 95% by weight, of at least one active ingredient. The active ingredients are employed in a purity of 90% to 100%, preferably 95% to 100% (according to NMR spectrum).

The following formulation examples illustrate the preparation of such products:

I. 20 parts by weight of compound No. 3 are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

II. 20 parts by weight of compound No. 5 are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

III. 20 parts by weight of active ingredient No. 12 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

IV. 20 parts by weight of active ingredient No. 32 are mixed thoroughly with 3 parts by weight of sodium diisobutylnaphthalene-α-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture comprising 0.1% by weight of the active ingredient.

V. 3 parts by weight of active ingredient No. 36 are mixed with 97 parts by weight of finely divided kaolin. This gives a dust comprising 3% by weight of the active ingredient.

VI. 20 parts by weight of active ingredient No. 41 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of the compound No. 42 is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII. 1 part by weight of the compound No. 64 is dissolved in a mixture composed of 80 parts by weight of cyclohexanone and 20 parts by weight of Wettol® EM 31 (=nonionic emulsifier based on ethoxylated castor oil; BASF AG). This gives a stable emulsion concentrate.

The active ingredients I or the herbicidal compositions can be applied pre- or post-emergence. If the active ingredients are less well tolerated by certain crop plants, application techniques may be used in which the herbicidal compositions are sprayed, with the aid of the spraying equipment, in such a way that they come into contact as little as possible, if at all, with the leaves of the sensitive crop plants, while the active ingredients reach the leaves of undesirable plants growing underneath, or the naked soil surface (post-directed, lay-by).

The application rates of active ingredient I are from 0.001 to 3.0, preferably 0.01 to 1.0, kg of active ingredient (a.i.) per ha, depending on the control target, the season, the target plants and the growth stage.

To widen the spectrum of action and to achieve synergistic effects, the 1-aryl-4-thiotriazines I may be mixed with a large number of representatives of other groups of herbicidal or growth-regulating active ingredients and then applied concomitantly. Suitable components for mixtures are, for example, 1,2,4-thiadiazoles, 1,3,4-thiadiazoles, amides, aminophosphoric acid and its derivatives, aminotriazoles, anilides, aryloxy-/hetaryloxyalkanoic acids and their derivatives, benzoic acid and its derivatives, benzothiadiazinones, 2-(hetaroyl/aroyl)-1,3-cyclohexanediones, hetaryl aryl ketones, benzylisoxazolidinones, meta-CF$_3$-phenyl derivatives, carbamates, quinolin carboxylic acid and its derivatives, chloroacetanilides, cyclohexane-1,3-dione derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonyl ureas, triazines, triazinones, triazolinones, triazolcarboxamides and uracils.

Furthermore, it may be advantageous to apply the compounds I, alone or in combination with other herbicides, together as a mixture with further crop protection agents, for example with pesticides or agents for controlling phytopathogenic fungi or bacteria. Also of interest is the miscibility with mineral salt solutions which are employed for treating nutrient and trace element deficiencies. Nonphytotoxic oils and oil concentrates may also be added.

PREPARATION EXAMPLE

Example 1

Compound No. 38

3-(2,4-difluorophenyl)-1,5-dimethyl-6-thioxo-[1,3,5]triazinane-2,4-dione

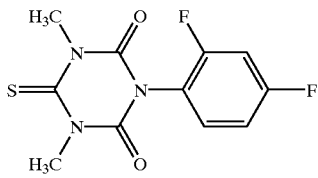

31 g of 2,4-difluorophenyl isocyanate and 64.9 g of carbodiimidazole were added in succession to 20.8 g of N,N'-dimethylthiourea in 500 ml of toluene and 1 ml of triethylamine. This mixture was stirred first for 3 hours at 60–65° C. and then for 12 hours at 80–85° C. After cooling to room temperature, the mixture was washed three times with 100-ml-portions of water, and the organic phase was dried over sodium sulfate. After distillation of the low-boiling fractions, 48 g of the desired product of melting point 156–159° C. remained.

Example 2

Compound No. 40

2-Chloro-5-(3,5-dimethyl-2,6-dioxo-4-thioxo-[1,3,5]triazinan-1-yl)-benzaldehyde O-ethyl oxime

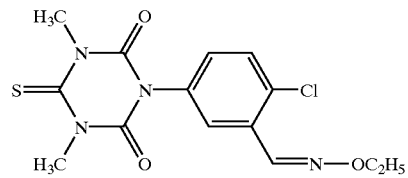

2.8 g of 3-ethoxyiminoethyl-4-chlorophenyl isocyanate and 4 g of carbodiimidazole were added in succession to 1.3 g of N,N'-dimethylurea in 20 ml of toluene and 0.4 ml of triethylamine. This mixture was stirred first for 2 hours at 60° C and then for 4 hours at 80° C. After cooling to room temperature, the mixture was washed four times with 20-ml-portions of water, and the organic phase was dried over sodium sulfate. The residue which remained after the solvent had been distilled off was purified by chromatography on silica gel (mobile phase: cyclohexane/ethyl acetate). Yield: 2.02 g; m.p.: 139–141° C.

Example 3

Compound No. 1

3-(4-Chloro-2-fluoro-5-hydroxyphenyl)-1,5-dimethyl-6-thioxo-[1,3,5]triazinane-2,4-dione

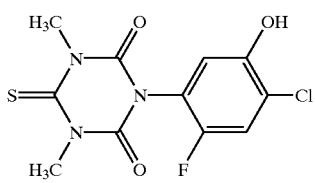

3 ml of triethylamine and then a solution of 22.4 g (91.2 mmol) of 4-chloro-2-fluoro-5-(methoxycarbonyloxy)phenyl isocyanate in 100 ml of toluene were added dropwise at approximately 20° C. to a solution of 9.5 g (91.2 mmol) of N,N'-dimethylthiourea in 20 ml of toluene. After addition of 29.6 g (182.5 mmol) of carbodiimidazole, the mixture was heated for 3 hours at 80° C. The reaction mixture was stirred overnight at approximately 20° C., then washed three times with water and finally concentrated under reduced pressure. The crude product was purified by column chromatography (mobile phase: cyclohexane/ethyl acetate=10:1). Yield: 18.1 g (63%); m.p.: 242–246° C.

Example 4

Compound No. 11

Allyl 2-[2-chloro-5-(3,5-dimethyl-2,6-dioxo-[1,3,5]triazinan-1-yl)-4-fluorophenoxy]propionate (racemate)

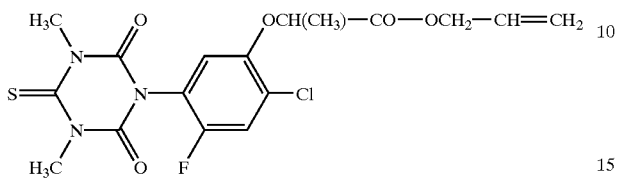

0.37 g (2.65 mmol) of $K_2CO_3$ and 0.51 g (2.65 mmol) of rac. allyl 2-bromopropionate were added approximately at 20° C. to a solution of 0.80 g (2.52 mmol) of 3-(4-chloro-2-fluoro-5-hydroxyphenyl)-1,5-dimethyl-6-thioxo-[1,3,5]triazinane-2,4-dione in 15 ml of dimethylformamide. After the reaction mixture had been stirred for two hours at approximately 20° C., it was stirred into ice-water. The product was extracted three times with methyl tert-butyl ether. The combined organic phases were dried over magnesium sulfate and then concentrated. The crude product (1.18 g) was purified by column chromatography (mobile phase: cyclohexane/ethyl acetate=15:1). Yield: 0.88 g (81%); $^1$H NMR (270 MHz, in $CDCl_3$): δ[ppm]=1.7 (d, 3H), 3.8 (s, 6H), 4.6 (m, 2H), 4.7 (q, 1H), 5.2 (d, 1H), 5.3 (d, 1H), 5.9 (m, 1H), 6.9 (d, 1H), 7.3 (d, 1H).

Example 5

Compound No. 12

Allyl (R)-2-[2-chloro-5-(3,5-dimethyl-2,6-dioxo-[1,3,5]triazinan-1-yl)-4-fluorophenoxy]propionate (R isomer)

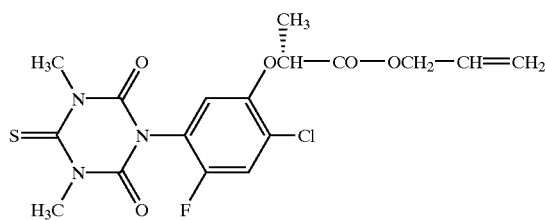

0.38 g (1.89 mmol) of diisopropyl azodicarboxylate was added dropwise at 0° C. in the course of 5 minutes to a solution of 0.50 g (1.58 mmol) of 3-(4-chloro-2-fluoro-5-hydroxyphenyl)-1,5-dimethyl-6-thioxo-[1,3,5]triazinane-2,4-dione, 0.20 g (1.58 mmol) of allyl S-lactate and 0.48 g (1.81 mmol) of triphenylphosphine. Then, the mixture was stirred for 2 hours at 0–5° C., whereupon the reaction mixture was concentrated under reduced pressure. The crude product was taken up in methylene chloride. The resulting solution was washed twice with water, then dried over magnesium sulfate and finally concentrated. The crude product (1.88 g) was purified by column chromatography (mobile phase: cyclohexane/ethyl acetate=9:1). Yield: 0.64 g (94%); $^1$H NMR see Example 4.

Example 6

Compound No. 24

Cyclobutylmethyl (R)-2-[2-chloro-5-(3,5-dimethyl-2,6-dioxo-4-thioxo-[1,3,5]triazinan-1-yl)-4-fluorophenoxy]propionate (R isomer)

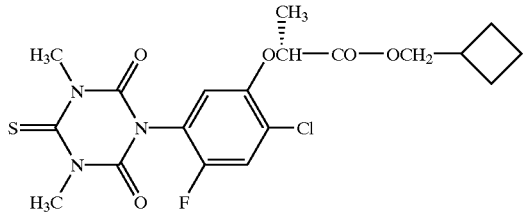

36 mg (0.125 mmol, 10 mol%) of $Ti[OCH(CH_3)_2]_4$ were added to a solution of 504 mg (1.25 mmol) of methyl (R)-2-[2-chloro-5-(3,5-dimethyl-2,6-dioxo-[1,3,5]triazinan-1-yl)-4-fluorophenoxy]-propionate in 10 ml of cyclobutylmethanol. The resulting mixture was heated for 5 hours at reflux temperature, whereupon the reaction mixture was poured into ice-water. The product of value which had formed was extracted with ethyl acetate (4 times). The combined organic phases were subsequently dried over magnesium sulfate and then concentrated. The resulting crude product was purified by column chromatography (mobile phase: cyclohexane/ethyl acetate=25:1). Yield: 410 mg (72%);
$^1$H NMR (400 MHz, in $CDCl_3$): δ[ppm]=1.7 (d, 3H), 1.7 (m, 2H), 1.85 (m, 2H), 2.0 (m, 2H), 2.6 (quint., 1H), 3.8 (2s, je 3H), 4.1 (m, 2H), 4.7 (q, 1H), 6.9 (d, 1H), 7.35 (d, 1H).

Example 7

Compound No. 28

2-Chloro-5-(3,5-dimethyl-2,6-dioxo-4-thioxo-[1,3,5]triazinan-1-yl)-4-fluorobenzoic acid

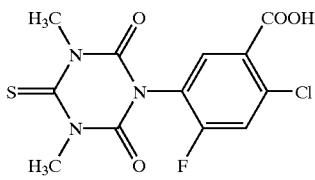

Method A:

4.98 g (12.9 mmol) of isopropyl 2-chloro-5-(3,5-dimethyl-2,6-dioxo-4-thioxo-[1,3,5]triazinan-1-yl)-4-fluorobenzoate and 25 ml of concentrated sulfuric acid were heated for 7 hours at 80° C. Then, the reaction mixture was carefully poured into ice-water. The solid fraction which had formed was separated off and washed with water until neutral. After drying, 2.62 g (59%) of the desired acid were obtained; m.p. 225–229° C.

Method B:

108 mg (0.30 mmol) of methyl 2-chloro-5-(3,5-dimethyl-2,6-dioxo-4-thioxo-[1,3,5]triazinan-1-yl)-4-fluorobenzoate and 150 mg (0.75 mmol) of iodotrimethylsilane were heated for 2 hours at 100° C. After cooling, methyl tert-butyl ether and saturated aqueous sodium hydrogen carbonate solution were added to the reaction mixture (to pH 8). The aqueous phase was subsequently separated off and acidified with 10% strength hydrochloric acid (pH 5). It was then extracted three times with methylene chloride. The combined methylene chloride phases were then dried over magnesium sulfate and finally concentrated. Yield: 70 mg (67%); m.p. 225–229° C.

In Table 3 which follows, other 1-aryl-4-thiotriazines of the formula I which were, or can be, prepared in a similar manner are listed in addition to the active ingredients described above:

TABLE 3

I ($R^1$, $R^2$ = $CH_3$; Y = CH)

| No. | $R^3$ | $R^4$ | $R^5$ | M.p. or HPLC/MS*) |
|---|---|---|---|---|
| 1 | F | Cl | OH | 242–246° C. |
| 2 | F | Cl | $OCH_3$ | oil |
| 3 | F | Cl | $OCH_2$—C≡CH | 178–180° C. |
| 4 | F | Cl | $OCH(CH_3)$—C≡CH | oil |
| 5 | F | Cl | $OCH(CH_3)_2$ | oil |
| 6 | F | Cl | O-Cyclopentyl | 118–121° C. |
| 7 | F | Cl | $OCH_2$—CO—$OCH_3$ | oil |
| 8 | F | Cl | $OCH_2$—CO—$OCH_2$—CH=$CH_2$ | oil |
| 9 | F | Cl | $OCH(CH_3)$—CO—$OCH_3$ (rac.) | oil |
| 10 | F | Cl | $OCH(CH_3)$—CO—$OCH_3$ (R) | oil |
| 11 | F | Cl | $OCH(CH_3)$—CO—$OCH_2$—CH=$CH_2$ (rac.) | oil |
| 12 | F | Cl | $OCH(CH_3)$—CO—$OCH_2$—CH=$CH_2$ (R) | oil |
| 13 | F | Cl | $OCH(CH_3)$—CO—$OCH_2$—CH=$CHCH_3$ (R) | oil |
| 14 | F | Cl | $OCH(CH_3)$—CO—$OCH_2CH_2$—CH=$CH_2$ (R) | oil |
| 15 | F | Cl | $OCH(CH_3)$—CO—$OCH_2$—CH=$C(CH_3)_2$ (R) | oil |
| 16 | F | Cl | $OCH(CH_3)$—CO—$OCH_2$—C≡CH (rac.) | oil |
| 17 | F | Cl | $OCH(CH_3)$—CO—$OCH_2$—C≡CH (R) | oil |
| 18 | F | Cl | $OCH(CH_3)$—CO—$OCH_2CH_2$—C≡CH (R) | oil |
| 19 | F | Cl | $OCH(CH_3)$—CO—O-Cyclopentyl (R) | 85–86° C. |
| 20 | F | Cl | $OCH(CH_3)$—CO—$OCH_2CH_2$—$OCH_3$ (rac.) | oil |
| 21 | F | Cl | $OCH(CH_3)$—CO—$OCH_2CH_2$—$OCH_3$ (R) | oil |
| 22 | F | Cl | $OCH(CH_3)$—CO—$OCH_2CH_2$—$OC_2H_5$ (R) | oil |
| 23 | F | Cl | $OCH(CH_3)$—CO—$OCH_2$-Cyclopropyl (R) | oil |
| 24 | F | Cl | $OCH(CH_3)$—CO—$OCH_2$-Cyclobutyl (R) | oil |
| 25 | F | Cl | $OCH(CH_3)$—CO—NH—$CH_3$ (R) | 150–154° C. |
| 26 | F | Cl | $OCH(CH_3)$—CO—$N(CH_3)_2$ (R) | oil |
| 27 | F | Cl | $OC(CH_3)_2$—CO—$OCH_2$—CH=$CH_2$ | oil |
| 28 | F | Cl | COOH | 225–229° C. |
| 29 | F | Cl | CO—$OCH(CH_3)_2$ | oil |
| 30 | F | Cl | CO—$OCH_2$—CH=$CH_2$ | oil |
| 31 | F | Cl | CHO | 136–139° C. |
| 32 | F | Cl | CH=N—$OCH_3$ | 156–160° C. |
| 33 | F | Cl | CH=C(Cl)—CO—$OC_2H_5$ | 177–182° C. |
| 34 | F | CN | F | 180–184° C. |
| 35 | F | CN | OH | 252–255° C. |
| 36 | F | CN | $OCH_3$ | 208–210° C. |
| 37 | F | CN | $OCH(CH_3)$—CO—$OCH_3$ (rac.) | 165–168° C. |
| 38 | F | F | H | 156–159° C. |
| 39 | H | Cl | H | 202–205° C. |
| 40 | H | Cl | CH=N—$OC_2H_5$ | 139–141° C. |
| 41 | H | Cl | CO—$OCH(CH_3)_2$ | 132–136° C. |
| 42 | H | Cl | CH=C(Cl)—CO—$OC_2H_5$ | 212–218° C. |
| 43 | H | Cl | CH=C(Cl)—CO—$OCH_2$—CH=$CH_2$ | 171–173° C. |
| 44 | F | Cl | $OCH_2$—CO—$CH_3$ | M = 374, t = 3.91 |
| 45 | F | Cl | $OCH_2$—CO—$C(CH_3)_3$ | M = 416, t = 5.07 |
| 46 | F | Cl | $OCH_2$—CO-cyclopropyl | M = 400, t = 4.17 |
| 47 | F | Cl | $OCH_2$—CO-phenyl | M = 436, t = 5.07 |
| 48 | F | Cl | $OCH_2$—CO-(4-fluorophenyl) | M = 454, t = 4.45 |
| 49 | F | Cl | $OCH_2$—CO-(4-chlorophenyl) | M = 470, t = 5.24 |
| 50 | F | Cl | $OCH_2$—CO-(4-bromophenyl) | M = 515, t = 4.70 |
| 51 | F | Cl | $OCH_2$—CO-(4-cyanophenyl) | M = 461, t = 5.01 |
| 52 | F | Cl | $OCH_2$—CO-(4-methoxyphenyl) | M = 466, t = 5.09 |
| 53 | F | Cl | $OCH_2$—CO-(4-nitrophenyl) | M = 481, t = 5.08 |
| 54 | F | Cl | $OCH_2$—CO-(2-nitrophenyl) | M = 481, t = 4.39 |
| 55 | F | Cl | $OCH_2$—CO-(3-nitrophenyl) | M = 481, t = 4.40 |
| 56 | F | Cl | $OCH_2$—CO-(3-methoxyphenyl) | M = 466, t = 4.46 |
| 57 | F | Cl | $OCH_2$—CO-(2,4-dichlorophenyl) | M = 505, t = 4.82 |
| 58 | F | Cl | $OCH_2$—CO-(2,4-dibromophenyl) | M = 594, t = 4.88 |
| 59 | F | Cl | $OCH_2$—CO-(2,4-dimethoxyphenyl) | M = 496, t = 4.52 |
| 60 | F | Cl | $OCH_2$—CO-(3,4-dichlorophenyl) | M = 505, t = 4.83 |
| 61 | F | Cl | $OCH_2$—CO-(2,3,4-trichlorophenyl) | M = 539, t = 4.97 |
| 62 | F | Cl | $OCH_2$—CO-(2,4-dichloro-3-methyl-phenyl) | M = 519, t = 4.97 |
| 63 | F | Cl | $OCH(CH_3)$—CO-phenyl (rac.) | M = 450, t = 4.58 |

*)HPLC/MS conditions: column GROM-SIL 80, ODS-7 pH, 4 μm, 40 × 2 mm; flow rate 0.7 ml/min, UV detector

Example 8

Compound No. 64

3(4-Chloro-2-cyclopropyl-6-fluorobenzoxazol-7-yl)-1,5-dimethyl-6-thioxo-[1,3,5]triazinane-2,4-dione
($R^6$=cyclopropyl)

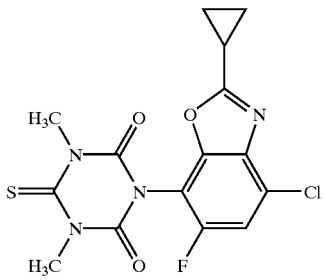

A mixture of 370 mg (1.11 mmol) of 3-(3-amino-4-chloro-6-fluoro-2-hydroxyphenyl)-1,5-dimethyl-6-thioxo-[1,3,5]triazinane-2,4-dione and 226 mg (1.67 mmol) of imidomethyl cyclopropanate hydrochloride in 20 ml of methanol (distilled off over Na) was stirred for 2 hours at approximately 20° C. The mixture was subsequently concentrated. The residue was slaked in water, whereupon the undissolved components were separated off and dissolved in ethyl acetate. The ester phase was dried over magnesium sulfate and then concentrated under reduced pressure. This gave 160 mg of crude product which was purified by column chromatography (mobile phase: cyclohexane/ethyl acetate=20:1). Yield: 90 mg (21%); oil;

$^1$H NMR (400 MHz, in CDCl$_3$): δ[ppm]=1.2–1.35 (m, 4H), 2.2 (m, 1H), 3.8 (s, 6H), 7.15 (d, 1H).

Precursor 8α

3-(3-Amino-4-chloro-6-fluoro-2-hydroxyphenyl)-1,5-dimethyl-6-thioxo-[1,3,5]triazinane-2,4-dione

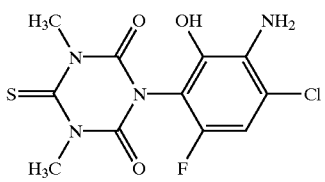

0.46 g (1.33 mmol) of 3-(3-amino-4-chloro-6-fluoro-2-methoxyphenyl)-1,3-dimethyl-6-thioxo-[1,3,5]triazinane-2,4-dione in 5 ml of methylene chloride was added dropwise at 0° C. to 8 ml of a 1M solution of boron tribromide in methylene chloride (=8 mmol BBr$_3$). The reaction mixture was subsequently stirred for two hours at 0° C., whereupon it was slowly stirred into ice-water. The product of value was extracted from the aqueous phase using methylene chloride (twice). The combined organic phases were dried over magnesium sulfate and then concentrated under reduced pressure. This gave 0.21 g (48%) of the product of value.

The aqueous phase was brought to pH 10 using sodium hydroxide solution. Then, the mixture was reextracted with methylene chloride. Again, the methylene chloride phases were dried over magnesium sulfate and concentrated. This gave a further 0.16 g (36%) of the product of value.

Overall yield: 84%;

$^1$H NMR (270 MHz, in CDCl$_3$): δ[ppm]=3.8 (s, 6H), 6.9 (d, 1H).

Precursor 8β

3-(3-Amino-4-chloro-6-fluoro-2-methoxyphenyl)-1,3-dimethyl-6-thioxo-[1,3,5]triazinane-2,4-dione

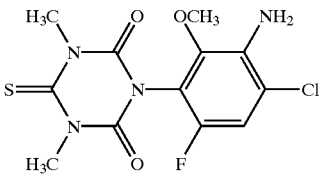

A mixture of 0.22 g (3.98 mmol) of iron powder and 2.5 ml of acetic acid in 5 ml of methanol was heated at reflux temperature. At this temperature, a suspension of 0.50 g (1.33 mmol) of 3-(4-chloro-6-fluoro-2-methoxy-3-nitrophenyl)-1,5-dimethyl-6-thioxo-[1,3,5]triazinane-2,4-dione in 3 ml of methanol was slowly added dropwise to the reaction mixture. The mixture was subsequently stirred for two hours at reflux temperature. After the reaction mixture had been cooled and concentrated, the crude product was filtered over silica gel (mobile phase: ethyl acetate). The filtrate was concentrated under reduced pressure. After drying, 0.45 g (98%) of the product of value were obtained;

$^1$H NMR (400 MHz, in CDCl$_3$): δ[ppm]=3.75 (s, 3H), 3.8 (s, 6H), 4.05 (bs, 2H), 7.05 (d, 1H).

Precursor 8γ

3-(4-Chloro-6-fluoro-2-methoxy-3-nitrophenyl)-1,5-dimethyl-6-thioxo-[1,3,5]triazinane-2,4-dione

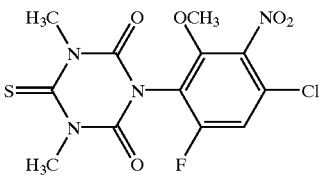

A solution of 3.0 g (15.0 mmol) of diphosgene in 5 ml of toluene was added dropwise at approximately 20° C. to a solution of 3.0 g (13.6 mmol) of 4-chloro-6-fluoro-2-methoxy-3-nitrophenylamine in 15 ml of toluene. Then, the mixture was slowly heated to reflux temperature and stirred for 6 hours under reflux. After the reaction mixture had been concentrated and dried, the crude isocyanate was redissolved in 5 ml of toluene to be used in the next reaction. 6 ml of triethylamine and a solution of 3.55 g (14.4 mmol) of dimethylthiourea were added dropwise to this solution at approximately 20° C. 4.7 g (28.8 mmol) of carbonyldiimidazole were subsequently added to the reaction mixture. The mixture was heated at 80° C. for 5 hours and then allowed to cool. For work-up, it was firstly washed four times with water. Then, the organic phase was dried over magnesium sulfate and concentrated under reduced pressure. The crude product (6.58 g) was purified by silica gel chromatography (mobile phase: cyclohexane/ethyl acetate=10:1). Yield: 1.31 g (24%);

$^1$H NMR (270 MHz, in CDCl$_3$): δ[ppm]=3.8 (s, 6H), 3.9 (s, 3H), 7.2 (d, 1H).

Precursor 8δ

4-Chloro-6-fluoro-2-methoxy-3-nitrophenylamine

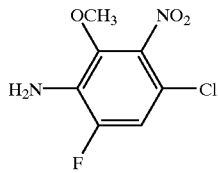

A suspension of 40.0 g (152 mmol) of N-(4-chloro-6-fluoro-2-methoxy-3-nitrophenyl)acetamide in 800 ml of 6M hydrochloric acid was heated for 5 hours at reflux temperature, whereupon the mixture was stirred overnight at approximately 20° C. For work-up, the reaction mixture was stirred into ice-water. The pH was brought to 8–9 by adding sodium solution. The mixture was subsequently extracted six times with ethyl acetate. The combined organic phases were dried over magnesium sulfate and then concentrated under reduced pressure. Yield: 33 g (98%);

$^1$H NMR (270 MHz, in CDCl$_3$): δ[ppm]=3.9 (s, 3H), 4.0 (bs, 2H), 7.0 (d, 1H).

Precursor 8ε

N-(4-Chloro-6-fluoro-2-methoxy-3-nitrophenyl)acetamide

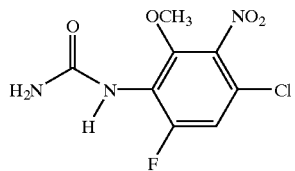

A solution of 72.5 g (647 mmol) of NaOSi(CH$_3$)$_3$ in 25 ml of tetrahydrofuran was added dropwise at approximately 20° C. to a solution of 81 g (323 mmol) of N-(4-chloro-2,6-difluoro-3-nitro-phenyl)acetamide in 490 ml of dioxane and 50 ml of methanol. The mixture was subsequently heated for two hours at reflux temperature. After cooling and concentrating, the crude product (black oil) was stirred into ice-cold 10% strength hydrochloric acid. The resulting product of value was then extracted with ethyl acetate (3 times). The combined organic phases were dried over magnesium sulfate and concentrated under reduced pressure. The residue was stirred once with water. The insoluble components were removed and washed three times with water. After drying, 52.1 g (63%) of the product of value were obtained.

$^1$H NMR (270 MHz, in d$^6$ dimethyl sulfoxide): δ[ppm]= 2.1 (s, 3H), 3.85 (s, 3H), 7.75 (d, 1H), 9.9 (bs, 1H).

Precursor 8ζ

N-(4-Chloro-2,6-difluoro-3-nitrophenyl)acetamide

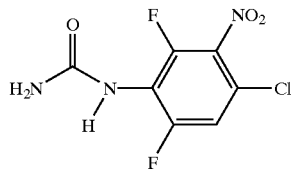

30.7 g (487 mmol) of concentrated nitric acid were added dropwise at 0–5° C. to a solution of 100 g (487 mmol) of N-(4-chloro-2,6-difluorophenyl)acetamide in 500 ml of concentrated sulfuric acid. After the reaction mixture had been stirred for one hour at 0–5° C., it was stirred into ice-water. The resulting solid was separated off, washed twice with water and dried. Yield: 81.3 g (72%);

$^1$H NMR (270 MHz, in d$^6$ dimethyl sulfoxide): δ[ppm]= 2.1 (s, 3H), 7.95 (dd, 1H), 10.2 (bs, 1H).

Precursor 8θ

N-(4-Chloro-2,6-difluorophenyl)acetamide

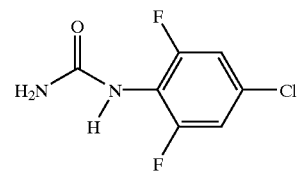

126 g (930 mmol) of sulfuryl chloride were added dropwise at 80° C. to a solution of 100 g (775 mmol) of difluoroaniline in 700 ml of glacial acetic acid. The mixture was subsequently stirred for three hours at 100° C. After cooling and concentration, the residue was treated with 200 ml of acetic anhydride. The mixture was then stirred overnight at approximately 20° C. For work-up, the reaction mixture was stirred into 1.5 l of ice-water. The product of value was extracted from the aqueous phase using ethyl acetate (3 times). The combined organic phases were dried over magnesium sulfate and concentrated under reduced pressure. Yield: 163 g;

$^1$H NMR (270 MHz, in d$^6$ dimethyl sulfoxide): δ[ppm]= 2.05 (s, 3H), 7.4 (d, 2H), 9.8 (bs, 1H).

The following were prepared similarly:

Compound No. 65

3-(4-chloro-6-fluorobenzoxazol-7-yl)-1,5-dimethyl-6-thioxo-[1,3,5]triazinane-2,4-dione (R$^6$ =H; m.p.: 209–211° C.) and

Compound No. 66

3-(4-chloro-2-ethyl-6-fluorobenzoxazol-7-yl)-1,5-dimethyl-6-thioxo-[1,3,5]triazinane-2,4-dione (R$^6$= C$_2$H$_5$; m.p.: 156–159° C.).

Example 9

Compound No. 67

3-(4-Chloro-6-fluorobenzoxazol-7-yl)-1,5-dimethyl-6-thioxo-[1,3,5]triazinane-2,4-dione (R$^6$=hydrogen)

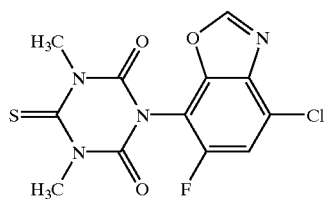

5.0 g (48.1 mmol) of trimethylformamide were added dropwise to a solution of 502 mg (1.50 mmol) of 3-(3-amino-4-chloro-6-fluoro-2-hydroxyphenyl)-1,5-dimethyl- 6-thioxo-[1,3,5]-triazinane-2,4-dione in 10 ml of methanol. The mixture was then heated at reflux temperature for 9 hours. The reaction mixture was subsequently concentrated under reduced pressure. The resulting crude product was purified by means of column chromatography (mobile phase: cyclohexane/ethyl acetate=20:1). Yield: 240 mg (46%); m.p.: 209–211° C.

Compound No. 68

3-(4-chloro-2-ethyl-6-fluorobenzoxazol-7-yl)-1,5-dimethyl-6-thioxo-[1,3,5]triazinane-2,4-dione ($R^6$=ethyl) was prepared in a similar manner.

Use Examples

The herbicidal action of 1-aryl-4-thiotriazines I was demonstrated by the following greenhouse experiments:

The culture vessels used were plastic flower pots containing, as substrate, loamy sand with approximately 3.0% humus. The seeds of the test plants were sown separately for each species.

For the pre-emergence treatment, the active ingredients which were suspended or emulsified in water were applied directly after sowing using finely distributing nozzles. The containers were irrigated gently to promote germination and growth and subsequently covered with translucent plastic hoods until the plants had rooted. This cover causes uniform germination of the test plants, unless this was adversely affected by the active ingredients.

For the post-emergence treatment, the test plants were first grown to a height of 3 to 15 cm, depending on the plant habit, and only then treated with the active ingredients which were suspended or emulsified in water. For this purpose, the test plants were either sown directly and grown on in the same containers, or first grown separately as seedlings and transplanted into the experimental containers a few days before the treatment. The application rates for the post-emergence treatment was [sic] 125, 62.5, 7.81 and 3.91 g/ha of a.s. (active substance).

The plants were kept at temperatures from 10–25° C. or 20–35° C., depending on the species. The experimental period extended over 2 to 4 weeks. During this time, the plants were tended, and their response to the individual treatments was evaluated.

A scale from 0 to 100 was used for the evaluation. 100 means no emergence of the plants, or complete destruction of at least the aerial parts, while 0 means no damage, or normal growth.

The plants used in the greenhouse experiments were composed of the following species:

| Scientific name | Vernacular Name |
| --- | --- |
| Abutilon theophrasti | velvet leaf |
| Amaranthus retroflexus | redroot pigweed |
| Chenopodium album | lambsquarters (goosefoot) |
| Commelina benghalensis | bengal commelina; tropical spiderwort |
| Ipomoca species | morningglory |
| Setaria faberii | giant foxtail |
| Solanum nigrum | black nightshade |
| Veronica species | speedwell |

At application rates of 7.81 and 3.91 g/ha active substance, the active ingredient No. 30 controlled Amaranthus retroflexus, Chenopodium album, Commelina benghalensis and Setaria faberii considerably better by the post-emergence method than the comparison compound A

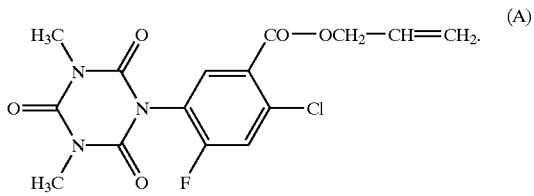

At application rates of 125 and 62.5 g/ha active substance, the active ingredient No. 39 showed a considerably better herbicidal action against Abutilon theophrasti, Chenopodium album, Ipomoea species, Solanum nigrum and Veronica species in the post-emergence method than the comparison compound B

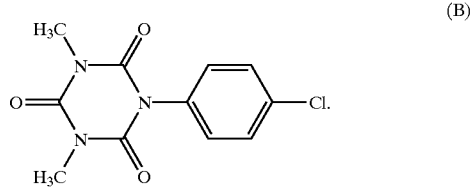

We claim:
1. A 1-aryl-4-thiotriazine of the formula I

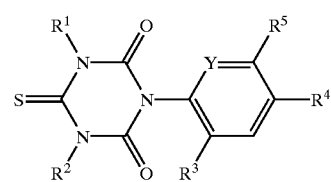

where the variables have the following meanings:
$R^1$ is methyl;
$R^2$ is methyl;
$R^3$ is hydrogen or halogen;
$R^4$ is cyano or halogen;
Y is the methine group;
$R^5$ is $C_1$–$C_6$-alkoxy, $C_1$–$C_6$-alkylthio, $C_3$–$C_6$-cycloalkoxy, $C_3$–$C_6$-cycloalkylthio, $C_2$–$C_6$-alkenyloxy, $C_2$–$C_6$-alkenylthio, $C_2$–$C_6$-alkynyloxy or $C_2$–$C_6$-alkynylthio, optionally substituted by one of the following substituents: halogen, cyano, —CO—$R^8$, —CO—$OR^8$ or —CO—N($R^8$)—$R^9$, —CO—$R^{11}$, —C($R^{11}$)($OR^{13}$)($OR^{14}$), —C($R^{11}$)=C($R^{15}$)—CO—$R^{16}$, —CH($R^{11}$)—CH($R^{15}$)—CO—$R^{16}$, —CO—$OR^{20}$, —C($R^{10}$)=N—$OR^7$, —N($R^{21}$)—$R^{22}$ or —CO—N($R^{21}$)—$R^{22}$;
$R^6$ is hydrogen, halogen, $C_1$–$C_6$-alkyl, $C_3$–$C_6$-alkenyl, $C_3$–$C_6$-alkynyl, $C_1$–$C_6$-alkoxy, $C_3$–$C_6$-alkenyloxy, $C_3$–$C_6$-alkynyloxy, $C_3$–$C_6$-cycloalkyl or $C_3$–$C_6$-cycloalkoxy, optionally any of the last-mentioned 8 radicals, being substituted by one to three substituents, in each case selected from the group consisting of halogen, $C_1$–$C_6$-alkoxy and —CO—$OR^{8'}$;
$R^7$ is hydrogen, $C_1$–$C_6$-alkyl, $C_1$–$C_6$-haloalkyl, $C_3$–$C_6$-cycloalkyl, $C_3$–$C_6$-alkenyl, $C_3$–$C_6$-alkynyl, ($C_1$–$C_6$-alkoxy)carbonyl-$C_1$–$C_6$-alkyl or benzyl;

$R^8$, $R^{8'}$ independently of one another are hydrogen, $C_1$–$C_6$-alkyl, $C_3$–$C_6$-cycloalkyl, $C_3$–$C_6$-cycloalkyl-$C_1$–$C_4$-alkyl, $C_3$–$C_6$-alkenyl, $C_3$–$C_6$-alkynyl, $C_1$–$C_6$-alkoxy-$C_1$–$C_6$-alkyl, ($C_1$–$C_6$-alkoxy)carbonyl-$C_1$–$C_6$-alkyl, ($C_3$–$C_6$-alkenyloxy)carbonyl-$C_1$–$C_6$-alkyl, phenyl or phenyl-$C_1$–$C_6$-alkyl, it being possible for the phenyl group and the phenyl ring of the phenyl alkyl group to be unsubstituted or to have attached to them one to three radicals, in each case selected from the group consisting of halogen, nitro, cyano, $C_1$–$C_6$-alkyl, $C_1$–$C_6$-haloalkyl, $C_1$–$C_6$-alkoxy and ($C_1$–$C_6$-alkyl)carbonyl;

$R^9$ is hydrogen or $C_1$–$C_6$-alkyl;

$R^{10}$ is hydrogen, $C_1$–$C_6$-alkyl or $C_1$–$C_6$-alkoxy, it being possible for the 2 last-mentioned radicals to have attached to them one of the following substituents: $C_1$–$C_6$-alkoxy, ($C_1$–$C_6$-alkoxy)carbonyl or phenoxycarbonyl;

$R^{11}$ is hydrogen, $C_1$–$C_6$-alkyl or $C_1$–$C_6$-haloalkyl;

$R^{13}$, $R^{14}$ independently of one another are $C_1$–$C_6$-alkyl or together are a saturated 2- to 4-membered carbon chain which can have attached to it a $C_1$–$C_6$-alkyl radical;

$R^{15}$ is hydrogen, cyano, halogen or $C_1$–$C_6$-alkyl;

$R^{16}$ is O—$R^{23}$ or —N($R^{21}$)$R^{22}$;

$R^{20}$, $R^{23}$ independently of one another are hydrogen, $C_1$–$C_6$-alkyl, $C_1$–$C_6$-haloalkyl, $C_2$–$C_6$-alkenyl or $C_2$–$C_6$-alkynyl, it being possible for any of the last-mentioned 4 groups to be substituted by one or two of the following radicals: cyano, halogen, hydroxyl, hydroxycarbonyl, $C_1$–$C_6$-alkoxy, $C_1$–$C_6$-alkylthio, ($C_1$–$C_6$-alkyl)carbonyl, ($C_1$–$C_6$-alkoxy)carbonyl, ($C_1$–$C_6$-alkyl)carbonyloxy, ($C_3$–$C_6$-alkenyloxy)carbonyl, ($C_3$–$C_6$-alkynyloxy)carbonyl or phenyl or phenyl-$C_1$–$C_6$-alkyl, where the phenyl rings can be unsubstituted or, in turn, can have attached to them one to three substituents, in each case selected from the group consisting of cyano, nitro, halogen, $C_1$–$C_6$-alkyl, $C_1$–$C_6$-haloalkyl, $C_1$–$C_6$-alkoxy and ($C_1$–$C_6$-alkoxy)carbonyl;

$R^{21}$, $R^{22}$ independently of one another are hydrogen, $C_1$–$C_6$-alkyl, $C_3$–$C_6$-alkenyl, $C_2$–$C_6$-alkynyl, $C_3$–$C_6$-cycloalkyl, $C_1$–$C_6$-haloalkyl, $C_1$–$C_6$-alkoxy-$C_1$–$C_6$-alkyl, ($C_1$–$C_6$-alkyl)carbonyl, ($C_1$–$C_6$-alkoxy)carbonyl, ($C_1$–$C_6$-alkoxy)carbonyl-$C_1$–$C_6$-alkyl or $C_1$–$C_6$-alkylsulfonyl, or $R^{21}$ and $R^{22}$ together with the joint nitrogen atom, form a saturated or unsaturated 4- to 7-membered aza heterocycle which optionally contains one of the following members, in addition to carbon ring members: —O—, —S—, —N=, —NH— or —N($C_1$–$C_6$-alkyl)—;

or an agriculturally useful salt or enol ether of a compound I.

2. A 1-aryl4-thiotriazine of the formula I as defined in claim 1 where Y together with $R^5$ is a bridge >C—O—C($R^6$)=N—.

3. A 1-aryl-4-thiotriazine of the formula I as defined in claim 1 where $R^5$ is hydroxyl, 2) $C_1$–$C_6$-alkoxy, $C_3$–$C_6$-cycloalkoxy, $C_2$–$C_6$-alkenyloxy or $C_2$–$C_6$-alkynyloxy, it being possible for each of these 4 radicals optionally to have attached to it one of the following substituents: halogen, cyano, —CO—$R^8$, —CO—OR$^8$ or —CO—N($R^8$)$R^9$.

4. A 1-aryl-4-thiotriazine of the formula I as defined in claim 1 where $R^5$ is mercapto, 2) $C_1$–$C_6$-alkylthio, $C_3$–$C_6$-cycloalkylthio, $C_2$–$C_6$-alkenylthio or $C_2$–$C_6$-alkynylthio, optionally any of the latter 4 radicals substituted by one of the following substituents: halogen, cyano, —CO—$R^8$, —CO—OR$^8$ or —CO—N($R^8$)$R^9$.

5. A 1-aryl-4-thiotriazine of the formula I as defined in claim 1 where $R^5$ is $C_1$–$C_6$-alkyl, $C_1$–$C_6$-haloalkyl, 3) —CO—$R^{11}$, —C($R^{11}$)(OR$^{13}$)(OR$^{14}$), —C($R^{11}$)=C($R^{15}$)—CO—$R^{16}$, —CH($R^{11}$)—CH($R^{15}$)—CO—$R^{16}$, —CO—OR$^{20}$, —C($R^{10}$)=N—OR$^7$ or —CO—N($R^{21}$)—$R^{22}$.

6. A 1-aryl-4-thiotriazine of the formula 1 as defined in claim 1 where $R^5$ is hydrogen, nitro, halogen or —N($R^{21}$)—$R^{22}$.

7. A herbicidal composition comprising a herbicidally active amount of at least one 1-aryl-4-thiotriazine of the formula I or of an agriculturally useful salt or enol ether of I as defined in claim 1 and at least one inert liquid and/or solid carrier and, if desired, at least one surfactant.

8. A process for the preparation of herbicidally active compositions which comprises mixing a herbicidally active amount of at least one 1-aryl-4-thiotriazine of the formula I or of an agriculturally useful salt or enol ether of I as defined in claim 1 and at least one inert liquid and/or solid carrier and optionally at least one surfactant.

9. A method of controlling undesired vegetion, which comprises allowing a herbicidally active amount of at least one 1-aryl-4-thiotriazine of the formula I or of an agriculturally useful salt or enol ether of I as defined in claim 1 to act on plants, their environment or on seed.

10. A process for the preparation of a 1-aryl-4-thiotriazine of the formula I as defined in claim 1, wherein an isocyanate of the formula V

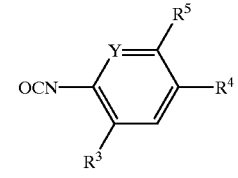

V is reacted with a thiourea of the formula IV

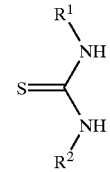

IV in the presence of an activated form of carbonic acid.

* * * * *

UNITED STATES PATENT AND TRADEMARK OFFICE
CERTIFICATE OF CORRECTION

PATENT NO. : 6,602,825 B1
DATED : August 5, 2003
INVENTOR(S) : Menke et al.

It is certified that error appears in the above-identified patent and that said Letters Patent is hereby corrected as shown below:

Column 50,
Line 52, after the comma at the end of the line, insert -- or is --; and
delete the material on lines 57-64 (definition for $R^6$).

Column 51,
Line 36, after "or" insert -- $C_1$-$C_6$-alkoxy-($C_1$-$C_6$-alkoxy), carbonyl or $C_3$-$C_6$-cycloalkyl, --;
Lines 56-58, cancel the claim;
Lines 60-61, delete "hydroxyl, 2)".

Column 52,
Lines 5-6, delete "mercapto, 2)";
Lines 12-13, delete "$C_1$-$C_6$-alkyl, $C_1$-$C_6$-haloalkyl, 3";
Line 18, delete "hydrogen, nitro, halogen or";
Line 22, delete "or enol ether";
Line 24, "if desired" should be -- optionally --;
Lines 28 and 34, delete "or enol ether".

Signed and Sealed this

Ninth Day of December, 2003

JAMES E. ROGAN
*Director of the United States Patent and Trademark Office*